(12) United States Patent
Hsu et al.

(10) Patent No.: US 8,444,981 B2
(45) Date of Patent: May 21, 2013

(54) ALPHA-4 BETA-7 HETERODIMER SPECIFIC ANTAGONIST ANTIBODY

(75) Inventors: Hailing Hsu, Moorpark, CA (US); Ian Foltz, Burnaby (CA); Taruna Arora, Thousand Oaks, CA (US); Frederick W. Jacobsen, Newbury Park, CA (US)

(73) Assignee: Amgen Inc., Thousand Oaks, CA (US)

( * ) Notice: Subject to any disclaimer, the term of this patent is extended or adjusted under 35 U.S.C. 154(b) by 288 days.

(21) Appl. No.: 12/725,031

(22) Filed: Mar. 16, 2010

(65) Prior Publication Data

US 2010/0254975 A1 Oct. 7, 2010

Related U.S. Application Data

(60) Provisional application No. 61/306,829, filed on Feb. 22, 2010, provisional application No. 61/162,154, filed on Mar. 20, 2009.

(51) Int. Cl.
*A61K 39/395* (2006.01)
*C07K 16/18* (2006.01)
*C07K 16/28* (2006.01)

(52) U.S. Cl.
USPC .............. 424/143.1; 424/130.1; 424/133.1; 424/141.1; 530/387.1; 530/388.1; 530/388.22

(58) Field of Classification Search
None
See application file for complete search history.

(56) References Cited

U.S. PATENT DOCUMENTS

| | | | |
|---|---|---|---|
| 5,840,299 | A | 11/1998 | Bendig et al. |
| 7,147,851 | B1 | 12/2006 | Ponath et al. |
| 7,435,802 | B2 | 10/2008 | Bendig et al. |
| 2007/0122404 | A1 | 5/2007 | O'Keefe |
| 2008/0299129 | A1 | 12/2008 | Lewis et al. |

FOREIGN PATENT DOCUMENTS

| | | |
|---|---|---|
| WO | WO 95/19790 | 7/1995 |
| WO | WO 97/18838 | 5/1997 |
| WO | WO 98/06248 | 2/1998 |
| WO | WO 01/27279 | 4/2001 |
| WO | WO 01/78779 | 10/2001 |
| WO | WO02/076406 | 10/2002 |
| WO | WO 2004/016769 | 2/2004 |
| WO | WO 2005/067620 | 7/2005 |
| WO | WO 2006/017538 | 2/2006 |
| WO | WO 2007/061679 | 5/2007 |

OTHER PUBLICATIONS

MacCallum et al. (1996). J. Mol. Biol. 262:732-745.*
De Pascalis et al. (2002). Journal of Immunology. 169:3076-3084.*
Casset et al. (2003). Biochemical and Biophysical Reseaerch Communications. 307:198-205.*
Chen et al. (1999). J. Mol. biol. 293:865-881.*
Wu et al. (1999). J. Mol. Biol. 294:151-162.*
Stefanich, E. G. et al., "A humanized monoclonal antibody targeting the β7 integrin selectively blocks intestinal homing of T lymphocytes," *British J. Pharm.,* 162:1855-1870, 2011.
Vermeire, S. et al., "The mucosal addressin cell adhesion molecule antibody PF-00547,659 in ulcerative colitis: a randomized study," *Gut online, 10 1136/gut.*2010.226548, 2011.
Feagan et al., "Treatment of active Crohn's disease with MLN0002, a humanized antibody to the α4β7 integrin," *Clin Gastroenterol Hepatol,* 6:1370-1377, 2008.
Fegan et al., "Treatment of ulcerative colitis with a humanized antibody to the α4β7 integrin," *N Engl J Med,* 352:2499-2507, 2005.
Ghosh et al., "Natalizumab for active Crohn's disease," *N Engl J Med,* 348:24-32, 2003.
Hesterberg et al., "Rapid resolution of chronic colitis in the cotton-top tamarin with an antibody to a gut-homing integrin α4β7," *Gastroenterology,* 111:1373-1380, 1996.
Lazarovits et al., "Lymphocyte activation antigens: I. A monoclonal antibody, anti-act I, defines a new late lymphocyte activation antigen," *J Immunol,* 133(4):1857-1862, 1984.
Podolsky et al., "Attenuation of colitis in the cotton-top tamarin by anti-α4 integrin monoclonal antibody," *J Clin Invest,* 92:372-380, 1993.
Sandborn et al., "Natalizumab induction and maintenance therapy for Crohn's disease," *N Engl J Med,* 353(18):1912-1925, 2005.
Schiffer et al., "Molecular mapping of functional antibody binding sites of α4 integrin," *J Biol Chem,* 270(24):14270-14273, 1995.
Schweighoffer et al., "Selective expression of integrin α4β7 on a subset of human CD4+ memory T cells with hallmarks of gut-trophism," *J Immunol,* 151(2):717-729, 1993.
Tidswell et al., "Structure-function analysis of the integrin $β_7$ subunit. Identification of domains involved in adhesion to MAdCAM-$1_{1,2}$," *J Immunol,* 159:1497-1505, 1997.
Green, Larry, "Antibody engineering via genetic engineering of the mouse: XenoMouse strains are a vehicle for the facile generation of therapeutic human monoclonal antibodies," *J Immunol Methods* 1999; 231:11-23.
Rudikoff et al., "Single amino acid substitution altering antigen-binding specificity," *PNAS USA 1982*; 79:1979-1983.
Rutgeerts et al., "Biological therapies for inflammatory bowel diseases," *Gastroenterology 2009*; 136:1182-1197.
Soler et al., "The binding specificity and selective antagonism of Vedolizumab, an anti- α4β7 Integrin therapeutic antibody in development for inflammatory bowel diseases," *J Pharmacol Exp Ther 2009*; 330(3):864-875.
Stagg et al., "Intestinal dendritic cells increase T cell expression of alpha4beta7 integrin," *Eur. J. Immunol.,* 32(5):1445-1454, 2002.
Lehnert et al., "MAdCAM-1 constimulates T cell proliferation exclusively through integrin alpha4beta7, where as VCAM-1 and CS-1 peptide use alpha4beta1: evidence for "remote" costimulation and induction of hyperresponsiveness to B7 molecules," *Eur. J. Immunol.,* 28(11):3605-3615, 1998.

* cited by examiner

*Primary Examiner* — Christine J Saoud
*Assistant Examiner* — Jon M Lockard
(74) *Attorney, Agent, or Firm* — Marshall, Gerstein & Borun LLP

(57) ABSTRACT

There are disclosed alpha4beta7 heterodimer-specific antigen binding proteins, nucleic acids encoding them, and methods of making and using them.

36 Claims, No Drawings

SEQUENCE LISTING

```
<160> NUMBER OF SEQ ID NOS: 72

<210> SEQ ID NO 1
<211> LENGTH: 107
<212> TYPE: PRT
<213> ORGANISM: Homo sapiens

<400> SEQUENCE: 1

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Gly Met Ala Pro Lys Leu Leu Ile
        35                  40                  45

Tyr Ala Ala Ser Ile Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ala Asn Ser Phe Pro Trp
                 85                  90                  95

Thr Phe Gly Gln Gly Thr Lys Val Glu Ile Lys
            100                 105

<210> SEQ ID NO 2
<211> LENGTH: 108
<212> TYPE: PRT
<213> ORGANISM: Homo sapiens

<400> SEQUENCE: 2

Glu Ile Val Met Thr Gln Ser Pro Ala Thr Leu Ser Val Ser Pro Gly
 1               5                  10                  15

Glu Thr Ala Thr Leu Ser Cys Arg Ala Ser Gln Thr Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asp Tyr Trp Pro Pro
                 85                  90                  95

Leu Thr Phe Gly Gly Gly Thr Arg Val Glu Ile Lys
            100                 105

<210> SEQ ID NO 3
<211> LENGTH: 107
<212> TYPE: PRT
<213> ORGANISM: Homo sapiens

<400> SEQUENCE: 3

Asp Ile Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Tyr
             20                  25                  30

Leu Ala Trp Tyr Gln Arg Lys Pro Gly Lys Val Pro Lys Leu Leu Ile
         35                  40                  45

Tyr Ala Ala Ser Thr Leu Gln Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Val Ala Thr Tyr Cys Cys Gln Lys Tyr Asp Ser Ala Pro Phe
                 85                  90                  95

Thr Phe Gly Pro Gly Thr Lys Val Asp Ile Lys
            100                 105

<210> SEQ ID NO 4
<211> LENGTH: 107
<212> TYPE: PRT
<213> ORGANISM: Homo sapiens

<400> SEQUENCE: 4

Asp Ile Gln Met Thr Gln Ser Pro Ser Ser Val Phe Ala Ser Val Gly
 1               5                  10                  15

Asp Arg Val Thr Ile Thr Cys Arg Ala Ser Gln Gly Ile Ser Ser Trp
```

```
                    20                  25                  30
Leu Ala Trp Tyr Gln Gln Lys Pro Gly Lys Ala Pro Asn Leu Leu Ile
            35                  40                  45
Tyr Gly Ala Ser Ser Leu Gln Asn Gly Val Pro Leu Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Trp
                85                  90                  95
Thr Phe Gly Gln Gly Thr Lys Val Glu Ile Lys
                100                 105

<210> SEQ ID NO 5
<211> LENGTH: 111
<212> TYPE: PRT
<213> ORGANISM: Homo sapiens

<400> SEQUENCE: 5

Gln Ser Val Leu Thr Gln Pro Pro Ser Val Ser Ala Ala Pro Gly Gln
1               5                   10                  15
Lys Val Thr Ile Ser Cys Ser Gly Ser Ser Asn Ile Gly Asn Asn
                20                  25                  30
Tyr Val Ser Trp Tyr Gln Gln Leu Pro Gly Thr Ala Pro Lys Leu Leu
            35                  40                  45
Ile Tyr Asp Asn Asn Lys Arg Pro Ser Gly Ile Pro Asp Arg Phe Ser
        50                  55                  60
Gly Ser Lys Ser Gly Thr Ser Ala Ile Leu Asp Ile Thr Gly Leu Gln
65                  70                  75                  80
Thr Gly Asp Glu Ala Asp Tyr Tyr Cys Gly Thr Trp Asp Ser Ser Leu
                85                  90                  95
Ser Ala Gly Arg Val Phe Gly Gly Gly Thr Lys Leu Thr Val Leu
                100                 105                 110

<210> SEQ ID NO 6
<211> LENGTH: 107
<212> TYPE: PRT
<213> ORGANISM: Homo sapiens

<400> SEQUENCE: 6

Asp Ile Gln Met Thr Gln Ser Pro Ser Ser Val Ser Ala Ser Val Gly
1               5                   10                  15
Asp Arg Val Thr Ile Thr Cys Arg Ala Ser Gln Gly Val Ile Ser Trp
                20                  25                  30
Leu Ala Trp Tyr Gln Gln Lys Pro Gly Met Ala Pro Lys Leu Leu Ile
            35                  40                  45
Tyr Ala Ala Ser Ile Leu Gln Ser Gly Val Pro Ser Arg Phe Ser Gly
        50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Gln Gln Ala Asn Ser Phe Pro Trp
                85                  90                  95
Thr Phe Gly Gln Gly Thr Asn Val Glu Ile Lys
                100                 105

<210> SEQ ID NO 7
<211> LENGTH: 107
<212> TYPE: PRT
<213> ORGANISM: Homo sapiens
```

<400> SEQUENCE: 7

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Asn Asn Trp
            20                  25                  30

Leu Ala Trp Tyr Gln Gln Lys Pro Gly Lys Ala Pro Lys Leu Leu Ile
        35                  40                  45

Phe Ala Thr Ser Ser Leu Gln Ser Gly Val Pro Ser Arg Phe Ser Gly
50                  55                  60

Ser Gly Ser Gly Thr Asp Phe Thr Leu Thr Ile Asn Ser Leu Gln Pro
65                  70                  75                  80

Glu Asp Phe Ala Thr Tyr Tyr Cys Gln Gln Val Asn Ser Phe Pro Gly
                85                  90                  95

Thr Phe Gly Gln Gly Thr Lys Val Glu Ile Lys
            100                 105

<210> SEQ ID NO 8
<211> LENGTH: 106
<212> TYPE: PRT
<213> ORGANISM: Homo sapiens

<400> SEQUENCE: 8

Glu Ile Val Met Met Gln Ser Pro Ala Thr Leu Ser Val Ser Pro Gly
1               5                   10                  15

Glu Arg Ala Thr Leu Ser Cys Arg Ala Ser Gln Ser Val Ser Thr Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Phe Cys Gln Gln Tyr Asn Asp Trp Pro Thr
                85                  90                  95

Phe Gly Gly Gly Thr Lys Val Glu Ile Lys
            100                 105

<210> SEQ ID NO 9
<211> LENGTH: 107
<212> TYPE: PRT
<213> ORGANISM: Homo sapiens

<400> SEQUENCE: 9

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Gly Ala Ser Asn Leu Glu Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Asn Tyr Tyr Cys Gln Gln Ala Asn Ser Phe Pro Trp
                85                  90                  95

Thr Phe Gly Gln Gly Thr Lys Val Glu Ile Lys

-continued

```
            100                 105

<210> SEQ ID NO 10
<211> LENGTH: 108
<212> TYPE: PRT
<213> ORGANISM: Homo sapiens

<400> SEQUENCE: 10

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Pro Thr Phe Gly Gly Gly Thr Lys Val Ala Ile Lys
            100                 105

<210> SEQ ID NO 11
<211> LENGTH: 108
<212> TYPE: PRT
<213> ORGANISM: Homo sapiens

<400> SEQUENCE: 11

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asn Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Pro
                85                  90                  95

Val Thr Phe Gly Gln Gly Thr Arg Leu Glu Ile Lys
            100                 105

<210> SEQ ID NO 12
<211> LENGTH: 110
<212> TYPE: PRT
<213> ORGANISM: Homo sapiens

<400> SEQUENCE: 12

Gln Ser Val Leu Thr Gln Pro Pro Ser Val Ser Glu Ala Pro Arg Gln
1               5                   10                  15

Arg Val Thr Ile Ser Cys Ser Gly Ser Asn Ser Asn Ile Gly Asn Asn
            20                  25                  30

Pro Val Asn Trp Tyr Gln Leu Phe Pro Gly Arg Ala Pro Lys Leu Leu
        35                  40                  45

Ile Tyr His Asp Asp Leu Leu Pro Ser Gly Val Ser Asp Arg Phe Ser
    50                  55                  60
```

Gly Ser Arg Ser Gly Thr Ser Ala Ser Leu Ala Ile Ser Gly Leu Gln
65                  70                  75                  80

Ser Glu Asp Glu Thr Asp Tyr Tyr Cys Thr Ala Trp Asp Asp Ser Leu
                85                  90                  95

Asn Gly Trp Val Phe Gly Gly Gly Thr Lys Leu Thr Val Leu
            100                 105                 110

<210> SEQ ID NO 13
<211> LENGTH: 106
<212> TYPE: PRT
<213> ORGANISM: Homo sapiens

<400> SEQUENCE: 13

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Asp Asn
            20                  25                  30

Leu Ala Trp Tyr Gln Gln Lys Pro Gly Gln Pro Pro Arg Leu Leu Ile
        35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Thr
                85                  90                  95

Phe Gly Gly Gly Thr Arg Val Glu Ile Lys
            100                 105

<210> SEQ ID NO 14
<211> LENGTH: 107
<212> TYPE: PRT
<213> ORGANISM: Homo sapiens

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
50                  55                  60

Ser Gly Ser Gly Thr Asp Phe Thr Phe Thr Ile Asn Ser Leu Gln Pro
65                  70                  75                  80

Glu Asp Ile Ala Thr Tyr Phe Cys Gln Gln Tyr Asp Asn Leu Pro Cys
                85                  90                  95

Ser Phe Gly Gln Gly Thr Lys Leu Glu Ile Lys
            100                 105

<210> SEQ ID NO 15
<211> LENGTH: 107
<212> TYPE: PRT
<213> ORGANISM: Homo sapiens

<400> SEQUENCE: 15

Asp Ile Gln Met Thr Gln Ser Pro Ser Ser Leu Ser Ala Ser Val Gly
1               5                   10                  15

Asp Arg Val Thr Ile Ser Cys Gln Ala Ser Gln Asp Ile Asn Thr Tyr
            20                  25                  30

```
Leu Asn Trp Tyr Gln Gln Lys Pro Gly Lys Val Pro Lys Leu Leu Ile
            35                  40                  45

Tyr Asp Ala Ser Asn Leu Glu Thr Gly Val Pro Ser Arg Phe Ser Gly
 50                  55                  60

Ser Gly Ser Gly Thr Asp Phe Thr Phe Thr Ile Ser Gly Leu Gln Pro
 65                  70                  75                  80

Glu Asp Ile Ala Thr Tyr Tyr Cys Gln Gln Phe Asp Asn Leu Pro Ile
                 85                  90                  95

Thr Phe Gly Gln Gly Thr Arg Leu Glu Ile Lys
            100                 105
```

<210> SEQ ID NO 16
<211> LENGTH: 107
<212> TYPE: PRT
<213> ORGANISM: Homo sapiens

<400> SEQUENCE: 16

```
Asp Val Gln Met Thr Gln Ser Pro Ser Ser Leu Ser Ala Ser Val Gly
 1               5                  10                  15

Asp Arg Val Thr Ile Thr Cys Gln Ala Ser Gln Asp Ile Thr Asp Tyr
            20                  25                  30

Leu Asn Trp Tyr Gln Gln Lys Pro Gly Lys Ala Pro Lys Leu Leu Ile
            35                  40                  45

Tyr Asp Thr Ser Asn Leu Glu Ala Gly Val Pro Ser Arg Phe Ser Gly
 50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Tyr Asp Ile Leu Pro Tyr
                 85                  90                  95

Ser Phe Gly Gln Gly Thr Asp Leu Glu Ile Lys
            100                 105
```

<210> SEQ ID NO 17
<211> LENGTH: 106
<212> TYPE: PRT
<213> ORGANISM: Homo sapiens

<400> SEQUENCE: 17

```
Glu Val Met Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
            35                  40                  45

Phe Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Cys Cys Gln Gln Tyr Asp Asp Trp Pro Thr
                 85                  90                  95

Phe Gly Gly Gly Thr Lys Val Glu Ile Lys
            100                 105
```

<210> SEQ ID NO 18
<211> LENGTH: 108
<212> TYPE: PRT
<213> ORGANISM: Homo sapiens -continued

<400> SEQUENCE: 18

```
Glu Leu Val Met Thr Gln Ser Pro Ala Thr Leu Ser Val Ser Pro Gly
1               5                   10                  15

Glu Arg Ala Thr Val Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Ser Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Leu Thr Phe Gly Gly Gly Thr Lys Val Glu Ile Lys
            100                 105
```

<210> SEQ ID NO 19
<211> LENGTH: 108
<212> TYPE: PRT
<213> ORGANISM: Homo sapiens

<400> SEQUENCE: 19

```
Glu Ile Val Met Thr Gln Ser Pro Ala Thr Leu Ser Val Phe Pro Gly
1               5                   10                  15

Glu Gly Ala Thr Leu Ser Cys Arg Ala Ser Gln Ser Val Ser Ser Asp
            20                  25                  30

Leu Ala Trp Tyr Gln Gln Lys Pro Gly Gln Ala Pro Arg Leu Leu Ile
        35                  40                  45

Tyr Gly Ala Ser Ala Arg Ala Thr Gly Ile Pro Ala Arg Phe Ser Gly
50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr His Asp Trp Pro Pro
                85                  90                  95

Leu Ser Phe Gly Gly Gly Thr Lys Val Glu Ile Lys
            100                 105
```

<210> SEQ ID NO 20
<211> LENGTH: 108
<212> TYPE: PRT
<213> ORGANISM: Homo sapiens

<400> SEQUENCE: 20

```
Glu Ile Val Leu Thr Gln Ser Pro Gly Thr Leu Ser Leu Ser Pro Gly
1               5                   10                  15

Glu Gly Ala Thr Leu Ser Cys Arg Ala Ser Gln Thr Val Thr Ser Ser
            20                  25                  30

Tyr Leu Ala Trp Tyr Gln Gln Ser Pro Ser Gln Ser Pro Arg Leu Leu
        35                  40                  45

Ile Tyr Gly Ala Ser Thr Arg Ala Thr Gly Ile Pro Asp Arg Phe Ser
50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Pro Thr Phe Gly Gly Gly Thr Lys Val Glu Ile Lys
            100                 105
```

<210> SEQ ID NO 21
<211> LENGTH: 108
<212> TYPE: PRT
<213> ORGANISM: Homo sapiens

<400> SEQUENCE: 21

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Val Tyr Tyr Cys Gln Gln Tyr Asp Asp Trp Pro Pro
                85                  90                  95

Leu Thr Phe Gly Gly Gly Thr Lys Val Glu Ile Lys
            100                 105

<210> SEQ ID NO 22
<211> LENGTH: 107
<212> TYPE: PRT
<213> ORGANISM: Homo sapiens

<400> SEQUENCE: 22

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Arg Lys Pro Gly Lys Ala Pro Lys Val Leu Ile
        35                  40                  45

Tyr Ser Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Trp
                85                  90                  95

Thr Phe Gly Gln Gly Thr Lys Val Glu Ile Lys
            100                 105

<210> SEQ ID NO 23
<211> LENGTH: 106
<212> TYPE: PRT
<213> ORGANISM: Homo sapiens

<400> SEQUENCE: 23

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Ala
            20                  25                  30

Cys Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met

```
                65                  70                  75                  80
Asp Glu Ala Asp Tyr Tyr Cys Gln Ala Trp Asp Ser Ser Thr Val Val
                    85                  90                  95

Phe Gly Gly Gly Thr Lys Leu Thr Val Leu
            100                 105
```

<210> SEQ ID NO 24
<211> LENGTH: 107
<212> TYPE: PRT
<213> ORGANISM: Homo sapiens

<400> SEQUENCE: 24

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Thr Ala Pro Lys Val Leu Ile
        35                  40                  45

Tyr Ser Ala Ser Ser Leu Gln Asn Gly Val Pro Ser Arg Phe Ser Gly
    50                  55                  60

Arg Gly Ser Gly Thr Asp Phe Ala Leu Thr Ile Ser Ser Leu Gln Pro
65                  70                  75                  80

Glu Asp Phe Ala Thr Tyr Tyr Cys Gln Gln Ala Asp Ser Phe Pro Trp
                85                  90                  95

Thr Phe Gly Arg Gly Thr Lys Val Glu Ile Lys
            100                 105
```

<210> SEQ ID NO 25
<211> LENGTH: 110
<212> TYPE: PRT
<213> ORGANISM: Homo sapiens

<400> SEQUENCE: 25

```
Gln Ser Val Leu Thr Gln Pro Pro Ser Val Ser Gly Ala Pro Arg Gln
1               5                   10                  15

Arg Val Thr Ile Ser Cys Ser Gly Ser Asn Ser Asn Ile Gly Asn Asn
            20                  25                  30

Pro Val Asn Trp Tyr Gln Leu Phe Pro Gly Arg Ala Pro Lys Leu Leu
        35                  40                  45

Ile Tyr His Asp Asp Leu Leu Pro Ser Gly Val Ser Asp Arg Phe Ser
    50                  55                  60

Gly Ser Arg Ser Gly Thr Ser Ala Ser Leu Ala Ile Ser Gly Leu Gln
65                  70                  75                  80

Ser Ala Asp Glu Thr Asp Tyr Tyr Cys Thr Ala Trp Asp Asp Ser Leu
                85                  90                  95

Asn Gly Trp Val Phe Gly Gly Gly Thr Lys Leu Thr Val Leu
            100                 105                 110
```

<210> SEQ ID NO 26
<211> LENGTH: 110
<212> TYPE: PRT
<213> ORGANISM: Homo sapiens

<400> SEQUENCE: 26

```
Gln Ser Val Leu Thr Gln Pro Arg Ser Val Ser Gly Ala Pro Arg Gln
1               5                   10                  15

Arg Val Thr Ile Ser Cys Ser Gly Ser Asn Ser Asn Ile Gly Asn Asn
            20                  25                  30
```

-continued

```
Pro Val Asn Trp Tyr Gln Leu Phe Pro Gly Arg Ala Pro Lys Leu Leu
            35                  40                  45

Ile Tyr His Asp Asp Leu Leu Pro Ser Gly Val Ser Asp Arg Phe Ser
    50                  55                  60

Gly Ser Arg Ser Gly Thr Ser Ala Ser Leu Ala Ile Ser Gly Leu Arg
65                  70                  75                  80

Ser Ala Asp Glu Thr Asp Tyr Tyr Cys Thr Ala Trp Asp Ser Ser Leu
                85                  90                  95

Asn Gly Trp Val Phe Gly Gly Gly Thr Lys Leu Thr Val Leu
                100                 105                 110

<210> SEQ ID NO 27
<211> LENGTH: 107
<212> TYPE: PRT
<213> ORGANISM: Homo sapiens

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Asp Ala Ser Asn Leu Glu Thr Gly Val Pro Ser Arg Phe Ser Gly
    50                  55                  60

Ser Gly Ser Gly Thr Asp Phe Thr Phe Thr Ile Asn Ser Leu Gln Pro
65                  70                  75                  80

Glu Asp Ile Ala Thr Tyr Phe Cys Gln Gln Tyr Asp Asn Leu Pro Ser
                85                  90                  95

Ser Phe Gly Gln Gly Thr Lys Leu Glu Ile Lys
                100                 105

<210> SEQ ID NO 28
<211> LENGTH: 107
<212> TYPE: PRT
<213> ORGANISM: Homo sapiens

<400> SEQUENCE: 28

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Val Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Trp
                85                  90                  95

Thr Phe Gly Gln Gly Thr Lys Val Glu Ile Lys
                100                 105

<210> SEQ ID NO 29
<211> LENGTH: 118
<212> TYPE: PRT
<213> ORGANISM: Homo sapiens

<400> SEQUENCE: 29
```

-continued

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Asn Asp Leu
            20                  25                  30

Ser Met His Trp Val Arg Gln Ala Pro Gly Lys Gly Leu Glu Trp Met
        35                  40                  45

Gly Gly Phe Asp Pro Ala Glu Gly Lys Ile Ile Ser Ala Gln Lys Phe
    50                  55                  60

Gln Asp Arg Val Thr Met Thr Asp Thr Ser Thr Asp Thr Ala Tyr
65                  70                  75                  80

Met Glu Leu Ser Ser Leu Arg Ser Glu Asp Ser Ala Val Tyr Tyr Cys
                85                  90                  95

Ala Thr Leu Asp Phe Ser Ser Trp Phe Asp Pro Trp Gly Gln Gly Thr
            100                 105                 110

Leu Val Thr Val Ser Ser
        115

<210> SEQ ID NO 30
<211> LENGTH: 120
<212> TYPE: PRT
<213> ORGANISM: Homo sapiens

<400> SEQUENCE: 30

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Leu Asn Ser Leu Arg Ala Glu Asp Thr Ala Val Tyr Tyr Cys
                85                  90                  95

Ala Arg Asp Tyr Ser Ser Gly Trp Phe Tyr Phe Asp Tyr Trp Gly Arg
            100                 105                 110

Gly Thr Leu Val Thr Val Ser Ser
        115                 120

<210> SEQ ID NO 31
<211> LENGTH: 118
<212> TYPE: PRT
<213> ORGANISM: Homo sapiens

<400> SEQUENCE: 31

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu His
65                  70                  75                  80

```
Leu Gln Met Asn Ser Leu Arg Ala Glu Asp Thr Ala Val Tyr Tyr Cys
                85                  90                  95

Ala Arg Glu His Trp Asn Tyr Ala Phe Asp Ile Trp Gly Gln Gly Thr
            100                 105                 110

Met Val Thr Val Ser Ser
            115

<210> SEQ ID NO 32
<211> LENGTH: 118
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Val Thr Asp Leu
            20                  25                  30

Ser Met His Trp Val Arg Gln Ala Pro Gly Lys Gly Leu Glu Trp Met
        35                  40                  45

Gly Gly Phe Asp Pro Gln Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Arg Ser Leu Arg Ser Glu Asp Thr Ala Val Tyr Tyr Cys
                85                  90                  95

Thr Thr Glu Ser Ser Ser Ala Trp Phe Asp Pro Trp Gly Gln Gly Thr
            100                 105                 110

Leu Val Thr Val Ser Ser
            115

<210> SEQ ID NO 33
<211> LENGTH: 121
<212> TYPE: PRT
<213> ORGANISM: Homo sapiens

<400> SEQUENCE: 33

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Asn Ser Gly Ser Val Val Tyr Tyr Ala Asp Ser Val
    50                  55                  60

Lys Gly Arg Phe Thr Ile Ser Arg His Asn Ala Lys Asn Ser Leu Tyr
65                  70                  75                  80

Leu Gln Met Asn Ser Leu Arg Ala Asp Asp Thr Ala Val Tyr Tyr Cys
                85                  90                  95

Ala Arg Asp Arg Ser Ser Ala Trp Asp Glu Ala Phe Asp Ile Trp Gly
            100                 105                 110

Gln Gly Thr Met Val Thr Val Ser Ser
            115                 120

<210> SEQ ID NO 34
<211> LENGTH: 118
<212> TYPE: PRT
<213> ORGANISM: Homo sapiens

<400> SEQUENCE: 34
```

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Asn Asp Leu
            20                  25                  30

Ser Met His Trp Val Arg Gln Ala Pro Gly Lys Gly Leu Glu Trp Met
        35                  40                  45

Gly Gly Phe Asp Pro Ala Glu Gly Lys Ile Ile Ser Ala Gln Lys Phe
    50                  55                  60

Gln Asp Arg Val Thr Met Thr Asp Asp Thr Ser Thr Asp Thr Ala Tyr
65                  70                  75                  80

Met Glu Leu Ser Ser Leu Arg Ser Glu Asp Ser Ala Val Tyr Tyr Cys
                85                  90                  95

Ala Thr Leu Asp Phe Ser Ser Trp Phe Asp Pro Trp Gly Gln Gly Thr
            100                 105                 110

Leu Val Thr Val Ser Ser
        115

<210> SEQ ID NO 35
<211> LENGTH: 120
<212> TYPE: PRT
<213> ORGANISM: Homo sapiens

<400> SEQUENCE: 35

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Thr Gly Ser Ala Met Tyr Asp Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Phe Ser Ser Gly Trp Ser Tyr Phe Asp Tyr Trp Gly Gln
            100                 105                 110

Gly Thr Leu Val Thr Val Ser Ser
        115                 120

<210> SEQ ID NO 36
<211> LENGTH: 120
<212> TYPE: PRT
<213> ORGANISM: Homo sapiens

<400> SEQUENCE: 36

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Asn
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Ala Thr Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Ser Ser Leu Arg Ala Glu Asp Thr Ala Val Tyr Tyr Cys
                85                  90                  95

Ala Arg Asp Tyr Ser Ser Gly Trp Tyr Tyr Phe Asp Tyr Trp Gly Gln
            100                 105                 110

Gly Thr Leu Val Thr Val Ser Ser
        115                 120

<210> SEQ ID NO 37
<211> LENGTH: 118
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Ser Asp Leu
            20                  25                  30

Ser Ile His Trp Val Arg Gln Ala Pro Gly Lys Gly Leu Glu Trp Met
        35                  40                  45

Gly Gly Phe Asp Pro Gln Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Lys Ser Glu Asp Thr Ala Val Tyr Tyr Cys
                85                  90                  95

Ala Thr Gly Ser Ser Ser Ser Trp Phe Asp Pro Trp Gly Gln Gly Thr
            100                 105                 110

Leu Val Thr Val Ser Ser
        115

<210> SEQ ID NO 38
<211> LENGTH: 120
<212> TYPE: PRT
<213> ORGANISM: Homo sapiens

<400> SEQUENCE: 38

Gln Val Gln Leu Val Glu Ser Gly Gly Gly Leu Val Lys Pro Gly Gly
1               5                   10                  15

Ser Leu Arg Leu Ser Cys Thr Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ala Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Glu Asp Thr Ala Val Phe Tyr Cys
                85                  90                  95

Ala Arg Glu His Ser Ser Gly Tyr Trp Tyr Phe Asp Leu Trp Gly Arg
            100                 105                 110

Gly Ala Leu Val Thr Val Ser Ser
        115                 120

<210> SEQ ID NO 39
<211> LENGTH: 120
<212> TYPE: PRT
<213> ORGANISM: Homo sapiens

<400> SEQUENCE: 39

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Ala Met Tyr Ser Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Tyr Ser Ser Gly Trp Tyr Tyr Phe Asp Tyr Trp Gly Arg
                100                 105                 110

Gly Thr Leu Val Thr Val Ser Ser
            115                 120
```

<210> SEQ ID NO 40
<211> LENGTH: 120
<212> TYPE: PRT
<213> ORGANISM: Homo sapiens

<400> SEQUENCE: 40

```
Gln Val Gln Leu Val Glu Ser Gly Gly Gly Leu Val Lys Pro Gly Gly
  1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ile Gly Ser Ala Ile His Tyr Ala Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                 85                  90                  95

Ala Arg Glu Tyr Ser Ser Gly Trp Ala Tyr Phe Asp Tyr Trp Gly Gln
                100                 105                 110

Gly Thr Leu Val Thr Val Ser Ser
            115                 120
```

<210> SEQ ID NO 41
<211> LENGTH: 125
<212> TYPE: PRT
<213> ORGANISM: Homo sapiens

<400> SEQUENCE: 41

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Trp Met Ser Trp Val Arg Gln Ala Ser Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
 65                  70                  75                  80
```

```
Leu Gln Met Asn Ser Leu Arg Ala Glu Asp Thr Ala Val Tyr Tyr Cys
                85                  90                  95

Ala Arg Glu Gly Gly Tyr Asp Trp Asn Tyr Ala Asp Tyr Tyr Gly Met
            100                 105                 110

Asp Val Trp Gly Gln Gly Thr Thr Val Thr Val Ser Ser
        115                 120                 125
```

<210> SEQ ID NO 42
<211> LENGTH: 120
<212> TYPE: PRT
<213> ORGANISM: Homo sapiens

<400> SEQUENCE: 42

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Arg Val Gly Ser Thr Thr Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Ser Gly Trp Tyr Tyr Phe Asp Tyr Trp Gly Gln
            100                 105                 110

Gly Thr Leu Val Thr Val Ser Ser
        115                 120
```

<210> SEQ ID NO 43
<211> LENGTH: 123
<212> TYPE: PRT
<213> ORGANISM: Homo sapiens

<400> SEQUENCE: 43

```
Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Gly Tyr
            20                  25                  30

Trp Ile Gly Trp Val Arg Gln Met Pro Gly Lys Gly Leu Glu Trp Met
        35                  40                  45

Gly Ile Ile Tyr Pro Tyr Asp Ser Asp Thr Arg Tyr Ser Pro Ser Phe
50                  55                  60

Gln Gly Gln Val Thr Ile Ser Ala Asp Lys Ser Ile Asn Thr Ala Tyr
65                  70                  75                  80

Leu Gln Trp Ser Ser Leu Lys Ala Ser Asp Thr Ala Met Phe Tyr Cys
                85                  90                  95

Ala Ser His Arg Leu Trp Leu Gly Glu Phe Pro Gly Pro Leu Asn Ile
            100                 105                 110

Trp Gly Gln Gly Thr Met Val Thr Val Ser Ser
        115                 120
```

<210> SEQ ID NO 44
<211> LENGTH: 120
<212> TYPE: PRT
<213> ORGANISM: Homo sapiens

<400> SEQUENCE: 44

```
Gln Val Gln Leu Val Glu Ser Gly Gly Asp Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Ile
        35                  40                  45

Ser Tyr Ile Ser Ser Ser Gly Ser Thr Met Tyr Tyr Ala Asp Ser Val
    50                  55                  60

Lys Gly Arg Phe Thr Ile Ser Arg Val Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Ser Ser Gly Leu Val Ser Phe Asp Tyr Trp Gly Gln
                100                 105                 110

Gly Thr Leu Val Thr Val Ser Ser
            115                 120

<210> SEQ ID NO 45
<211> LENGTH: 123
<212> TYPE: PRT
<213> ORGANISM: Homo sapiens

<400> SEQUENCE: 45

Glu Val Gln Leu Val Gln Ser Gly Ala Glu Val Lys Glu Pro Gly Glu
1               5                   10                  15

Ser Leu Lys Ile Ser Cys Lys Gly Ser Gly Tyr Ile Phe Thr Ser Tyr
            20                  25                  30

Trp Ile Ala Trp Val Arg Gln Leu Pro Gly Lys Gly Leu Glu Trp Met
        35                  40                  45

Gly Ile Ile Asp Pro Asn Asp Ser Asp Thr Arg Tyr Ser Pro Ser Phe
    50                  55                  60

Gln Gly Gln Val Thr Ile Ser Ala Asp Lys Ser Ile His Thr Ala Tyr
65                  70                  75                  80

Leu Gln Trp Ser Ser Leu Lys Ala Ser Asp Thr Ala Met Tyr Tyr Cys
                85                  90                  95

Ala Thr His Arg Leu Trp Leu Gly Thr Leu Pro Gly Gly Phe Tyr Ile
                100                 105                 110

Trp Gly Gln Gly Thr Met Val Thr Val Ser Ser
            115                 120

<210> SEQ ID NO 46
<211> LENGTH: 120
<212> TYPE: PRT
<213> ORGANISM: Homo sapiens

<400> SEQUENCE: 46

Gln Val Gln Leu Val Glu Ser Gly Gly Asp Leu Val Glu Pro Gly Gly
1               5                   10                  15

Ser Leu Arg Leu Ser Cys Ala Ala Ser Gly Phe Thr Phe Arg Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ala Ile Tyr Tyr Ala Asp Ser Val
    50                  55                  60

Lys Gly Arg Phe Thr Ile Ser Arg Asp Asn Pro Lys Asn Ser Leu Tyr
65                  70                  75                  80
```

```
Leu Gln Met Asn Ser Leu Arg Ala Glu Asp Thr Ala Val Tyr Tyr Cys
                85                  90                  95

Ala Arg Asp Phe Ser Ser Gly Tyr Tyr Tyr Phe Asp Tyr Trp Gly His
            100                 105                 110

Gly Thr Leu Val Thr Val Ser Ser
        115                 120
```

<210> SEQ ID NO 47
<211> LENGTH: 120
<212> TYPE: PRT
<213> ORGANISM: Homo sapiens

<400> SEQUENCE: 47

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Arg Asp Tyr
            20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Ser Tyr Cys Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Ser Gly Trp Phe Tyr Phe Asp Tyr Trp Gly Gln
            100                 105                 110

Gly Thr Leu Val Thr Val Ser Ser
        115                 120
```

<210> SEQ ID NO 48
<211> LENGTH: 124
<212> TYPE: PRT
<213> ORGANISM: Homo sapiens

<400> SEQUENCE: 48

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Ala Pro Tyr Ser Ser Ser Trp Ala Leu Gly Leu Gly Met Asp
            100                 105                 110

Val Trp Gly Gln Gly Thr Thr Val Thr Val Ser Ser
        115                 120
```

<210> SEQ ID NO 49
<211> LENGTH: 120
<212> TYPE: PRT
<213> ORGANISM: Homo sapiens

<400> SEQUENCE: 49

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Thr Gly Ser Thr Leu Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asp Ser Leu Arg Ala Asp Ala Ala Val Tyr Tyr Cys
                85                  90                  95

Thr Arg Glu Tyr Ser Ser Gly Trp Phe Phe Phe Asp Tyr Trp Gly Gln
                100                 105                 110

Gly Thr Leu Val Thr Val Ser Ser
            115                 120

<210> SEQ ID NO 50
<211> LENGTH: 120
<212> TYPE: PRT
<213> ORGANISM: Homo sapiens

<400> SEQUENCE: 50

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Asn Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Ala Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Ser Gly Trp Ala Tyr Phe Asp Tyr Trp Gly Gln
                100                 105                 110

Gly Thr Leu Val Thr Val Ser Ser
            115                 120

<210> SEQ ID NO 51
<211> LENGTH: 120
<212> TYPE: PRT
<213> ORGANISM: Homo sapiens

<400> SEQUENCE: 51

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asp Tyr
            20                  25                  30

Tyr Met Ser Trp Ile Arg Gln Thr Pro Gly Lys Gly Leu Glu Trp Val
        35                  40                  45

Ser Tyr Ile Ser Ser Ser Gly Ser Ala Ile His Tyr Ala Asp Ser Val
    50                  55                  60

Lys Gly Arg Phe Thr Ile Ser Arg Asp Asn Ala Lys Asn Ser Leu Tyr
65                  70                  75                  80

```
Leu Gln Met Asp Ser Leu Arg Ala Glu Asp Thr Ala Val Phe Tyr Cys
                85                  90                  95

Ala Arg Asp His Ser Ser Gly Tyr Trp Tyr Phe Asp Leu Trp Gly Arg
            100                 105                 110

Gly Thr Leu Val Thr Val Ser Ser
        115                 120
```

<210> SEQ ID NO 52
<211> LENGTH: 120
<212> TYPE: PRT
<213> ORGANISM: Homo sapiens

<400> SEQUENCE: 52

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Leu
        35                  40                  45

Ser Tyr Ile Ser Asn Ser Gly Ser Ala Met Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Tyr Ser Ser Gly Trp Phe Phe Glu Ser Trp Gly Gln
            100                 105                 110

Gly Thr Leu Val Thr Val Ser Ser
        115                 120
```

<210> SEQ ID NO 53
<211> LENGTH: 118
<212> TYPE: PRT
<213> ORGANISM: Homo sapiens

<400> SEQUENCE: 53

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Asn Asp Leu
            20                  25                  30

Ser Met His Trp Val Arg Gln Ala Pro Gly Lys Gly Leu Glu Trp Met
        35                  40                  45

Gly Gly Phe Asp Pro Ala Glu Gly Lys Ile Ile Ser Ala Gln Lys Phe
    50                  55                  60

Gln Asp Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Leu Asp Phe Ser Ser Trp Phe Asp Pro Trp Gly Gln Gly Thr
            100                 105                 110

Leu Val Thr Val Ser Ser
        115
```

<210> SEQ ID NO 54
<211> LENGTH: 125
<212> TYPE: PRT
<213> ORGANISM: Homo sapiens

<400> SEQUENCE: 54

```
Glu Val Gln Leu Val Glu Ser Gly Gly Gly Leu Val Lys Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Ser Gly Lys Gly Leu Glu Trp Val
        35                  40                  45

Ala Asn Ile Lys Gln Asp Gly Ser Glu Lys Tyr Tyr Val Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Gly Asp Thr Ala Val Tyr Tyr Cys
                85                  90                  95

Ala Arg Glu Gly Gly Tyr Asp Trp Asn Tyr Ala Asp Tyr Tyr Gly Met
            100                 105                 110

Asp Val Trp Gly Gln Gly Thr Thr Val Thr Val Ser Ser
            115                 120                 125
```

```
<210> SEQ ID NO 55
<211> LENGTH: 109
<212> TYPE: PRT
<213> ORGANISM: Artificial
<220> FEATURE:
<223> OTHER INFORMATION: Light chain consensus
<220> FEATURE:
<221> NAME/KEY: MISC_FEATURE
<222> LOCATION: (2)..(2)
<223> OTHER INFORMATION: X can be Val, Leu or Ile
<220> FEATURE:
<221> NAME/KEY: MISC_FEATURE
<222> LOCATION: (3)..(3)
<223> OTHER INFORMATION: X can be Met or Val
<220> FEATURE:
<221> NAME/KEY: MISC_FEATURE
<222> LOCATION: (4)..(4)
<223> OTHER INFORMATION: X can be Met or Leu
<220> FEATURE:
<221> NAME/KEY: MISC_FEATURE
<222> LOCATION: (5)..(5)
<223> OTHER INFORMATION: X can be Met or Thr
<220> FEATURE:
<221> NAME/KEY: MISC_FEATURE
<222> LOCATION: (9)..(9)
<223> OTHER INFORMATION: X can be Ala or Gly
<220> FEATURE:
<221> NAME/KEY: MISC_FEATURE
<222> LOCATION: (13)..(13)
<223> OTHER INFORMATION: X can be Leu or Val
<220> FEATURE:
<221> NAME/KEY: MISC_FEATURE
<222> LOCATION: (14)..(14)
<223> OTHER INFORMATION: X can be Phe or Ser
<220> FEATURE:
<221> NAME/KEY: MISC_FEATURE
<222> LOCATION: (18)..(18)
<223> OTHER INFORMATION: X can be Gly, Arg or Thr
<220> FEATURE:
<221> NAME/KEY: MISC_FEATURE
<222> LOCATION: (21)..(21)
<223> OTHER INFORMATION: X can be Val or Leu
<220> FEATURE:
<221> NAME/KEY: MISC_FEATURE
<222> LOCATION: (28)..(28)
<223> OTHER INFORMATION: X can be Thr or Ser
<220> FEATURE:
<221> NAME/KEY: MISC_FEATURE
<222> LOCATION: (30)..(30)
<223> OTHER INFORMATION: X can be thr, Asn or Ser
<220> FEATURE:
<221> NAME/KEY: MISC_FEATURE
<222> LOCATION: (30)..(30)
<223> OTHER INFORMATION: X can be Thr, Asn or Ser
```

```
<220> FEATURE:
<221> NAME/KEY: MISC_FEATURE
<222> LOCATION: (31)..(31)
<223> OTHER INFORMATION: X can be Thr, Asp or Ser
<220> FEATURE:
<221> NAME/KEY: MISC_FEATURE
<222> LOCATION: (32)..(32)
<223> OTHER INFORMATION: X can be Asn, Asp or Ser
<220> FEATURE:
<221> NAME/KEY: MISC_FEATURE
<222> LOCATION: (33)..(33)
<223> OTHER INFORMATION: X can be Tyr or none
<220> FEATURE:
<221> NAME/KEY: MISC_FEATURE
<222> LOCATION: (35)..(35)
<223> OTHER INFORMATION: X can be Val or Ala
<220> FEATURE:
<221> NAME/KEY: MISC_FEATURE
<222> LOCATION: (40)..(40)
<223> OTHER INFORMATION: X can be Ser or Lys
<220> FEATURE:
<221> NAME/KEY: MISC_FEATURE
<222> LOCATION: (42)..(42)
<223> OTHER INFORMATION: X can be Ser or Gly
<220> FEATURE:
<221> NAME/KEY: MISC_FEATURE
<222> LOCATION: (44)..(44)
<223> OTHER INFORMATION: X can be Ser, Pro or Ala
<220> FEATURE:
<221> NAME/KEY: MISC_FEATURE
<222> LOCATION: (50)..(50)
<223> OTHER INFORMATION: X can be Phe or Tyr
<220> FEATURE:
<221> NAME/KEY: MISC_FEATURE
<222> LOCATION: (54)..(54)
<223> OTHER INFORMATION: X can be Thr, Ala or Ser
<220> FEATURE:
<221> NAME/KEY: MISC_FEATURE
<222> LOCATION: (61)..(61)
<223> OTHER INFORMATION: X can be Ala or Asp
<220> FEATURE:
<221> NAME/KEY: MISC_FEATURE
<222> LOCATION: (71)..(71)
<223> OTHER INFORMATION: X can be Glu or Asp
<220> FEATURE:
<221> NAME/KEY: MISC_FEATURE
<222> LOCATION: (78)..(78)
<223> OTHER INFORMATION: X can be Ser or Arg
<220> FEATURE:
<221> NAME/KEY: MISC_FEATURE
<222> LOCATION: (80)..(80)
<223> OTHER INFORMATION: X can be Gln or Glu
<220> FEATURE:
<221> NAME/KEY: MISC_FEATURE
<222> LOCATION: (81)..(81)
<223> OTHER INFORMATION: X can be Pro or Ser
<220> FEATURE:
<221> NAME/KEY: MISC_FEATURE
<222> LOCATION: (88)..(88)
<223> OTHER INFORMATION: X can be Phe, Cys or Tyr
<220> FEATURE:
<221> NAME/KEY: MISC_FEATURE
<222> LOCATION: (93)..(93)
<223> OTHER INFORMATION: X can be His, Asn or Asp
<220> FEATURE:
<221> NAME/KEY: MISC_FEATURE
<222> LOCATION: (94)..(94)
<223> OTHER INFORMATION: X can be Asp, Asn, Tyr or Ser
<220> FEATURE:
<221> NAME/KEY: MISC_FEATURE
<222> LOCATION: (95)..(95)
<223> OTHER INFORMATION: X can be Trp or Ser
<220> FEATURE:
<221> NAME/KEY: MISC_FEATURE
<222> LOCATION: (97)..(97)
<223> OTHER INFORMATION: X can be Pro or none
<220> FEATURE:
<221> NAME/KEY: MISC_FEATURE
<222> LOCATION: (98)..(98)
<223> OTHER INFORMATION: X can be Val, Leu or none
```

-continued

```
<220> FEATURE:
<221> NAME/KEY: MISC_FEATURE
<222> LOCATION: (99)..(99)
<223> OTHER INFORMATION: X can be Thr or Ser
<220> FEATURE:
<221> NAME/KEY: MISC_FEATURE
<222> LOCATION: (102)..(102)
<223> OTHER INFORMATION: X can be Gln or Glu
<220> FEATURE:
<221> NAME/KEY: MISC_FEATURE
<222> LOCATION: (105)..(105)
<223> OTHER INFORMATION: X can be Arg, Thr or Lys
<220> FEATURE:
<221> NAME/KEY: MISC_FEATURE
<222> LOCATION: (106)..(106)
<223> OTHER INFORMATION: X can be Leu or Val
<220> FEATURE:
<221> NAME/KEY: MISC_FEATURE
<222> LOCATION: (107)..(107)
<223> OTHER INFORMATION: X can be Glu or Ala

<400> SEQUENCE: 55

Glu Xaa Xaa Xaa Xaa Gln Ser Pro Xaa Thr Leu Ser Xaa Xaa Pro Gly
 1               5                  10                  15

Glu Xaa Ala Thr Xaa Ser Cys Arg Ala Ser Gln Xaa Val Xaa Xaa Xaa
            20                  25                  30

Xaa Leu Xaa Trp Tyr Gln Gln Xaa Pro Xaa Gln Xaa Pro Arg Leu Leu
        35                  40                  45

Ile Xaa Gly Ala Ser Xaa Arg Ala Thr Gly Ile Pro Xaa Arg Phe Ser
50                  55                  60

Gly Ser Gly Ser Gly Thr Xaa Phe Thr Leu Thr Ile Ser Xaa Leu Xaa
65                  70                  75                  80

Xaa Glu Asp Phe Ala Val Tyr Xaa Cys Gln Gln Tyr Xaa Xaa Xaa Pro
                85                  90                  95

Xaa Xaa Xaa Phe Gly Xaa Gly Thr Xaa Xaa Xaa Ile Lys
            100                 105

<210> SEQ ID NO 56
<211> LENGTH: 107
<212> TYPE: PRT
<213> ORGANISM: Artificial
<220> FEATURE:
<223> OTHER INFORMATION: Light chain consensus
<220> FEATURE:
<221> NAME/KEY: MISC_FEATURE
<222> LOCATION: (11)..(11)
<223> OTHER INFORMATION: X can be Val or Leu
<220> FEATURE:
<221> NAME/KEY: MISC_FEATURE
<222> LOCATION: (12)..(12)
<223> OTHER INFORMATION: X can be Ser or Phe
<220> FEATURE:
<221> NAME/KEY: MISC_FEATURE
<222> LOCATION: (15)..(15)
<223> OTHER INFORMATION: X can be Val or Ile
<220> FEATURE:
<221> NAME/KEY: MISC_FEATURE
<222> LOCATION: (28)..(28)
<223> OTHER INFORMATION: X can be Asp or Gly
<220> FEATURE:
<221> NAME/KEY: MISC_FEATURE
<222> LOCATION: (29)..(29)
<223> OTHER INFORMATION: X can be Ile or Val
<220> FEATURE:
<221> NAME/KEY: MISC_FEATURE
<222> LOCATION: (30)..(30)
<223> OTHER INFORMATION: X can be Ser, Ile, Asn or Arg
<220> FEATURE:
<221> NAME/KEY: MISC_FEATURE
<222> LOCATION: (31)..(31)
<223> OTHER INFORMATION: X can be Ser or Asn
<220> FEATURE:
```

```
<221> NAME/KEY: MISC_FEATURE
<222> LOCATION: (32)..(32)
<223> OTHER INFORMATION: X can be Trp or Tyr
<220> FEATURE:
<221> NAME/KEY: MISC_FEATURE
<222> LOCATION: (38)..(38)
<223> OTHER INFORMATION: X can be Arg or Gln
<220> FEATURE:
<221> NAME/KEY: MISC_FEATURE
<222> LOCATION: (42)..(42)
<223> OTHER INFORMATION: X can be Lys, Met or Thr
<220> FEATURE:
<221> NAME/KEY: MISC_FEATURE
<222> LOCATION: (43)..(43)
<223> OTHER INFORMATION: X can be Ala or Val
<220> FEATURE:
<221> NAME/KEY: MISC_FEATURE
<222> LOCATION: (45)..(45)
<223> OTHER INFORMATION: X can be Lys or Asn
<220> FEATURE:
<221> NAME/KEY: MISC_FEATURE
<222> LOCATION: (46)..(46)
<223> OTHER INFORMATION: X can be Val or Leu
<220> FEATURE:
<221> NAME/KEY: MISC_FEATURE
<222> LOCATION: (49)..(49)
<223> OTHER INFORMATION: X can be Tyr or Phe
<220> FEATURE:
<221> NAME/KEY: MISC_FEATURE
<222> LOCATION: (50)..(50)
<223> OTHER INFORMATION: X can be Ser, Ala or Gly
<220> FEATURE:
<221> NAME/KEY: MISC_FEATURE
<222> LOCATION: (51)..(51)
<223> OTHER INFORMATION: X can be Ala or Thr
<220> FEATURE:
<221> NAME/KEY: MISC_FEATURE
<222> LOCATION: (53)..(53)
<223> OTHER INFORMATION: X can be Ser, Ile, Asn or Thr
<220> FEATURE:
<221> NAME/KEY: MISC_FEATURE
<222> LOCATION: (55)..(55)
<223> OTHER INFORMATION: X can be Gln or Glu
<220> FEATURE:
<221> NAME/KEY: MISC_FEATURE
<222> LOCATION: (56)..(56)
<223> OTHER INFORMATION: X can be Ser or Asn
<220> FEATURE:
<221> NAME/KEY: MISC_FEATURE
<222> LOCATION: (60)..(60)
<223> OTHER INFORMATION: X can be Ser or Leu
<220> FEATURE:
<221> NAME/KEY: MISC_FEATURE
<222> LOCATION: (65)..(65)
<223> OTHER INFORMATION: X can be Ser or Arg
<220> FEATURE:
<221> NAME/KEY: MISC_FEATURE
<222> LOCATION: (72)..(72)
<223> OTHER INFORMATION: X can be Ala or Thr
<220> FEATURE:
<221> NAME/KEY: MISC_FEATURE
<222> LOCATION: (76)..(76)
<223> OTHER INFORMATION: X can be Ser or Asn
<220> FEATURE:
<221> NAME/KEY: MISC_FEATURE
<222> LOCATION: (83)..(83)
<223> OTHER INFORMATION: X can be Phe or Val
<220> FEATURE:
<221> NAME/KEY: MISC_FEATURE
<222> LOCATION: (85)..(85)
<223> OTHER INFORMATION: X can be Thr or Asn
<220> FEATURE:
<221> NAME/KEY: MISC_FEATURE
<222> LOCATION: (87)..(87)
<223> OTHER INFORMATION: X can be Tyr or Cys
<220> FEATURE:
<221> NAME/KEY: MISC_FEATURE
<222> LOCATION: (90)..(90)
<223> OTHER INFORMATION: X can be Gln or Lys
<220> FEATURE:
```

-continued

```
<221> NAME/KEY: MISC_FEATURE
<222> LOCATION: (91)..(91)
<223> OTHER INFORMATION: X can be Ala, Val or Tyr
<220> FEATURE:
<221> NAME/KEY: MISC_FEATURE
<222> LOCATION: (92)..(92)
<223> OTHER INFORMATION: X can be Asp or Asn
<220> FEATURE:
<221> NAME/KEY: MISC_FEATURE
<222> LOCATION: (94)..(94)
<223> OTHER INFORMATION: X can be Phe or Ala
<220> FEATURE:
<221> NAME/KEY: MISC_FEATURE
<222> LOCATION: (96)..(96)
<223> OTHER INFORMATION: X can be Trp, Gly or Phe
<220> FEATURE:
<221> NAME/KEY: MISC_FEATURE
<222> LOCATION: (100)..(100)
<223> OTHER INFORMATION: X can be Gln, Arg or Pro
<220> FEATURE:
<221> NAME/KEY: MISC_FEATURE
<222> LOCATION: (103)..(103)
<223> OTHER INFORMATION: X can be Lys or Asn
<220> FEATURE:
<221> NAME/KEY: MISC_FEATURE
<222> LOCATION: (105)..(105)
<223> OTHER INFORMATION: X can be Glu or Asp

<400> SEQUENCE: 56

Asp Ile Gln Met Thr Gln Ser Pro Ser Ser Xaa Xaa Ala Ser Xaa Gly
1               5                   10                  15

Asp Arg Val Thr Ile Thr Cys Arg Ala Ser Gln Xaa Xaa Xaa Xaa Xaa
            20                  25                  30

Leu Ala Trp Tyr Gln Xaa Lys Pro Gly Xaa Xaa Pro Xaa Xaa Leu Ile
        35                  40                  45

Xaa Xaa Xaa Ser Xaa Leu Xaa Xaa Gly Val Pro Xaa Arg Phe Ser Gly
50                  55                  60

Xaa Gly Ser Gly Thr Asp Phe Xaa Leu Thr Ile Xaa Ser Leu Gln Pro
65                  70                  75                  80

Glu Asp Xaa Ala Xaa Tyr Xaa Cys Gln Xaa Xaa Xaa Ser Xaa Pro Xaa
                85                  90                  95

Thr Phe Gly Xaa Gly Thr Xaa Val Xaa Ile Lys
            100                 105

<210> SEQ ID NO 57
<211> LENGTH: 107
<212> TYPE: PRT
<213> ORGANISM: Artificial
<220> FEATURE:
<223> OTHER INFORMATION: Light chain consensus
<220> FEATURE:
<221> NAME/KEY: MISC_FEATURE
<222> LOCATION: (2)..(2)
<223> OTHER INFORMATION: X can be Ile or Val
<220> FEATURE:
<221> NAME/KEY: MISC_FEATURE
<222> LOCATION: (22)..(22)
<223> OTHER INFORMATION: X can be Ser or Thr
<220> FEATURE:
<221> NAME/KEY: MISC_FEATURE
<222> LOCATION: (30)..(30)
<223> OTHER INFORMATION: X can be Ser, Asn or Thr
<220> FEATURE:
<221> NAME/KEY: MISC_FEATURE
<222> LOCATION: (31)..(31)
<223> OTHER INFORMATION: X can be Asn, Thr or Asp
<220> FEATURE:
<221> NAME/KEY: MISC_FEATURE
<222> LOCATION: (43)..(43)
<223> OTHER INFORMATION: X can be Ala or Val
<220> FEATURE:
<221> NAME/KEY: MISC_FEATURE
```

```
<222> LOCATION: (51)..(51)
<223> OTHER INFORMATION: X can be Ala or Thr
<220> FEATURE:
<221> NAME/KEY: MISC_FEATURE
<222> LOCATION: (56)..(56)
<223> OTHER INFORMATION: X can be Thr or Ala
<220> FEATURE:
<221> NAME/KEY: MISC_FEATURE
<222> LOCATION: (76)..(76)
<223> OTHER INFORMATION: X can be Asn or Ser
<220> FEATURE:
<221> NAME/KEY: MISC_FEATURE
<222> LOCATION: (77)..(77)
<223> OTHER INFORMATION: X can be Gly or Ser
<220> FEATURE:
<221> NAME/KEY: MISC_FEATURE
<222> LOCATION: (87)..(87)
<223> OTHER INFORMATION: X can be Phe or Tyr
<220> FEATURE:
<221> NAME/KEY: MISC_FEATURE
<222> LOCATION: (91)..(91)
<223> OTHER INFORMATION: X can be Phe or Tyr
<220> FEATURE:
<221> NAME/KEY: MISC_FEATURE
<222> LOCATION: (93)..(93)
<223> OTHER INFORMATION: X can be Asn or Ile
<220> FEATURE:
<221> NAME/KEY: MISC_FEATURE
<222> LOCATION: (96)..(96)
<223> OTHER INFORMATION: X can be Cys, Ser, Ile or Tyr
<220> FEATURE:
<221> NAME/KEY: MISC_FEATURE
<222> LOCATION: (97)..(97)
<223> OTHER INFORMATION: X can be Ser or Thr
<220> FEATURE:
<221> NAME/KEY: MISC_FEATURE
<222> LOCATION: (103)..(103)
<223> OTHER INFORMATION: X can be Lys, Arg or Asp

<400> SEQUENCE: 57

Asp Xaa Gln Met Thr Gln Ser Pro Ser Ser Leu Ser Ala Ser Val Gly
 1               5                  10                  15

Asp Arg Val Thr Ile Xaa Cys Gln Ala Ser Gln Asp Ile Xaa Xaa Tyr
             20                  25                  30

Leu Asn Trp Tyr Gln Gln Lys Pro Gly Lys Xaa Pro Lys Leu Leu Ile
         35                  40                  45

Tyr Asp Xaa Ser Asn Leu Glu Xaa Gly Val Pro Ser Arg Phe Ser Gly
     50                  55                  60

Ser Gly Ser Gly Thr Asp Phe Thr Phe Thr Ile Xaa Xaa Leu Gln Pro
 65                  70                  75                  80

Glu Asp Ile Ala Thr Tyr Xaa Cys Gln Gln Xaa Asp Xaa Leu Pro Xaa
                 85                  90                  95

Xaa Phe Gly Gln Gly Thr Xaa Leu Glu Ile Lys
            100                 105

<210> SEQ ID NO 58
<211> LENGTH: 121
<212> TYPE: PRT
<213> ORGANISM: Artificial
<220> FEATURE:
<223> OTHER INFORMATION: Heavy chain consensus
<220> FEATURE:
<221> NAME/KEY: MISC_FEATURE
<222> LOCATION: (10)..(10)
<223> OTHER INFORMATION: X can be Gly or Asp
<220> FEATURE:
<221> NAME/KEY: MISC_FEATURE
<222> LOCATION: (13)..(13)
<223> OTHER INFORMATION: X can be Lys or Glu
<220> FEATURE:
<221> NAME/KEY: MISC_FEATURE
<222> LOCATION: (23)..(23)
```

```
<223> OTHER INFORMATION: X can be Thr, Val or Ala
<220> FEATURE:
<221> NAME/KEY: MISC_FEATURE
<222> LOCATION: (30)..(30)
<223> OTHER INFORMATION: X can be Ser, Arg or Asn
<220> FEATURE:
<221> NAME/KEY: MISC_FEATURE
<222> LOCATION: (32)..(32)
<223> OTHER INFORMATION: X can be Tyr or Asn
<220> FEATURE:
<221> NAME/KEY: MISC_FEATURE
<222> LOCATION: (40)..(40)
<223> OTHER INFORMATION: X can be Ala or Thr
<220> FEATURE:
<221> NAME/KEY: MISC_FEATURE
<222> LOCATION: (48)..(48)
<223> OTHER INFORMATION: X can be Val, Ile or Leu
<220> FEATURE:
<221> NAME/KEY: MISC_FEATURE
<222> LOCATION: (53)..(53)
<223> OTHER INFORMATION: X can be Ser, Arg or Asn
<220> FEATURE:
<221> NAME/KEY: MISC_FEATURE
<222> LOCATION: (54)..(54)
<223> OTHER INFORMATION: X can be Ser, Thr, Val or Ile
<220> FEATURE:
<221> NAME/KEY: MISC_FEATURE
<222> LOCATION: (57)..(57)
<223> OTHER INFORMATION: X can be Ala, Thr or Val
<220> FEATURE:
<221> NAME/KEY: MISC_FEATURE
<222> LOCATION: (58)..(58)
<223> OTHER INFORMATION: X can be thr, Val, Met, Ile, Leu or Ser
<220> FEATURE:
<221> NAME/KEY: MISC_FEATURE
<222> LOCATION: (59)..(59)
<223> OTHER INFORMATION: X can be Tyr or His
<220> FEATURE:
<221> NAME/KEY: MISC_FEATURE
<222> LOCATION: (60)..(60)
<223> OTHER INFORMATION: X can be Tyr, Ser, Asp or Cys
<220> FEATURE:
<221> NAME/KEY: MISC_FEATURE
<222> LOCATION: (73)..(73)
<223> OTHER INFORMATION: X can be Asp, Val or His
<220> FEATURE:
<221> NAME/KEY: MISC_FEATURE
<222> LOCATION: (75)..(75)
<223> OTHER INFORMATION: X can be Ala or Pro
<220> FEATURE:
<221> NAME/KEY: MISC_FEATURE
<222> LOCATION: (76)..(76)
<223> OTHER INFORMATION: X can be Lys or Arg
<220> FEATURE:
<221> NAME/KEY: MISC_FEATURE
<222> LOCATION: (83)..(83)
<223> OTHER INFORMATION: X can be Met or Leu
<220> FEATURE:
<221> NAME/KEY: MISC_FEATURE
<222> LOCATION: (84)..(84)
<223> OTHER INFORMATION: X can be Asp, Asn or Ser
<220> FEATURE:
<221> NAME/KEY: MISC_FEATURE
<222> LOCATION: (89)..(89)
<223> OTHER INFORMATION: X can be Glu or Asp
<220> FEATURE:
<221> NAME/KEY: MISC_FEATURE
<222> LOCATION: (91)..(91)
<223> OTHER INFORMATION: X can be Thr or Ala
<220> FEATURE:
<221> NAME/KEY: MISC_FEATURE
<222> LOCATION: (94)..(94)
<223> OTHER INFORMATION: X can be Phe or Tyr
<220> FEATURE:
<221> NAME/KEY: MISC_FEATURE
<222> LOCATION: (97)..(97)
<223> OTHER INFORMATION: X can be Ala or Thr
<220> FEATURE:
<221> NAME/KEY: MISC_FEATURE
<222> LOCATION: (99)..(99)
```

```
<223> OTHER INFORMATION: X can be Glu or Asp
<220> FEATURE:
<221> NAME/KEY: MISC_FEATURE
<222> LOCATION: (100)..(100)
<223> OTHER INFORMATION: X can be His, Tyr, Phe or Arg
<220> FEATURE:
<221> NAME/KEY: MISC_FEATURE
<222> LOCATION: (103)..(103)
<223> OTHER INFORMATION: X can be Gly or Ala
<220> FEATURE:
<221> NAME/KEY: MISC_FEATURE
<222> LOCATION: (104)..(104)
<223> OTHER INFORMATION: X can be Tyr, Trp or Leu
<220> FEATURE:
<221> NAME/KEY: MISC_FEATURE
<222> LOCATION: (105)..(105)
<223> OTHER INFORMATION: X can be Asp or none
<220> FEATURE:
<221> NAME/KEY: MISC_FEATURE
<222> LOCATION: (106)..(106)
<223> OTHER INFORMATION: X can be Trp, Ala, Phe, Tyr, Ser, Val or Glu
<220> FEATURE:
<221> NAME/KEY: MISC_FEATURE
<222> LOCATION: (107)..(107)
<223> OTHER INFORMATION: X can be Tyr, Phe, Ser or Ala
<220> FEATURE:
<221> NAME/KEY: MISC_FEATURE
<222> LOCATION: (109)..(109)
<223> OTHER INFORMATION: X can be Asp or Glu
<220> FEATURE:
<221> NAME/KEY: MISC_FEATURE
<222> LOCATION: (110)..(110)
<223> OTHER INFORMATION: X can be Leu, Tyr, Ser or Ile
<220> FEATURE:
<221> NAME/KEY: MISC_FEATURE
<222> LOCATION: (113)..(113)
<223> OTHER INFORMATION: X can be Arg, Gln or His
<220> FEATURE:
<221> NAME/KEY: MISC_FEATURE
<222> LOCATION: (115)..(115)
<223> OTHER INFORMATION: X can be Ala or Thr
<220> FEATURE:
<221> NAME/KEY: MISC_FEATURE
<222> LOCATION: (116)..(116)
<223> OTHER INFORMATION: X can be Leu or Met

<400> SEQUENCE: 58

Gln Val Gln Leu Val Glu Ser Gly Gly Xaa Leu Val Xaa Pro Gly Gly
1               5                   10                  15

Ser Leu Arg Leu Ser Cys Xaa Ala Ser Gly Phe Thr Phe Xaa Asp Xaa
            20                  25                  30

Tyr Met Ser Trp Ile Arg Gln Xaa Pro Gly Lys Gly Leu Glu Trp Xaa
        35                  40                  45

Ser Tyr Ile Ser Xaa Xaa Gly Ser Xaa Xaa Xaa Xaa Ala Asp Ser Val
    50                  55                  60

Lys Gly Arg Phe Thr Ile Ser Arg Xaa Asn Xaa Xaa Asn Ser Leu Tyr
65                  70                  75                  80

Leu Gln Xaa Xaa Ser Leu Arg Ala Xaa Asp Xaa Ala Val Xaa Tyr Cys
            85                  90                  95

Xaa Arg Xaa Xaa Ser Ser Xaa Xaa Xaa Xaa Phe Xaa Xaa Trp Gly
            100                 105                 110

Xaa Gly Xaa Xaa Val Thr Val Ser Ser
        115                 120

<210> SEQ ID NO 59
<211> LENGTH: 118
<212> TYPE: PRT
<213> ORGANISM: Artificial
<220> FEATURE:
<223> OTHER INFORMATION: Heavy chain consensus
<220> FEATURE:
```

```
<221> NAME/KEY: MISC_FEATURE
<222> LOCATION: (29)..(29)
<223> OTHER INFORMATION: X can be Leu or Val
<220> FEATURE:
<221> NAME/KEY: MISC_FEATURE
<222> LOCATION: (30)..(30)
<223> OTHER INFORMATION: X can be Asn, Thr or Ser
<220> FEATURE:
<221> NAME/KEY: MISC_FEATURE
<222> LOCATION: (34)..(34)
<223> OTHER INFORMATION: X can be Met or Ile
<220> FEATURE:
<221> NAME/KEY: MISC_FEATURE
<222> LOCATION: (54)..(54)
<223> OTHER INFORMATION: X can be Ala or Gln
<220> FEATURE:
<221> NAME/KEY: MISC_FEATURE
<222> LOCATION: (55)..(55)
<223> OTHER INFORMATION: X can be Glu or Asp
<220> FEATURE:
<221> NAME/KEY: MISC_FEATURE
<222> LOCATION: (57)..(57)
<223> OTHER INFORMATION: X can be Lys or Glu
<220> FEATURE:
<221> NAME/KEY: MISC_FEATURE
<222> LOCATION: (58)..(58)
<223> OTHER INFORMATION: X can be Ile or Thr
<220> FEATURE:
<221> NAME/KEY: MISC_FEATURE
<222> LOCATION: (60)..(60)
<223> OTHER INFORMATION: X can be Ser or Tyr
<220> FEATURE:
<221> NAME/KEY: MISC_FEATURE
<222> LOCATION: (66)..(66)
<223> OTHER INFORMATION: X can be Asp or Gly
<220> FEATURE:
<221> NAME/KEY: MISC_FEATURE
<222> LOCATION: (72)..(72)
<223> OTHER INFORMATION: X can be Asp, Arg or Glu
<220> FEATURE:
<221> NAME/KEY: MISC_FEATURE
<222> LOCATION: (77)..(77)
<223> OTHER INFORMATION: X can be Asp or Ser
<220> FEATURE:
<221> NAME/KEY: MISC_FEATURE
<222> LOCATION: (79)..(79)
<223> OTHER INFORMATION: X can be Ala or Val
<220> FEATURE:
<221> NAME/KEY: MISC_FEATURE
<222> LOCATION: (84)..(84)
<223> OTHER INFORMATION: X can be Ser or Arg
<220> FEATURE:
<221> NAME/KEY: MISC_FEATURE
<222> LOCATION: (87)..(87)
<223> OTHER INFORMATION: X can be Arg or Lys
<220> FEATURE:
<221> NAME/KEY: MISC_FEATURE
<222> LOCATION: (91)..(91)
<223> OTHER INFORMATION: X can be Ser or Thr
<220> FEATURE:
<221> NAME/KEY: MISC_FEATURE
<222> LOCATION: (97)..(97)
<223> OTHER INFORMATION: X can be Ala or Thr
<220> FEATURE:
<221> NAME/KEY: MISC_FEATURE
<222> LOCATION: (98)..(98)
<223> OTHER INFORMATION: X can be Thr or Arg
<220> FEATURE:
<221> NAME/KEY: MISC_FEATURE
<222> LOCATION: (99)..(99)
<223> OTHER INFORMATION: X can be Leu, Glu or Gly
<220> FEATURE:
<221> NAME/KEY: MISC_FEATURE
<222> LOCATION: (100)..(100)
<223> OTHER INFORMATION: X can be Asp or Ser
<220> FEATURE:
<221> NAME/KEY: MISC_FEATURE
<222> LOCATION: (101)..(101)
<223> OTHER INFORMATION: X can be Phe or Ser
<220> FEATURE:
```

```
<221> NAME/KEY: MISC_FEATURE
<222> LOCATION: (103)..(103)
<223> OTHER INFORMATION: X can be Ser or Ala

<400> SEQUENCE: 59
```

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Xaa Xaa Asp Leu
            20                  25                  30

Ser Xaa His Trp Val Arg Gln Ala Pro Gly Lys Gly Leu Glu Trp Met
        35                  40                  45

Gly Gly Phe Asp Pro Xaa Xaa Gly Xaa Xaa Ile Xaa Ala Gln Lys Phe
    50                  55                  60

Gln Xaa Arg Val Thr Met Thr Xaa Asp Thr Ser Thr Xaa Thr Xaa Tyr
65              70                  75                  80

Met Glu Leu Xaa Ser Leu Xaa Ser Glu Asp Xaa Ala Val Tyr Tyr Cys
            85                  90                  95

Xaa Xaa Xaa Xaa Xaa Ser Xaa Trp Phe Asp Pro Trp Gly Gln Gly Thr
        100                 105                 110

Leu Val Thr Val Ser Ser
        115

```
<210> SEQ ID NO 60
<211> LENGTH: 125
<212> TYPE: PRT
<213> ORGANISM: Artificial
<220> FEATURE:
<223> OTHER INFORMATION: Heavy chain consensus
<220> FEATURE:
<221> NAME/KEY: MISC_FEATURE
<222> LOCATION: (13)..(13)
<223> OTHER INFORMATION: X can be Gln or Lys
<220> FEATURE:
<221> NAME/KEY: MISC_FEATURE
<222> LOCATION: (16)..(16)
<223> OTHER INFORMATION: X can be Gly or Arg
<220> FEATURE:
<221> NAME/KEY: MISC_FEATURE
<222> LOCATION: (89)..(89)
<223> OTHER INFORMATION: X can be Glu or Asp

<400> SEQUENCE: 60
```

Glu Val Gln Leu Val Glu Ser Gly Gly Gly Leu Val Xaa Pro Gly Xaa
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Ser Gly Lys Gly Leu Glu Trp Val
        35                  40                  45

Ala Asn Ile Lys Gln Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Xaa Asp Thr Ala Val Tyr Tyr Cys
            85                  90                  95

Ala Arg Glu Gly Gly Tyr Asp Trp Asn Tyr Ala Asp Tyr Tyr Gly Met
        100                 105                 110

Asp Val Trp Gly Gln Gly Thr Thr Val Thr Val Ser Ser
        115                 120                 125

```
<210> SEQ ID NO 61
<211> LENGTH: 123
<212> TYPE: PRT
```

<213> ORGANISM: Artificial
<220> FEATURE:
<223> OTHER INFORMATION: Heavy chain consensus
<220> FEATURE:
<221> NAME/KEY: MISC_FEATURE
<222> LOCATION: (13)..(13)
<223> OTHER INFORMATION: X can be Lys or Glu
<220> FEATURE:
<221> NAME/KEY: MISC_FEATURE
<222> LOCATION: (28)..(28)
<223> OTHER INFORMATION: X can be Ser or Ile
<220> FEATURE:
<221> NAME/KEY: MISC_FEATURE
<222> LOCATION: (31)..(31)
<223> OTHER INFORMATION: X can be Gly or Ser
<220> FEATURE:
<221> NAME/KEY: MISC_FEATURE
<222> LOCATION: (35)..(35)
<223> OTHER INFORMATION: X can be Gly or Ala
<220> FEATURE:
<221> NAME/KEY: MISC_FEATURE
<222> LOCATION: (40)..(40)
<223> OTHER INFORMATION: X can be Met or Leu
<220> FEATURE:
<221> NAME/KEY: MISC_FEATURE
<222> LOCATION: (52)..(52)
<223> OTHER INFORMATION: X can be Tyr or Asp
<220> FEATURE:
<221> NAME/KEY: MISC_FEATURE
<222> LOCATION: (54)..(54)
<223> OTHER INFORMATION: X can be Tyr or Asn
<220> FEATURE:
<221> NAME/KEY: MISC_FEATURE
<222> LOCATION: (77)..(77)
<223> OTHER INFORMATION: X can be Asn or His
<220> FEATURE:
<221> NAME/KEY: MISC_FEATURE
<222> LOCATION: (94)..(94)
<223> OTHER INFORMATION: X can be Phe or Tyr
<220> FEATURE:
<221> NAME/KEY: MISC_FEATURE
<222> LOCATION: (98)..(98)
<223> OTHER INFORMATION: X can be Ser or Thr
<220> FEATURE:
<221> NAME/KEY: MISC_FEATURE
<222> LOCATION: (105)..(105)
<223> OTHER INFORMATION: X can be Glu or Thr
<220> FEATURE:
<221> NAME/KEY: MISC_FEATURE
<222> LOCATION: (106)..(106)
<223> OTHER INFORMATION: X can be Phe or Leu
<220> FEATURE:
<221> NAME/KEY: MISC_FEATURE
<222> LOCATION: (109)..(109)
<223> OTHER INFORMATION: X can be Pro or Gly
<220> FEATURE:
<221> NAME/KEY: MISC_FEATURE
<222> LOCATION: (110)..(110)
<223> OTHER INFORMATION: X can be Leu or Phe
<220> FEATURE:
<221> NAME/KEY: MISC_FEATURE
<222> LOCATION: (111)..(111)
<223> OTHER INFORMATION: X can be Asn or Tyr

<400> SEQUENCE: 61

Glu Val Gln Leu Val Gln Ser Gly Ala Glu Val Lys Xaa Pro Gly Glu
1               5                   10                  15

Ser Leu Lys Ile Ser Cys Lys Gly Ser Gly Tyr Xaa Phe Thr Xaa Tyr
                20                  25                  30

Trp Ile Xaa Trp Val Arg Gln Xaa Pro Gly Lys Gly Leu Glu Trp Met
            35                  40                  45

Gly Ile Ile Xaa Pro Xaa Asp Ser Asp Thr Arg Tyr Ser Pro Ser Phe
        50                  55                  60

Gln Gly Gln Val Thr Ile Ser Ala Asp Lys Ser Ile Xaa Thr Ala Tyr
65                  70                  75                  80

```
Leu Gln Trp Ser Ser Leu Lys Ala Ser Asp Thr Ala Met Xaa Tyr Cys
                85                  90                  95
Ala Xaa His Arg Leu Trp Leu Gly Xaa Xaa Pro Gly Xaa Xaa Ile
            100                 105                 110
Trp Gly Gln Gly Thr Met Val Thr Val Ser Ser
            115                 120
```

```
<210> SEQ ID NO 62
<211> LENGTH: 8
<212> TYPE: PRT
<213> ORGANISM: Artificial
<220> FEATURE:
<223> OTHER INFORMATION: FLAG (registered trademark) Peptide

<400> SEQUENCE: 62

Asp Tyr Lys Asp Asp Asp Asp Lys
1               5
```

```
<210> SEQ ID NO 63
<211> LENGTH: 321
<212> TYPE: DNA
<213> ORGANISM: Homo sapiens

<400> SEQUENCE: 63
gacatccaga tgacccagtc tccatcttcc gtgtctgcat ctgtaggaga cagagtcacc    60
atcacttgtc gggcgagtca gggtattagc agctggttag cctggtatca acagaaacca   120
gggaaagccc ctaagctcct gatctatggt gcatccaatt tggaaagtgg ggtcccatca   180
aggttcagcg gcagtggatc tgggacagat ttcactctca ccatcagcag cctgcagcct   240
gaagattttg caaattacta ttgtcaacag gctaacagtt tcccgtggac gttcggccaa   300
gggaccaagg tggaaatcaa a                                              321
```

```
<210> SEQ ID NO 64
<211> LENGTH: 354
<212> TYPE: DNA
<213> ORGANISM: Homo sapiens

<400> SEQUENCE: 64
caggtccagc tggtacagtc tggggctgag gtgaagaagc ctggggcctc agtgaaggtc    60
tcctgcaagg tttccggata caccctcagt gatttatcca ccactgggt gcgacaggct    120 cctggaaaag ggcttgagtg gatgggaggt tttgatcctc aagatggtga acaatctac    180 gcacagaagt tccagggcag agtcaccatg accgaggaca catctacaga cacagcctac   240
atggagctga gcagcctgaa atctgaggac acggccgtgt attactgcgc aacggggagc   300
agctcgtcct ggttcgaccc ctggggccag ggaaccctgg tcaccgtctc tagt         354
```

```
<210> SEQ ID NO 65
<211> LENGTH: 324
<212> TYPE: DNA
<213> ORGANISM: Homo sapiens

<400> SEQUENCE: 65
gaaatagtga tgacgcagtc tccagccacc ctgtctgtgt ctcccgggga aagagccacc    60
ctctcctgca gggccagtca gagtgttagt agcaacttag tctggtatca gcagaaacct   120
ggccaggctc ccaggctcct catttatggt gcatccacca gggccactgg tatcccagcc   180
aggttcagtg gcagtgggtc tgggacagac ttcactctca ccatcagcag cctgcagtct   240
gaagattttg cagtttatta ctgtcagcaa tatgatgact ggcctccgct cactttcggc   300
```

```
ggagggacca cggtggagat caaa                                          324

<210> SEQ ID NO 66
<211> LENGTH: 360
<212> TYPE: DNA
<213> ORGANISM: Homo sapiens

<400> SEQUENCE: 66
caggtgcagc tggtggagtc tgggggaggc ttggtcaagc ctggagggtc cctgagactc    60
tcctgtgcag cctctggatt caccttcagt gactactaca tgagctggat ccgccaggct   120
ccagggaagg ggctggagtg gctttcatac attagtaata gtggtagtgc catgtactac   180
gcagactctg tgaagggccg attcaccatc tccaggaca acgccaggaa ctcactgtat    240
ctgcaaatga acagcctgag agccgaggac acggccgtgt actactgtgc gagagagtat   300
agcagtggct ggttcttctt tgagtcctgg ggccagggaa ccctggtcac cgtctctagt   360

<210> SEQ ID NO 67
<211> LENGTH: 321
<212> TYPE: DNA
<213> ORGANISM: Homo sapiens

<400> SEQUENCE: 67
gacatccaga tgacccagtc tccatcttcc gtgtttgcat ctgtaggaga cagagtcacc    60
atcacttgtc gggcgagtca gggtattagc agctggttag cctggtatca gcagaaacca   120
gggaaagccc ctaatctcct gatctatggt gcatccagtt tacaaaatgg ggtcccatta   180
aggttcagcg gcagtggatc tgggacagat ttcactctca ccatcagcag cctgcagcct   240
gaagattttg caacttacta ttgtcaacag gctaacagtt tcccgtggac gttcggccaa   300
gggaccaagg tggaaatcaa a                                             321

<210> SEQ ID NO 68
<211> LENGTH: 354
<212> TYPE: DNA
<213> ORGANISM: Homo sapiens

<400> SEQUENCE: 68
caggtccagc tggtacagtc tggggctgag gtgaagaagc ctggggcctc agtgaaggtc    60
tcctgcaagg tttccggata caccgtcact gatttatcca tgcactgggt gcgacaggct   120
cctggaaaag ggcttgagtg gatgggaggt tttgatcctc aagatggtga acaatctac    180 gcacagaagt tccagggcag agtcaccatg accgaggaca catctacaga cacagcctac   240
atggagctga aagcctgag atctgaggac acggccgtat attactgtac aacagaaagc   300
agctcggcct ggttcgaccc ctggggccag ggaaccctgg tcaccgtctc tagt         354

<210> SEQ ID NO 69
<211> LENGTH: 324
<212> TYPE: DNA
<213> ORGANISM: Homo sapiens

<400> SEQUENCE: 69
cgtacggtgg ctgcaccatc tgtcttcatc ttcccgccat ctgatgagca gttgaaatct    60
ggaactgcct ctgttgtgtg cctgctgaat aacttctatc ccagagaggc caaagtacag   120
tggaaggtgg ataacgccct ccaatcgggt aactcccagg agagtgtcac agagcaggac   180
agcaaggaca gcacctacag cctcagcagc accctgacgc tgagcaaagc agactacgag   240
aaacacaaag tctacgcctg cgaagtcacc catcagggcc tgagctcgcc cgtcacaaag   300
```
agcttcaaca ggggagagtg ttga                                          324

<210> SEQ ID NO 70
<211> LENGTH: 107
<212> TYPE: PRT
<213> ORGANISM: Homo sapiens

<400> SEQUENCE: 70

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 71
<211> LENGTH: 981
<212> TYPE: DNA
<213> ORGANISM: Homo sapiens

<400> SEQUENCE: 71
gcctccacca agggcccatc ggtcttcccc ctggcgccct gctccaggag cacctccgag    60
agcacagcgg ccctgggctg cctggtcaag gactacttcc ccgaaccggt gacggtgtcg   120
tggaactcag gcgctctgac cagcggcgtg cacaccttcc cagctgtcct acagtcctca   180
ggactctact ccctcagcag cgtggtgacc gtgccctcca gcaacttcgg cacccagacc   240
tacacctgca acgtagatca caagcccagc aacaccaagg tggacaagac agttgagcgc   300
aaatgttgtg tcgagtgccc accgtgccca gcaccacctg tggcaggacc gtcagtcttc   360
ctcttccccc caaaacccaa ggacaccctc atgatctccc ggacccctga ggtcacgtgc   420
gtggtggtgg acgtgagcca cgaagacccc gaggtccagt tcaactggta cgtggacggc   480
gtggaggtgc ataatgccaa gacaaagcca cgggaggagc agttcaacag cacgttccgt   540
gtggtcagcg tcctcaccgt tgtgcaccag gactggctga acggcaagga gtacaagtgc   600
aaggtctcca acaaaggcct cccagccccc atcgagaaaa ccatctccaa aaccaaaggg   660
cagccccgag aaccacaggt gtacaccctg cccccatccc gggaggagat gaccaagaac   720
caggtcagcc tgacctgcct ggtcaaaggc ttctacccca gcgacatcgc cgtggagtgg   780
gagagcaatg ggcagccgga gaacaactac aagaccacac ctcccatgct ggactccgac   840
ggctccttct tcctctacag caagctcacc gtggacaaga gcaggtggca gcaggggaac   900
gtcttctcat gctccgtgat gcatgaggct ctgcacaacc actacacgca gaagagcctc   960
tccctgtctc cgggtaaatg a                                             981

<210> SEQ ID NO 72
<211> LENGTH: 326
<212> TYPE: PRT
<213> ORGANISM: Homo sapiens -continued

```
<400> SEQUENCE: 72

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

ALPHA-4 BETA-7 HETERODIMER SPECIFIC ANTAGONIST ANTIBODY

CROSS-REFERENCE TO RELATED APPLICATIONS

This application claims the benefit under 35 U.S.C. 119(e) of U.S. patent application No. 61/162,154, filed Mar. 20, 2009 and U.S. patent application No. 61/306,829, filed Feb. 22, 2010, which are incorporated herein by reference.

REFERENCE TO THE SEQUENCE LISTING

The present application is being filed along with a Sequence Listing in electronic format. The Sequence Listing is provided as a file entitled A-1459-US-NP_Seq_Listing.txt, created Mar. 16, 2010, which is 84.0 KB in size. The information in the electronic format of the Sequence Listing is incorporated herein by reference in its entirety.

FIELD OF THE INVENTION

This application provides compositions and methods relating to alpha4beta7 heterodimer-specific antigen binding proteins.

BACKGROUND

Integrins are heterodimeric Type I transmembrane proteins formed of two subunits (one alpha subunit and one beta subunit), and mediate many different cell-cell and cell-extracellular matrix interactions. Functionally, integrins have been shown to be involved in diverse biological processes, including leukocyte migration and recirculation and the immune response. In mammals, there are 18 known alpha subunits and eight known beta subunits, which combine to form 24 distinct integrins. Ligand specificity is determined in large part by the particular combinations of alpha and beta subunits expressed, while affinity for ligand is modulated by integrin conformational changes and is divalent-cation dependent.

The ligands for integrins form a structurally diverse group that includes extracellular matrix proteins such as collagens, fibronection, vitronectin and laminins; counter-receptors such as the cellular adhesion molecules (for example, vascular cellular adhesion molecule or VCAM), and plasma proteins. Numerous pathogenic microorganisms also utilize integrins to initiate infection or as sites for toxin binding. The structurally diverse ligands share an exposed glutamic or aspartic acid residue, usually present in an extended, flexible loop, which is important for recognition by integrins.

The alpha4 integrins (alpha 4 partnered with either the beta1 or beta7 subunit) play an important role in the immune system. Alpha4beta1 is expressed on lymphocytes and myeloid cells; it appears to be the major binding partner for vascular cell adhesion molecule (VCAM). VCAM is ubiquitously expressed on vascular endothelium, is up regulated during inflammation, and binds alpha4beta7 as well as alpha4beta1 (albeit weakly to alpha4beta7). Though also detected on d peripheral T cells, B cells, NK cells and eosinphils, alpha4beta7 is most highly expressed on a subpopulation of CD4+CD45RA-memory T cells which has been shown to preferentially home to the gut. The primary ligand for the alpha4beta7 heterodimer is mucosal addressin cell adhesion molecule 1 (MAdCAM-1 or MAdCAM), which is expressed in gut endothelium.

In addition to pairing with the alpha4 chain, the beta7 subunit also partners with alphaE to form alphaEbeta7, which is primarily expressed on intraepithelial lymphocytes (IEL) in intestine, lung and genitourinary tract. AlphaEbeta7 is also expressed on dendritic cells in the gut. The alphaEbeta7 heterodimer binds to E-cadherin, which is expressed on epithelial cells. The IEL cells are thought to provide a mechanism for immunosurveillance within the epithelial compartment.

Antibodies that bind alpha4 and inhibit binding of alpha4beta1 to VCAM-1 and fibronection mapped to a 52-amino acid region of alpha4, between residues 152 and 203 (Schiffer et al., J. Biol. Chem. 270:14270; 1995). Tidswell et al. (J. Immuno 159:1497; 1997) identified domains of beta7 that are important in binding to MAdCAM-1, utilizing a panel of antibodies that bind beta7 in a mouse/human chimeric beta7 subunit approach. They found that six of seven antibodies that inhibited binding to MAdCAM-1 and E-cadherin mapped to a region comprising amino acids 176 through 250, which appears to have homology to the metal-ion dependent adhesion site (MIDAS) of other integrin subunits. One of the antibodies used by Tidswell et al. was an alpha4beta7 heterodimer specific antibody referred to as ACT-1.

The ACT-1 antibody was originally described by Lazarovitz et al. (J. Immunol. 133:1857; 1984) as an antibody developed by immunizing mice with human tetanus toxoid-specific T lymphocyte line from PBMC. Later it was shown that ACT-1 binds to the alpha4beta7 heterodimer specifically (Schweighoffer et al., J. Immunol. 151:717, 1993). While ACT-1 does not bind murine alpha4beta7, it does bind alpha4beta7 from least some non-human primate species, and has been shown to attenuate spontaneous colitis in captive cotton-top tamarins (Hesterberg et al., Gastroenterology 111: 1373; 1996)

ACT-1 has been humanized and evaluated as a human therapeutic in ulcerative colitis (Feagan et al., N Engl J. Med. 352:2499; 2005), and recently in Crohn's disease (Feagan et al, Clinical Gastroenterology and Hepatology, 6:1370, 2008). Humanized ACT-1, also known as vedolizumab, is described in WO 98/06248 and U.S. Pat. No. 7,147,85, as well as WO 07/061,679 and US 2007-0122404. Another humanized antibody, natalizumab (Tysabri®), has been used to treat Crohn's disease. Natalizumab is a humanized version of an alpha4-specific murine antibody. Vedolizumab has been shown to lead to a neutralizing anti-humanized antibody response in a portion of patients, and natalizumab has been associated with progressive multifocal leukoencephalopathy (PML), a neurological disorder that is associated with reactivation of prior infection with JC virus in immunocompromised individuals. Accordingly, there is a need for a therapeutic agent that ameliorates these disadvantages while disrupting the alpha4beta7/MAdCAM-1 pathway.

SUMMARY OF THE INVENTION

In one aspect, the present invention provides an isolated antigen binding protein that specifically binds to human alpha4beta7 (i.e., an alpha4beta7 heterodimer specific antigen binding protein). In another aspect of the invention, the antigen binding protein specifically binds to the alpha4beta7 of a non-human primate, a cynomologous monkey, a chimpanzee, a non-primate mammal, a rodent, a mouse, a rat, a hamster, a guinea pig, a cat, or a dog. In another embodiment, the isolated antigen binding protein comprises a human antibody; a chimeric antibody; a monoclonal antibody; a recombinant antibody; an antigen-binding antibody fragment; a single chain antibody; a diabody; a triabody; a tetrabody; a Fab fragment; a F(ab')$_2$ fragment; a domain antibody; an IgD antibody; an IgE antibody; an IgM antibody; an IgG1 antibody; an IgG2 antibody; an IgG3 antibody; an IgG4 antibody;

or an IgG4 antibody having at least one mutation in a hinge region that alleviates a tendency to form intra-H chain disulfide bond. In another aspect, the isolated antigen binding protein comprises a heavy chain constant region from one of the aforementioned antibodies; in another aspect, the constant region is a polypeptide comprising SEQ ID NO:72; a polypeptide at least 90% identical to SEQ ID NO:72; a polypeptide having an amino acid sequence as set forth in SEQ ID NO:72 from which one, two, three, four or five N-terminal and/or C-terminal amino acids have been removed; or one of the afore-mentioned polypeptides which incorporates one or more post-translational modifications. In one embodiment, the isolated antigen binding protein comprises a kappa light chain constant region, in another it comprises a lambda light chain region. In one embodiment, the light chain constant region is a polypeptide comprising SEQ ID NO:70; a polypeptide at least 90% identical to SEQ ID NO:70; a polypeptide having an amino acid sequence as set forth in SEQ ID NO:70 from which one, two, three, four or five N-terminal and/or C-terminal amino acids have been removed; or one of the afore-mentioned polypeptides which incorporates one or more post-translational modifications One embodiment of the present invention provides an alpha4beta7 heterodimer specific antigen binding protein having a heavy chain and a light chain, each of which comprise one or more complementarity determining regions, or CDRs. In another aspect of the invention, the heavy chain variable region comprises CDR1, CDR2 and CDR3 and a light chain variable region comprises CDR1, CDR2 and CDR3, wherein each respective CDR is selected from the group consisting of the light chain CDR1, CDR2 and CDR3 from SEQ ID NO:55, and the heavy chain CDR1, CDR2 and CDR3 from SEQ ID NO:58; the light chain CDR1, CDR2 and CDR3 from SEQ ID NO:56, and the heavy chain CDR1, CDR2 and CDR3 from SEQ ID NO:59; and the light chain CDR1, CDR2 and CDR3 from SEQ ID NO:57, and the heavy chain CDR1, CDR2 and CDR3 from SEQ ID NO:60.

In another aspect of the invention, the heavy chain variable region further comprises four framework regions (FRs) designated FR1, FR2, FR3 and FR4, and the light chain variable region further comprises four framework regions (FRs) designated FR1, FR2, FR3 and FR4. In one aspect, the FRs are selected from the same SEQ ID NO as the CDRs; in another, the FRs are selected from a different SEQ ID NO. In a further embodiment, the invention provides an alpha4beta7 heterodimer specific antigen binding protein wherein the light chain variable region comprises SEQ ID NO:55, and the heavy chain variable region comprises SEQ ID NO:58; the light chain variable region comprises SEQ ID NO:56, and the heavy chain variable region comprises SEQ ID NO:59; or the light chain variable region comprises SEQ ID NO:57, and the heavy chain variable region comprises SEQ ID NO:60.

In another aspect of the invention, the present invention provides an isolated alpha4beta7 heterodimer specific antigen binding protein, having a heavy chain and a light chain, each of which comprise one or more complementarity determining regions, or CDRs. In another aspect of the invention, the heavy chain variable region comprises CDR1, CDR2 and CDR3 and the light chain variable region comprises CDR1, CDR2 and CDR3. In one embodiment, the light chain CDRs are selected from the group consisting of a CDR1, CDR2 and CDR3 at least 90% identical to a CDR1, CDR2 and CDR3, respectively, of SEQ ID NO: 3; a CDR1, CDR2 and CDR3 at least 90% identical to a CDR1, CDR2 and CDR3, respectively, of SEQ ID NO: 5; a CDR1, CDR2 and CDR3 at least 90% identical to a CDR1, CDR2 and CDR3, respectively, of SEQ ID NO: 7; a CDR1, CDR2 and CDR3 at least 90% identical to a CDR1, CDR2 and CDR3, respectively, of SEQ ID NO: 22; and a CDR1, CDR2 and CDR3 at least 90% identical to a CDR1, CDR2 and CDR3, respectively, of SEQ ID NO: 24; and the heavy chain variable CDR1, CDR2 and CDR3 are from SEQ ID NO:58.

In another aspect of the invention, the heavy chain variable region further comprises four framework regions (FRs) designated FR1, FR2, FR3 and FR4, and the light chain variable region further comprises four framework regions (FRs) designated FR1, FR2, FR3 and FR4. In one aspect, the FRs are selected from the same SEQ ID NO as the CDRs; in another, the FRs are selected from a different SEQ ID NO. In a further embodiment, the invention provides an alpha4beta7 heterodimer specific antigen binding protein wherein the light chain variable region is selected from the group consisting of a light chain variable region at least 90% identical to SEQ ID NO:3; a light chain variable region at least 90% identical to SEQ ID NO:5; a light chain variable region at least 90% identical to SEQ ID NO:7; a light chain variable region at least 90% identical to SEQ ID NO:22; and a light chain variable region at least 90% identical to SEQ ID NO:24; and the heavy chain variable region comprises SEQ ID NO:58.

Another aspect of the invention provides an isolated, alpha4beta7 heterodimer specific antigen binding protein having a heavy chain variable region comprising CDR1, CDR2 and CDR3 and a light chain variable region comprising CDR1, CDR2 and CDR3, wherein the light chain CDR1, CDR2 and CDR3 are selected from the group consisting of a CDR1, CDR2 and CDR3 at least 90% identical to a CDR1, CDR2 and CDR3, respectively, of SEQ ID NO:12; a CDR1, CDR2 and CDR3 at least 90% identical to a CDR1, CDR2 and CDR3, respectively, of SEQ ID NO: 25; and a CDR1, CDR2 and CDR3 at least 90% identical to a CDR1, CDR2 and CDR3, respectively, of SEQ ID NO: 26; and the heavy chain CDR1, CDR2 and CDR3 are selected from the group consisting of a CDR1, CDR2 and CDR3 at least 90% identical to a CDR1, CDR2 and CDR3, respectively, of SEQ ID NO:41; and a CDR1, CDR2 and CDR3 at least 90% identical to a CDR1, CDR2 and CDR3, respectively, of SEQ ID NO:54. In one embodiment, the light chain variable region is selected from the group consisting of variable regions that are at least 90% identical to any one of SEQ ID NOs: 12, 25 and 26, and the heavy variable region is selected from the group consisting of variable regions that are at least 90% identical to any one of SEQ ID NOs:41 and 54. In another aspect of the invention, the heavy chain variable region further comprises four framework regions (FRs) designated FR1, FR2, FR3 and FR4, and the light chain variable region further comprises four framework regions (FRs) designated FR1, FR2, FR3 and FR4. In one aspect, the FRs are selected from the same SEQ ID NO as the CDRs; in another, the FRs are selected from a different SEQ ID NO.

In one embodiment, the invention provides an isolated, alpha4beta7 heterodimer specific antigen binding protein having a heavy chain variable region comprising CDR1, CDR2 and CDR3 and a light chain variable region comprising CDR1, CDR2 and CDR3, wherein each respective CDR is at least 90% identical to a CDR selected from the group consisting of a light chain CDR1, CDR2 and CDR3 from SEQ ID NO:10, and a heavy chain CDR1, CDR2 and CDR3 from SEQ ID NO:38; a light chain CDR1, CDR2 and CDR3 from SEQ ID NO:2, and a heavy chain CDR1, CDR2 and CDR3 from SEQ ID NO:30; a light chain CDR1, CDR2 and CDR3 from SEQ ID NO:20, and a heavy chain CDR1, CDR2 and CDR3 from SEQ ID NO:51; a light chain CDR1, CDR2 and CDR3 from SEQ ID NO:11, and a heavy chain CDR1, CDR2 and CDR3 from SEQ ID NO:39; a light chain CDR1, CDR2 and CDR3 from SEQ ID NO:13, and a heavy chain CDR1, CDR2 and CDR3 from SEQ ID NO:42; a light chain CDR1, CDR2 and CDR3 from SEQ ID NO:17, and a heavy chain CDR1, CDR2 and CDR3 from SEQ ID NO:46; a light chain CDR1, CDR2 and CDR3 from SEQ ID NO:8, and a heavy chain CDR1, CDR2 and CDR3 from SEQ ID NO:36; a light chain CDR1, CDR2 and CDR3 from SEQ ID NO:19, and a heavy chain CDR1, CDR2 and CDR3 from SEQ ID NO:49; a light chain CDR1, CDR2 and CDR3 from SEQ ID NO:18, and a heavy chain CDR1, CDR2 and CDR3 from SEQ ID NO:47; a light chain CDR1, CDR2 and CDR3 from SEQ ID NO:21, and a heavy chain CDR1, CDR2 and CDR3 from SEQ ID NO:52; a light chain CDR1, CDR2 and CDR3 from SEQ ID NO:3, and a heavy chain CDR1, CDR2 and CDR3 from SEQ ID NO:31; a light chain CDR1, CDR2 and CDR3 from SEQ ID NO:7, and a heavy chain CDR1, CDR2 and CDR3 from SEQ ID NO:35; a light chain CDR1, CDR2 and CDR3 from SEQ ID NO:6, and a heavy chain CDR1, CDR2 and CDR3 from SEQ ID NO:34; a light chain CDR1, CDR2 and CDR3 from SEQ ID NO:1, and a heavy chain CDR1, CDR2 and CDR3 from SEQ ID NO:29; a light chain CDR1, CDR2 and CDR3 from SEQ ID NO:22, and a heavy chain CDR1, CDR2 and CDR3 from SEQ ID NO:50; a light chain CDR1, CDR2 and CDR3 from SEQ ID NO:24, and a heavy chain CDR1, CDR2 and CDR3 from SEQ ID NO:40; a light chain CDR1, CDR2 and CDR3 from SEQ ID NO:9, and a heavy chain CDR1, CDR2 and CDR3 from SEQ ID NO:37; a light chain CDR1, CDR2 and CDR3 from SEQ ID NO:4, and a heavy chain CDR1, CDR2 and CDR3 from SEQ ID NO:32; a light chain CDR1, CDR2 and CDR3 from SEQ ID NO:28, and a heavy chain CDR1, CDR2 and CDR3 from SEQ ID NO:53; a light chain CDR1, CDR2 and CDR3 from SEQ ID NO:16, and a heavy chain CDR1, CDR2 and CDR3 from SEQ ID NO:45; a light chain CDR1, CDR2 and CDR3 from SEQ ID NO:15, and a heavy chain CDR1, CDR2 and CDR3 from SEQ ID NO:44; a light chain CDR1, CDR2 and CDR3 from SEQ ID NO:14, and a heavy chain CDR1, CDR2 and CDR3 from SEQ ID NO:43; a light chain CDR1, CDR2 and CDR3 from SEQ ID NO:27, and a heavy chain CDR1, CDR2 and CDR3 from SEQ ID NO:43; a light chain CDR1, CDR2 and CDR3 from SEQ ID NO:5, and a heavy chain CDR1, CDR2 and CDR3 from SEQ ID NO:33; a light chain CDR1, CDR2 and CDR3 from SEQ ID NO:12, and a heavy chain CDR1, CDR2 and CDR3 from SEQ ID NO:41; a light chain CDR1, CDR2 and CDR3 from SEQ ID NO:23, and a heavy chain CDR1, CDR2 and CDR3 from SEQ ID NO:48; a light chain CDR1, CDR2 and CDR3 from SEQ ID NO:25, and a heavy chain CDR1, CDR2 and CDR3 from SEQ ID NO:54; and a light chain CDR1, CDR2 and CDR3 from SEQ ID NO:26, and a heavy chain CDR1, CDR2 and CDR3 from SEQ ID NO:54. In another aspect, the heavy chain and light chain CDRs are identical to the respective CDRs of the recited SEQ ID NOs. In one embodiment of the invention, the heavy chain variable region further comprises four framework regions (FRs) designated FR1, FR2, FR3 and FR4, and the light chain variable region further comprises four framework regions (FRs) designated FR1, FR2, FR3 and FR4. In one aspect, the FRs are selected from the same SEQ ID NO as the CDRs; in another, the FRs are selected from a different SEQ ID NO.

In another embodiment, an alpha4beta7 heterodimer specific antigen binding protein comprises a light chain variable region and a heavy chain variable region, wherein the light chain variable region is at least 90% identical to SEQ ID NO:10, and the heavy chain variable region is at least 90% identical to SEQ ID NO:38; the light chain variable region is at least 90% identical to SEQ ID NO:2, and the heavy chain variable region is at least 90% identical to SEQ ID NO:30; the light chain variable region is at least 90% identical to SEQ ID NO:20, and the heavy chain variable region is at least 90% identical to SEQ ID NO:51; the light chain variable region is at least 90% identical to SEQ ID NO:11, and the heavy chain variable region is at least 90% identical to SEQ ID NO:39; the light chain variable region is at least 90% identical to SEQ ID NO:13, and the heavy chain variable region is at least 90% identical to SEQ ID NO:42; the light chain variable region is at least 90% identical to SEQ ID NO:17, and the heavy chain variable region is at least 90% identical to SEQ ID NO:46; the light chain variable region is at least 90% identical to SEQ ID NO:8, and the heavy chain variable region is at least 90% identical to SEQ ID NO:36; the light chain variable region is at least 90% identical to SEQ ID NO:19, and the heavy chain variable region is at least 90% identical to SEQ ID NO:49; the light chain variable region is at least 90% identical to SEQ ID NO:18, and the heavy chain variable region is at least 90% identical to SEQ ID NO:47; the light chain variable region is at least 90% identical to SEQ ID NO:21, and the heavy chain variable region is at least 90% identical to SEQ ID NO:52; the light chain variable region is at least 90% identical to SEQ ID NO:3, and the heavy chain variable region is at least 90% identical to SEQ ID NO:31; the light chain variable region is at least 90% identical to SEQ ID NO:7, and the heavy chain variable region is at least 90% identical to SEQ ID NO:35; the light chain variable region is at least 90% identical to SEQ ID NO:6, and the heavy chain variable region is at least 90% identical to SEQ ID NO:34; the light chain variable region is at least 90% identical to SEQ ID NO:1, and the heavy chain variable region is at least 90% identical to SEQ ID NO:29; the light chain variable region is at least 90% identical to SEQ ID NO:22, and the heavy chain variable region is at least 90% identical to SEQ ID NO:50; the light chain variable region is at least 90% identical to SEQ ID NO:24, and the heavy chain variable region is at least 90% identical to SEQ ID NO:40; the light chain variable region is at least 90% identical to SEQ ID NO:9, and the heavy chain variable region is at least 90% identical to SEQ ID NO:37; the light chain variable region is at least 90% identical to SEQ ID NO:4, and the heavy chain variable region is at least 90% identical to SEQ ID NO:32; the light chain variable region is at least 90% identical to SEQ ID NO:28, and the heavy chain variable region is at least 90% identical to SEQ ID NO:53; the light chain variable region is at least 90% identical to SEQ ID NO:16, and the heavy chain variable region is at least 90% identical to SEQ ID NO:45; the light chain variable region is at least 90% identical to SEQ ID NO:15, and the heavy chain variable region is at least 90% identical to SEQ ID NO:44; the light chain variable region is at least 90% identical to SEQ ID NO:14, and the heavy chain variable region is at least 90% identical to SEQ ID NO:43; the light chain variable region is at least 90% identical to SEQ ID NO:27, and the heavy chain variable region is at least 90% identical to SEQ ID NO:43; the light chain variable region is at least 90% identical to SEQ ID NO:5, and the heavy chain variable region is at least 90% identical to SEQ ID NO:33; the light chain variable region is at least 90% identical to SEQ ID NO:12, and the heavy chain variable region is at least 90% identical to SEQ ID NO:41; the light chain variable region is at least 90% identical to SEQ ID NO:23, and the heavy chain variable region is at least 90% identical to SEQ ID NO:48; the light chain variable region is at least 90% identical to SEQ ID NO:25, and the heavy chain variable region is at least 90% identical to SEQ ID NO:54; or the light chain variable region is at least 90% identical to SEQ ID NO:26, and the heavy chain variable region is at least 90% identical to SEQ ID NO:54. In another aspect, the heavy chain and light chain variable regions are identical to the respective variable regions of the recited SEQ ID NOs.

One aspect of the invention provides an isolated, alpha4beta7 heterodimer specific antigen binding protein having an EC50 of less than 35 ng/ml in a CD4+ memory T cell binding assay; another provides an isolated, alpha4beta7 heterodimer specific antigen binding which has an EC50 of less than 10 ng/ml in a CD4+ memory T cell binding assay. In another embodiment, the invention provides an isolated, alpha4beta7 heterodimer specific antigen binding protein having an IC50 in a MAdCAM competition assay of less than 30 ng/m; in another is provided an isolated, alpha4beta7 heterodimer specific antigen binding which has an IC50 of less than 10 ng/ml in a MAdCAM competition assay. One aspect of the invention provides an isolated, alpha4beta7 heterodimer specific antigen binding protein that binds an S250N mutant of alha4beta7.

In one aspect of the invention, the present invention provides nucleic acids encoding the aforementioned polypeptides. In another aspect of the invention the nucleic acid is a vector. In another embodiment of the invention, the invention provides host cells transformed or transfected with the inventive nucleic acids. In another aspect of the invention, there is provided a method of preparing a polypeptide comprising incubating the host cells under conditions promoting expression of the polypeptides and harvesting the polypeptides.

In another aspect, the present invention provides an isolated cell that secretes an antigen binding protein that binds alpha4beta7. In another embodiment, the cell is a hybridoma. In another embodiment, the present invention provides a method of making an antigen binding protein that specifically binds alpha4beta7 (i.e., human alpha4beta7), comprising incubating said isolated cell under conditions that allow it to express said antigen binding protein.

In one aspect, the present invention provides an isolated antigen binding protein that specifically binds to an alpha4beta7 heterodimer. In another embodiment, the isolated antigen binding protein, when bound to a human alpha4beta7, inhibits binding of alpha4beta7 to MAdCAM-1. Accordingly, one embodiment of the invention provides a method of inhibiting at least one activity of alpha4beta7, comprising contacting a cell expressing alpha4beta7 with an alpha4beta7 heterodimer-specific antigen binding protein such that the activity is partially or fully inhibited. In one aspect, such method is carried out in vivo. In one aspect of the invention, the isolated antigen binding protein inhibits adhesion of cells expressing alpha4beta7 to cells expressing MAdCAM-1. In yet another aspect of the invention, the isolated antigen binding protein inhibits trafficking of cells expressing alpha4beta7 to areas or tissues populated by cells expressing MAdCAM-1; in one example of such an embodiment, the isolated antigen binding proteins inhibit trafficking of lymphocytes to the gut.

In another aspect, the present invention provides a pharmaceutical composition comprising the antigen binding protein. In one embodiment, the present invention provides a method of treating a condition in a subject comprising administering the pharmaceutical composition to the subject, wherein the condition is treatable by reducing the activity (partially or fully) of alpha4beta7 in the subject. In another embodiment, the subject is a human being. In another embodiment, the condition is an inflammatory condition of the gastrointestinal system. Thus, there is provided a method of treating an individual afflicted with a condition characterized by inappropriate trafficking of cells expressing alpha4beta7 to tissues comprising cells expressing MAdCAM, comprising administering to the individual an alpha4beta7 heterodimer specific antigen binding protein in am amount sufficient to inhibit (partially or fully) the trafficking of cells expressing alpha4beta7 to tissues comprising cells expressing MAdCAM. In one embodiment, the condition is inflammatory bowel disease, for example, ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis. In another embodiment, the condition is s pancreatitis, insulin-dependent diabetes mellitus, mastitis, cholecystitis, cholangitis, pericholangitis, chronic bronchitis, chronic sinusitis, asthma or graft versus host disease.

In another embodiment, the method further comprises administering to the subject a second treatment. In another embodiment, the second treatment is administered to the subject before and/or simultaneously with and/or after the pharmaceutical composition is administered to the subject. In another embodiment, the second treatment comprises an anti-inflammatory agent. In another embodiment, the second pharmaceutical composition comprises an agent selected from the group consisting of non-steroidal anti-inflammatory drugs, steroids, and immunomodulating agents. In another embodiment, the method comprises administering to the subject a third treatment.

In another aspect, the present invention provides a method of increasing the longevity of a subject comprising administering to the subject the pharmaceutical composition. In another aspect, the present invention provides a method of decreasing alpha4beta7 activity in a subject in need thereof comprising administering to the subject the pharmaceutical composition. In another aspect, the present invention provides a method of decreasing alpha4beta7-mediated trafficking (for example, alpha4beta7mediated gut homing) in a subject in need thereof comprising administering to the subject the pharmaceutical composition.

DETAILED DESCRIPTION OF THE INVENTION

The present invention provides compositions, kits, and methods relating to molecules that bind to the integrin alpha4beta7 ("alpha4beta7"), including molecules that agonize or antagonize alpha4beta7, such as anti-alpha4beta7 antibodies, antibody fragments, and antibody derivatives, e.g., antagonistic anti-alpha4beta7 antibodies, antibody fragments, or antibody derivatives. Also provided are nucleic acids, and derivatives and fragments thereof, comprising a sequence of nucleotides that encodes all or a portion of a polypeptide that binds to alpha4beta7, e.g., a nucleic acid encoding all or part of an anti-alpha4beta7 antibody, antibody fragment, or antibody derivative, plasmids and vectors comprising such nucleic acids, and cells or cell lines comprising such nucleic acids and/or vectors and plasmids. The provided methods include, for example, methods of making, identifying, or isolating molecules that bind to alpha4beta7, such as anti-alpha4beta7 antibodies, methods of determining whether a molecule binds to alpha4beta7, methods of determining whether a molecule agonizes or antagonizes alpha4beta7, methods of making compositions, such as pharmaceutical compositions, comprising a molecule that binds to alpha4beta7, and methods for administering a molecule that binds alpha4beta7 to a subject, for example, methods for treating a condition mediated by alpha4beta7, and for agonizing or antagonizing a biological activity of alpha4beta7, in vivo or in vitro.

Polynucleotide and polypeptide sequences are indicated using standard one- or three-letter abbreviations. Unless otherwise indicated, each polypeptide sequence has amino terminus at the left and a carboxy terminus at the right; each single-stranded nucleic acid sequence, and the top strand of each double-stranded nucleic acid sequence has a 5' terminus at the left and a 3' terminus at the right. A particular polypeptide or polynucleotide sequence also can be described by explaining how it differs from a reference sequence.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, e.g., Sambrook et al. Molecular Cloning: A Laboratory Manual, 2d ed., Cold Spring Harbor Laboratory Press, Cold Spring Harbor, N.Y. (1989) and Ausubel et al., Current Protocols in Molecular Biology, Greene Publishing Associates (1992), and Harlow and Lane Antibodies: A Laboratory Manual Cold Spring Harbor Laboratory Press, Cold Spring Harbor, N.Y. (1990), which are incorporated herein by reference. Enzymatic reactions and purification techniques are performed according to manufacturer's specifications, as commonly accomplished in the art or as described herein. The terminology used in connection with, and the laboratory procedures and techniques of, analytical chemistry, synthetic organic chemistry, and medicinal and pharmaceutical chemistry described herein are those well known and commonly used in the art. Standard techniques can be used for chemical syntheses, chemical analyses, pharmaceutical preparation, formulation, and delivery, and treatment of patients.

The following terms, unless otherwise indicated, shall be understood to have the following meanings:

The term "isolated molecule" (where the molecule is, for example, a polypeptide, a polynucleotide, or an antibody) is a molecule that by virtue of its origin or source of derivation (1) is not associated with naturally associated components that accompany it in its native state, (2) is substantially free of other molecules from the same species (3) is expressed by a cell from a different species, or (4) does not occur in nature without human intervention. Thus, a molecule that is chemically synthesized, or synthesized in a cellular system different from the cell from which it naturally originates, will be "isolated" from its naturally associated components. A molecule also may be rendered substantially free of naturally associated components by isolation, using purification techniques well known in the art. Molecule purity or homogeneity may be assayed by a number of means well known in the art. For example, the purity of a polypeptide sample may be assayed using polyacrylamide gel electrophoresis and staining of the gel to visualize the polypeptide using techniques well known in the art. For certain purposes, higher resolution may be provided by using HPLC or other means well known in the art for purification.

The terms "alpha4beta7 inhibitor" and "alpha4beta7 antagonist" are used interchangeably. Each is a molecule that detectably inhibits at least one function of alpha4beta7. Conversely, an "alpha4beta7 agonist" is a molecule that detectably increases at least one function of alpha4beta7. The inhibition caused by an alpha4beta7 inhibitor need not be complete so long as it is detectable, for example by using an assay. Any assay of a function of alpha4beta7 can be used, examples of which are provided herein. Examples of functions of alpha4beta7 that can be inhibited by an alpha4beta7 inhibitor (or increased by an alpha4beta7 agonist) include ligand binding (i.e., binding to MAdCAM-1), adhesion to ligand-expressing cells, trafficking to a particular compartment such as the gut, release of cytokines, chemokines and other mediators, enhancing or exacerbating inflammatory response and tissue damage, and so on. Examples of types of alpha4beta7 inhibitors and alpha4beta7 agonists include, but are not limited to, alpha4beta7 binding polypeptides such as antigen binding proteins (e.g., alpha4beta7 antigen binding proteins), antibodies, antibody fragments, and antibody derivatives.

The terms "peptide," "polypeptide" and "protein" each refers to a molecule comprising two or more amino acid residues joined to each other by peptide bonds. These terms encompass, e.g., native and artificial proteins, protein fragments and polypeptide analogs (such as muteins, variants, and fusion proteins) of a protein sequence as well as post-translationally, or otherwise covalently or noncovalently, modified proteins. A peptide, polypeptide, or protein may be monomeric or polymeric.

The term "polypeptide fragment" as used herein refers to a polypeptide that has an amino-terminal and/or carboxy-terminal deletion as compared to a corresponding full-length protein. Fragments can be, for example, at least 5, 6, 7, 8, 9, 10, 11, 12, 13, 14, 15, 20, 50, 70, 80, 90, 100, 150 or 200 amino acids in length. Fragments can also be, for example, at most 1,000, 750, 500, 250, 200, 175, 150, 125, 100, 90, 80, 70, 60, 50, 40, 30, 20, 15, 14, 13, 12, 11, or 10 amino acids in length. Fragments can also result from proteolytic (or other) processing, which, for example, results in variation in the amino and/or carboxy terminus of from one to five amino acids from that predicted. A fragment can further comprise, at either or both of its ends, one or more additional amino acids, for example, a sequence of amino acids from a different naturally-occurring protein (e.g., an Fc or leucine zipper domain) or an artificial amino acid sequence (e.g., an artificial linker sequence or a tag protein).

Polypeptides of the invention include polypeptides that have been modified in any way and for any reason, for example, to: (1) reduce susceptibility to proteolysis, (2) reduce susceptibility to oxidation, (3) alter binding affinity for forming protein complexes, (4) alter binding affinities, and (4) confer or modify other physicochemical or functional properties. Analogs include muteins of a polypeptide. For example, single or multiple amino acid substitutions (e.g., conservative amino acid substitutions) may be made in the naturally occurring sequence (e.g., in the portion of the polypeptide outside the domain(s) forming intermolecular contacts). Consensus sequences can be used to select amino acid residues for substitution; those of skill in the art recognize that additional amino acid residues may also be substituted.

A "conservative amino acid substitution" is one that does not substantially change the structural characteristics of the parent sequence (e.g., a replacement amino acid should not tend to break a helix that occurs in the parent sequence, or disrupt other types of secondary structure that characterize the parent sequence or are necessary for its functionality). Examples of art-recognized polypeptide secondary and tertiary structures are described in Proteins, Structures and Molecular Principles (Creighton, Ed., W.H. Freeman and Company, New York (1984)); Introduction to Protein Structure (C. Branden and J. Tooze, eds., Garland Publishing, New York, N.Y. (1991)); and Thornton et al. Nature 354:105 (1991), which are each incorporated herein by reference.

The present invention also provides non-peptide analogs of alpha4beta7 binding polypeptides. Non-peptide analogs are commonly used in the pharmaceutical industry as drugs with properties analogous to those of the template peptide. These types of non-peptide compound are termed "peptide mimetics" or "peptidomimetics," see, for example, Fauchere, J. Adv. Drug Res. 15:29 (1986); Veber and Freidinger TINS p. 392 (1985); and Evans et al. J. Med. Chem. 30:1229 (1987), which are incorporated herein by reference. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a desired biochemical property or pharmacological activity), such as a human antibody, but have one or more peptide linkages optionally replaced by a linkage selected from the group consisting of: —CH$_2$NH—, —CH$_2$S—, —CH$_2$—CH$_2$—, —CH=CH-(cis and trans), —COCH$_2$—, —CH(OH)CH$_2$—, and —CH$_2$SO—, by methods well known in the art. Systematic substitution of one or more amino acids of a consensus sequence with a D-amino acid of the same type (e.g., D-lysine in place of L-lysine) may also be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992), incorporated herein by reference), for example, by adding internal cysteine residues capable of forming intramolecular disulfide bridges which cyclize the peptide.

A "variant" of a polypeptide (e.g., an antibody) comprises an amino acid sequence wherein one or more amino acid residues are inserted into, deleted from and/or substituted into the amino acid sequence relative to another polypeptide sequence. Variants of the invention include fusion proteins.

A "derivative" of a polypeptide is a polypeptide (e.g., an antibody) that has been chemically modified, e.g., via conjugation to another chemical moiety (such as, for example, polyethylene glycol or albumin, e.g., human serum albumin), phosphorylation, and/or glycosylation. Unless otherwise indicated, the term "antibody" includes, in addition to antibodies comprising two full-length heavy chains and two full-length light chains, derivatives, variants, fragments, and muteins thereof, examples of which are described below.

An "antigen binding protein" is a protein comprising a portion that binds to an antigen and, optionally, a scaffold or framework portion that allows the antigen binding portion to adopt a conformation that promotes binding of the antigen binding protein to the antigen. Examples of antigen binding proteins include antibodies, antibody fragments (e.g., an antigen binding portion of an antibody), antibody derivatives, and antibody analogs. The antigen binding protein can comprise, for example, an alternative protein scaffold or artificial scaffold with grafted CDRs or CDR derivatives. Such scaffolds include, but are not limited to, antibody-derived scaffolds comprising mutations introduced to, for example, stabilize the three-dimensional structure of the antigen binding protein as well as wholly synthetic scaffolds comprising, for example, a biocompatible polymer. See, for example, Korndorfer et al., 2003, Proteins: Structure, Function, and Bioinformatics, Volume 53, Issue 1:121-129; Roque et al., 2004, Biotechnol. Prog. 20:639-654. In addition, peptide antibody mimetics ("PAMs") can be used, as well as scaffolds based on antibody mimetics utilizing fibronection components as a scaffold.

An antigen binding protein can have, for example, the structure of a naturally occurring immunoglobulin. An "immunoglobulin" is a tetrameric molecule. In a naturally occurring immunoglobulin, each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa or lambda light chains. Heavy chains are classified as mu, delta, gamma, alpha, or epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

The variable regions of naturally occurring immunoglobulin chains exhibit the same general structure of relatively conserved framework regions (FR) joined by three hypervariable regions, also called complementarity determining regions or CDRs. From N-terminus to C-terminus, both light and heavy chains comprise the domains FR1, CDR1, FR2, CDR2, FR3, CDR3 and FR4. The assignment of amino acids to each domain is in accordance with the definitions of Kabat et al. in *Sequences of Proteins of Immunological Interest*, 5$^{th}$ Ed., US Dept. of Health and Human Services, PHS, NIH, NIH Publication no. 91-3242, 1991. Other numbering systems for the amino acids in immunoglobulin chains include IMGT® (the international ImMunoGeneTics information system; Lefranc et al, *Dev. Comp. Immunol.* 29:185-203; 2005) and AHo (Honegger and Pluckthun, *J. Mol. Biol.* 309(3):657-670; 2001).

Antibodies can be obtained from sources such as serum or plasma that contain immunoglobulins having varied antigenic specificity. If such antibodies are subjected to affinity purification, they can be enriched for a particular antigenic specificity. Such enriched preparations of antibodies usually are made of less than about 10% antibody having specific binding activity for the particular antigen. Subjecting these preparations to several rounds of affinity purification can increase the proportion of antibody having specific binding activity for the antigen. Antibodies prepared in this manner are often referred to as "monospecific." Monospecific antibody preparations can be made up of about 10%, 20%, 30%, 40%, 50%, 60%, 70%, 75%, 80%, 85%, 90%, 95%, 97%, 99%, or 99.9% antibody having specific binding activity for the particular antigen.

An "antibody" refers to an intact immunoglobulin or to an antigen binding portion thereof that competes with the intact antibody for specific binding, unless otherwise specified. Antigen binding portions may be produced by recombinant DNA techniques or by enzymatic or chemical cleavage of intact antibodies. Antigen binding portions include, inter alia, Fab, Fab', F(ab')$_2$, Fv, domain antibodies (dAbs), and complementarity determining region (CDR) fragments, variable region fragments, single-chain antibodies (scFv), chimeric antibodies, diabodies, triabodies, tetrabodies, and polypeptides that contain at least a portion of an immunoglobulin that is sufficient to confer specific antigen binding to the polypeptide.

A Fab fragment is a monovalent fragment having the $V_L$, $V_H$, $C_L$ and $C_H1$ domains; a $F(ab')_2$ fragment is a bivalent fragment having two Fab fragments linked by a disulfide bridge at the hinge region; a Fd fragment has the $V_H$ and $C_H1$ domains; an Fv fragment has the $V_L$ and $V_H$ domains of a single arm of an antibody; and a dAb fragment has a $V_H$ domain, a $V_L$ domain, or an antigen-binding fragment of a $V_H$ or $V_L$ domain (U.S. Pat. Nos. 6,846,634, 6,696,245, US App. Pub. No. 05/0202512, 04/0202995, 04/0038291, 04/0009507, 03/0039958, Ward et al., Nature 341:544-546, 1989).

A single-chain antibody (scFv) is an antibody in which a $V_L$ and a $V_H$ region are joined via a linker (e.g., a synthetic sequence of amino acid residues) to form a continuous protein chain wherein the linker is long enough to allow the protein chain to fold back on itself and form a monovalent antigen binding site (see, e.g., Bird et al., 1988, Science 242:423-26 and Huston et al., 1988, Proc. Natl. Acad. Sci. USA 85:5879-83). Diabodies are bivalent antibodies comprising two polypeptide chains, wherein each polypeptide chain comprises $V_H$ and $V_L$ domains joined by a linker that is too short to allow for pairing between two domains on the same chain, thus allowing each domain to pair with a complementary domain on another polypeptide chain (see, e.g., Holliger et al., 1993, Proc. Natl. Acad. Sci. USA 90:6444-48, and Poljak et al., 1994, Structure 2:1121-23). If the two polypeptide chains of a diabody are identical, then a diabody resulting from their pairing will have two identical antigen binding sites. Polypeptide chains having different sequences can be used to make a diabody with two different antigen binding sites. Similarly, triabodies and tetrabodies are antibodies comprising three and four polypeptide chains, respectively, and forming three and four antigen binding sites, respectively, which can be the same or different.

Complementarity determining regions (CDRs) and framework regions (FR) of a given antibody may be identified using the system described by Kabat et al. supra; Lefranc et al., supra and/or Honegger and Pluckthun, supra. One or more CDRs may be incorporated into a molecule either covalently or noncovalently to make it an antigen binding protein. An antigen binding protein may incorporate the CDR(s) as part of a larger polypeptide chain, may covalently link the CDR(s) to another polypeptide chain, or may incorporate the CDR(s) noncovalently. The CDRs permit the antigen binding protein to specifically bind to a particular antigen of interest.

An antigen binding protein may have one or more binding sites. If there is more than one binding site, the binding sites may be identical to one another or may be different. For example, a naturally occurring human immunoglobulin typically has two identical binding sites, while a "bispecific" or "bifunctional" antibody has two different binding sites.

The term "human antibody" includes all antibodies that have one or more variable and constant regions derived from human immunoglobulin sequences. In one embodiment, all of the variable and constant domains are derived from human immunoglobulin sequences (a fully human antibody). These antibodies may be prepared in a variety of ways, examples of which are described below, including through the immunization with an antigen of interest of a mouse that is genetically modified to express antibodies derived from human heavy and/or light chain-encoding genes.

A humanized antibody has a sequence that differs from the sequence of an antibody derived from a non-human species by one or more amino acid substitutions, deletions, and/or additions, such that the humanized antibody is less likely to induce an immune response, and/or induces a less severe immune response, as compared to the non-human species antibody, when it is administered to a human subject. In one embodiment, certain amino acids in the framework and constant domains of the heavy and/or light chains of the non-human species antibody are mutated to produce the humanized antibody. In another embodiment, the constant domain(s) from a human antibody are fused to the variable domain(s) of a non-human species. In another embodiment, one or more amino acid residues in one or more CDR sequences of a non-human antibody are changed to reduce the likely immunogenicity of the non-human antibody when it is administered to a human subject, wherein the changed amino acid residues either are not critical for immunospecific binding of the antibody to its antigen, or the changes to the amino acid sequence that are made are conservative changes, such that the binding of the humanized antibody to the antigen is not significantly worse than the binding of the non-human antibody to the antigen. Examples of how to make humanized antibodies may be found in U.S. Pat. Nos. 6,054,297, 5,886, 152 and 5,877,293.

The term "chimeric antibody" refers to an antibody that contains one or more regions from one antibody and one or more regions from one or more other antibodies. In one embodiment, one or more of the CDRs are derived from a human anti-alpha4beta7 antibody. In another embodiment, all of the CDRs are derived from a human anti-alpha4beta7 antibody. In another embodiment, the CDRs from more than one human anti-alpha4beta7 antibodies are mixed and matched in a chimeric antibody. For instance, a chimeric antibody may comprise a CDR1 from the light chain of a first human anti-alpha4beta7 antibody, a CDR2 and a CDR3 from the light chain of a second human anti-alpha4beta7 antibody, and the CDRs from the heavy chain from a third anti-alpha4beta7 antibody. Other combinations are possible and are included within the embodiments of the invention.

Further, the framework regions may be derived from one of the same anti-alpha4beta7 antibodies, from one or more different antibodies, such as a human antibody, or from a humanized antibody. In one example of a chimeric antibody, a portion of the heavy and/or light chain is identical with, homologous to, or derived from an antibody from a particular species or belonging to a particular antibody class or subclass, while the remainder of the chain(s) is/are identical with, homologous to, or derived from an antibody (-ies) from another species or belonging to another antibody class or subclass. Also included are fragments of such antibodies that exhibit the desired biological activity (i.e., the ability to specifically bind alpha4beta7). See, e.g., U.S. Pat. No. 4,816,567 and Morrison, 1985, Science 229:1202-07.

A "neutralizing antibody" or an "inhibitory antibody" is an antibody that inhibits the interaction of alpha4beta7 with MAdCAM-1 when an excess of the anti-alpha4beta7 antibody reduces the amount of interaction by at least about 20% using an assay such as those described herein in the Examples. In various embodiments, the antigen binding protein reduces the interaction of alpha4beta7 with MAdCAM-1 alpha4beta7 by at least 30%, 40%, 50%, 60%, 70%, 75%, 80%, 85%, 90%, 95%, 97%, 99%, and 99.9%.

Fragments or analogs of antibodies can be readily prepared by those of ordinary skill in the art following the teachings of this specification and using techniques well-known in the art Amino- and carboxy-termini of fragments or analogs occur near boundaries of functional domains. Structural and functional domains can be identified by comparison of the nucleotide and/or amino acid sequence data to public or proprietary sequence databases. Computerized comparison methods can be used to identify sequence motifs or predicted protein conformation domains that occur in other proteins of known structure and/or function. Methods to identify protein sequences that fold into a known three-dimensional structure are known. See, e.g., Bowie et al., 1991, Science 253:164.

A "CDR grafted antibody" is an antibody comprising one or more CDRs derived from an antibody of a particular species or isotype and the framework of another antibody of the same or different species or isotype.

A "multi-specific antibody" is an antibody that recognizes more than one epitope on one or more antigens. A subclass of this type of antibody is a "bi-specific antibody" which recognizes two distinct epitopes on the same or different antigens.

An antigen binding protein "specifically binds" to an antigen (e.g., human alpha4beta7) if it binds to the antigen with a dissociation constant of 1 nanomolar or less. As used herein, an antigen binding protein is "heterodimer specific" if it binds to a first heterodimeric integrin but not to other integrins that share one chain with the first integrin. For example, an antibody that is alpha4beta7 heterodimer specific will bind to alpha4beta7 but not to alpha4beta1 or alphaEbeta7.

Integrins are known to adapt different conformations, depending on the activation state of the cell(s) expressing them and on the presence or absence of certain metal ions. An integrin in "active" conformation binds to its cognate ligand with higher affinity than the same integrin in "inactive" conformation. An antigen binding protein may bind to an integrin in only its active conformation, in only its inactive conformation, or in both or either conformations. For example, an alpha4beta7 heterodimer specific antigen binding protein may bind alpha4beta7 in the presence or absence of the divalent cation manganese$^{2+}$ (Mn$^{2+}$), indicating that the antigen binding protein binds both active and inactive alpah4beta7.

An "antigen binding domain," "antigen binding region," or "antigen binding site" is a portion of an antigen binding protein that contains amino acid residues (or other moieties) that interact with an antigen and contribute to the antigen binding protein's specificity and affinity for the antigen. For an antibody that specifically binds to its antigen, this will include at least part of at least one of its CDR domains.

An "epitope" is the portion of a molecule that is bound by an antigen binding protein (e.g., by an antibody). An epitope can comprise non-contiguous portions of the molecule (e.g., in a polypeptide, amino acid residues that are not contiguous in the polypeptide's primary sequence but that, in the context of the polypeptide's tertiary and quaternary structure, are near enough to each other to be bound by an antigen binding protein).

The "percent identity" of two polynucleotide or two polypeptide sequences is determined by comparing the sequences using the GAP computer program (a part of the GCG Wisconsin Package, version 10.3 (Accelrys, San Diego, Calif.)) using its default parameters.

The terms "polynucleotide," "oligonucleotide" and "nucleic acid" are used interchangeably throughout and include DNA molecules (e.g., cDNA or genomic DNA), RNA molecules (e.g., mRNA), analogs of the DNA or RNA generated using nucleotide analogs (e.g., peptide nucleic acids and non-naturally occurring nucleotide analogs), and hybrids thereof. The nucleic acid molecule can be single-stranded or double-stranded. In one embodiment, the nucleic acid molecules of the invention comprise a contiguous open reading frame encoding an antibody, or a fragment, derivative, mutein, or variant thereof, of the invention.

Two single-stranded polynucleotides are "the complement" of each other if their sequences can be aligned in an anti-parallel orientation such that every nucleotide in one polynucleotide is opposite its complementary nucleotide in the other polynucleotide, without the introduction of gaps, and without unpaired nucleotides at the 5' or the 3' end of either sequence. A polynucleotide is "complementary" to another polynucleotide if the two polynucleotides can hybridize to one another under moderately stringent conditions. Thus, a polynucleotide can be complementary to another polynucleotide without being its complement.

A "vector" is a nucleic acid that can be used to introduce another nucleic acid linked to it into a cell. One type of vector is a "plasmid," which refers to a linear or circular double stranded DNA molecule into which additional nucleic acid segments can be ligated. Another type of vector is a viral vector (e.g., replication defective retroviruses, adenoviruses and adeno-associated viruses), wherein additional DNA segments can be introduced into the viral genome. Certain vectors are capable of autonomous replication in a host cell into which they are introduced (e.g., bacterial vectors comprising a bacterial origin of replication and episomal mammalian vectors). Other vectors (e.g., non-episomal mammalian vectors) are integrated into the genome of a host cell upon introduction into the host cell, and thereby are replicated along with the host genome. An "expression vector" is a type of vector that can direct the expression of a chosen polynucleotide.

A nucleotide sequence is "operably linked" to a regulatory sequence if the regulatory sequence affects the expression (e.g., the level, timing, or location of expression) of the nucleotide sequence. A "regulatory sequence" is a nucleic acid that affects the expression (e.g., the level, timing, or location of expression) of a nucleic acid to which it is operably linked. The regulatory sequence can, for example, exert its effects directly on the regulated nucleic acid, or through the action of one or more other molecules (e.g., polypeptides that bind to the regulatory sequence and/or the nucleic acid). Examples of regulatory sequences include promoters, enhancers and other expression control elements (e.g., polyadenylation signals). Further examples of regulatory sequences are described in, for example, Goeddel, 1990, Gene Expression Technology: Methods in Enzymology 185, Academic Press, San Diego, Calif. and Baron et al., 1995, Nucleic Acids Res. 23:3605-06.

A "host cell" is a cell that can be used to express a nucleic acid, e.g., a nucleic acid of the invention. A host cell can be a prokaryote, for example, E. coli, or it can be a eukaryote, for example, a single-celled eukaryote (e.g., a yeast or other fungus), a plant cell (e.g., a tobacco or tomato plant cell), an animal cell (e.g., a human cell, a monkey cell, a hamster cell, a rat cell, a mouse cell, or an insect cell) or a hybridoma. Examples of host cells include the COS-7 line of monkey kidney cells (ATCC CRL 1651) (see Gluzman et al., 1981, Cell 23:175), L cells, C127 cells, 3T3 cells (ATCC CCL 163), Chinese hamster ovary (CHO) cells or their derivatives such as Veggie CHO and related cell lines which grow in serum-free media (see Rasmussen et al., 1998, Cytotechnology 28:31) or CHO strain DX-B11, which is deficient in DHFR (see Urlaub et al., 1980, Proc. Natl. Acad. Sci. USA 77:4216-20), HeLa cells, BHK (ATCC CRL 10) cell lines, the CV1/EBNA cell line derived from the African green monkey kidney cell line CV1 (ATCC CCL 70) (see McMahan et al., 1991, EMBO J. 10:2821), human embryonic kidney cells such as 293, 293 EBNA or MSR 293, human epidermal A431 cells, human Colo205 cells, other transformed primate cell lines, normal diploid cells, cell strains derived from in vitro culture of primary tissue, primary explants, HL-60, U937, HaK or Jurkat cells. Typically, a host cell is a cultured cell that can be transformed or transfected with a polypeptide-encoding nucleic acid, which can then be expressed in the host cell. The phrase "recombinant host cell" can be used to denote a host cell that has been transformed or transfected with a nucleic acid to be expressed. A host cell also can be a cell that comprises the nucleic acid but does not express it at a desired level unless a regulatory sequence is introduced into the host cell such that it becomes operably linked with the nucleic acid. It is understood that the term host cell refers not only to the particular subject cell but also to the progeny or potential progeny of such a cell. Because certain modifications may occur in succeeding generations due to, e.g., mutation or environmental influence, such progeny may not, in fact, be identical to the parent cell, but are still included within the scope of the term as used herein.

Antigen Binding Proteins

In one aspect, the present invention provides antigen binding proteins (e.g., antibodies, antibody fragments, antibody derivatives, antibody muteins, and antibody variants) that bind to alpha4beta7, e.g., human alpha4beta7.

Antigen binding proteins in accordance with the present invention include antigen binding proteins that inhibit a biological activity of alpha4beta7. Examples of such biological activities include binding of alpha4beta7 to MAdCAM-1, and adhesion between cells expressing alpha4beta7 and those expressing MAdCAM-1. Other biological activities include those mediated by alpha4beta7 in vivo, such as trafficking or homing; in particular, alpha4beta7 is involved in the trafficking of lymphocytes to the gut, Increased MAdCAM-1 expression in the inflamed gut enhances recruitment of alpha4beta7 expressing lymphocytes to the gut, where aberrant lymphocyte activation augments inflammatory response and tissue damage.

Different antigen binding proteins may bind to different domains or epitopes of alpha4beta7 or act by different mechanisms of action. Examples include but are not limited to antigen binding proteins that interfere with the ability of alpha4beta7 to bind MAdCAM-1 or that inhibit cellular interactions such as adhesion between cells expressing alpha4beta7 and cells expressing MAdCAM-1. The site of action may be, for example, intracellular (e.g., by interfering with an intracellular signaling cascade) or extracellular. An antigen binding protein need not completely inhibit alpha4beta7 induced activity to find use in the present invention; rather, antigen binding proteins that reduce a particular activity of alpha4beta7 are contemplated for use as well. (Discussions herein of particular mechanisms of action for alpha4beta7-binding antigen binding proteins in treating particular diseases are illustrative only, and the methods presented herein are not bound thereby.)

Other derivatives of anti-alpha4beta7 antibodies within the scope of this invention include covalent or aggregative conjugates of anti-alpha4beta7 antibodies, or fragments thereof, with other proteins or polypeptides, such as by expression of recombinant fusion proteins comprising heterologous polypeptides fused to the N-terminus or C-terminus of an anti-alpha4beta7 antibody polypeptide. For example, the conjugated peptide may be a heterologous signal (or leader) polypeptide, e.g., the yeast alpha-factor leader, or a peptide such as an epitope tag. Antigen binding protein-containing fusion proteins can comprise peptides added to facilitate purification or identification of antigen binding protein (e.g., poly-His). An antigen binding protein also can be linked to the FLAG® peptide Asp-Tyr-Lys-Asp-Asp-Asp-Asp-Lys (DYKDDDDK) (SEQ ID NO:62) as described in Hopp et al., *Bio/Technology* 6:1204, 1988, and U.S. Pat. No. 5,011,912. The FLAG® peptide is highly antigenic and provides an epitope reversibly bound by a specific monoclonal antibody (mAb), enabling rapid assay and facile purification of expressed recombinant protein. Reagents useful for preparing fusion proteins in which the FLAG® peptide is fused to a given polypeptide are commercially available (Sigma-Aldrich, St. Louis Mo.).

Oligomers that contain one or more antigen binding proteins may be employed as alpha4beta7 antagonists. Oligomers may be in the form of covalently-linked or non-covalently-linked dimers, trimers, or higher oligomers. Oligomers comprising two or more antigen binding protein are contemplated for use, with one example being a homodimer. Other oligomers include heterodimers, homotrimers, heterotrimers, homotetramers, heterotetramers, etc.

One embodiment is directed to oligomers comprising multiple antigen binding proteins joined via covalent or non-covalent interactions between peptide moieties fused to the antigen binding proteins. Such peptides may be peptide linkers (spacers), or peptides that have the property of promoting oligomerization. Leucine zippers and certain polypeptides derived from antibodies are among the peptides that can promote oligomerization of antigen binding proteins attached thereto, as described in more detail below.

In particular embodiments, the oligomers comprise from two to four antigen binding proteins. The antigen binding proteins of the oligomer may be in any form, such as any of the forms described above, e.g., variants or fragments. Preferably, the oligomers comprise antigen binding proteins that have alpha4beta7 binding activity.

In one embodiment, an oligomer is prepared using polypeptides derived from immunoglobulins. Preparation of fusion proteins comprising certain heterologous polypeptides fused to various portions of antibody-derived polypeptides (including the Fc domain) has been described, e.g., by Ashkenazi et al., 1991, PNAS USA 88:10535; Byrn et al., 1990, Nature 344:677; and Hollenbaugh et al., 1992 "Construction of Immunoglobulin Fusion Proteins", in *Current Protocols in Immunology*, Suppl. 4, pages 10.19.1-10.19.11.

One embodiment of the present invention is directed to a dimer comprising two fusion proteins created by fusing an alpha4beta7 binding fragment of an anti-alpha4beta7 antibody to the Fc region of an antibody. The dimer can be made by, for example, inserting a gene fusion encoding the fusion protein into an appropriate expression vector, expressing the gene fusion in host cells transformed with the recombinant expression vector, and allowing the expressed fusion protein to assemble much like antibody molecules, whereupon interchain disulfide bonds form between the Fc moieties to yield the dimer.

The term "Fc polypeptide" as used herein includes native and mutein forms of polypeptides derived from the Fc region of an antibody. Truncated forms of such polypeptides containing the hinge region that promotes dimerization also are included. Fusion proteins comprising Fc moieties (and oligomers formed therefrom) offer the advantage of facile purification by affinity chromatography over Protein A or Protein G columns.

One suitable Fc polypeptide, described in PCT application WO 93/10151 (hereby incorporated by reference), is a single chain polypeptide extending from the N-terminal hinge region to the native C-terminus of the Fc region of a human IgG1 antibody. Another useful Fc polypeptide is the Fc mutein described in U.S. Pat. No. 5,457,035 and in Baum et al., 1994, EMBO J. 13:3992-4001. The amino acid sequence of this mutein is identical to that of the native Fc sequence presented in WO 93/10151, except that amino acid 19 has been changed from Leu to Ala, amino acid 20 has been changed from Leu to Glu, and amino acid 22 has been changed from Gly to Ala. The mutein exhibits reduced affinity for Fc receptors.

In other embodiments, the variable portion of the heavy and/or light chains of an anti-alpha4beta7 antibody may be substituted for the variable portion of an antibody heavy and/or light chain.

Alternatively, the oligomer is a fusion protein comprising multiple antigen binding proteins, with or without peptide linkers (spacer peptides). Among the suitable peptide linkers are those described in U.S. Pat. Nos. 4,751,180 and 4,935,233.

Another method for preparing oligomeric antigen binding proteins involves use of a leucine zipper. Leucine zipper domains are peptides that promote oligomerization of the proteins in which they are found. Leucine zippers were originally identified in several DNA-binding proteins (Landschulz et al., 1988, Science 240:1759), and have since been found in a variety of different proteins. Among the known leucine zippers are naturally occurring peptides and derivatives thereof that dimerize or trimerize. Examples of leucine zipper domains suitable for producing soluble oligomeric proteins are described in PCT application WO 94/10308, and the leucine zipper derived from lung surfactant protein D (SPD) described in Hoppe et al., 1994, FEBS Letters 344:191, hereby incorporated by reference. The use of a modified leucine zipper that allows for stable trimerization of a heterologous protein fused thereto is described in Fanslow et al., 1994, Semin. Immunol. 6:267-78. In one approach, recombinant fusion proteins comprising an anti-alpha4beta7 antibody fragment or derivative fused to a leucine zipper peptide are expressed in suitable host cells, and the soluble oligomeric anti-alpha4beta7 antibody fragments or derivatives that form are recovered from the culture supernatant.

In one aspect, the present invention provides antigen binding proteins that interfere with the binding of alpha4beta7 to MAdCAM-1. Such antigen binding proteins can be made against alpha4beta7, or a fragment, variant or derivative thereof, and screened in conventional assays for the ability to interfere with the binding of alpha4beta7 to MAdCAM-1. Examples of suitable assays are assays that test the antigen binding proteins for the ability to inhibit binding of MAdCAM-1 (i.e., soluble MAdCAM-1) to cells expressing alpha4beta7, or that test antigen binding proteins for the ability to reduce a biological or cellular response that results from the interaction of MAdCAM-1 and alpha4beta7 (i.e., adhesion of cells expressing alpha4beta7 to MAdCAM-1, or MAdCAM-1-expressing cells). Additional assays that test the antigen binding proteins include those that qualitatively or quantitatively compare the binding of an antigen binding protein to a alpha4beta7 polypeptide to the binding of a known antigen binding protein to a alpha4beta7 polypeptide, several examples of which are disclosed herein.

In another aspect, the present invention provides an antigen binding protein that demonstrates species selectivity. In one embodiment, the antigen binding protein binds to one or more mammalian alpha4beta7, for example, to human alpha4beta7 and one or more of mouse, rat, guinea pig, hamster, gerbil, cat, rabbit, dog, goat, sheep, cow, horse, camel, and non-human primate alpha4beta7. In another embodiment, the antigen binding protein binds to one or more primate alpha4beta7, for example, to human alpha4beta7 and one or more of cynomologous, marmoset, rhesus, tamarin and chimpanzee alpha4beta7. In another embodiment, the antigen binding protein binds specifically to human, cynomologous, marmoset, rhesus, tamarin or chimpanzee alpha4beta7. In another embodiment, the antigen binding protein does not bind to one or more of mouse, rat, guinea pig, hamster, gerbil, cat, rabbit, dog, goat, sheep, cow, horse, camel, and non-human primate alpha4beta7. In another embodiment, the antigen binding protein does not bind to a New World monkey species such as a marmoset.

In another embodiment, the antigen binding protein does not exhibit specific binding to any naturally occurring protein other than alpha4beta7. In another embodiment, the antigen binding protein does not exhibit specific binding to any naturally occurring protein other than mammalian alpha4beta7. In another embodiment, the antigen binding protein does not exhibit specific binding to any naturally occurring protein other than primate alpha4beta7. In another embodiment, the antigen binding protein does not exhibit specific binding to any naturally occurring protein other than human alpha4beta7. In another embodiment, the antigen binding protein specifically binds to alpha4beta7 from at least one non-human primate, for example, cynomologous monkey, and human alpha4beta7. In another embodiment, the antigen binding protein specifically binds to non-human primate, cynomologous monkey, and human alpha4beta7 with a similar binding affinity. In another embodiment, the antigen binding protein blocks an activity of non-human primate, cynomologous monkey, and human alpha4beta7. In another embodiment, the antigen binding protein has a similar $IC_{50}$ or $EC_{50}$ against non-human primate, cynomologous monkey, and human alpha4beta7 in an assay as described herein.

One may determine the selectivity of an antigen binding protein for an alpha4beta7 using methods well known in the art and following the teachings of the specification. For example, one may determine the selectivity using Western blot, FACS, ELISA or RIA.

In another aspect, the present invention provides an alpha4beta7 binding antigen binding protein (for example, an anti-alpha4beta7 antibody), that has one or more of the following characteristics: binds to both human and non-human primate alpha4beta7, inhibits binding of MAdCAM-1 to alpha4beta7, inhibits the adhesion of cells expressing alpha4beta7 to MAdCAM-1, inhibits the adhesion of cells expressing alpha4beta7 to cells expressing MAdCAM-1, inhibits trafficking of cells expressing alpha4beta7 to tissues comprising cells expressing MAdCAM-1, binds both active and inactive forms of alpha4beta7, causes relatively little down-regulation of cell-surface expressed alpha4beta7.

Antigen-binding fragments of antigen binding proteins of the invention may be produced by conventional techniques. Examples of such fragments include, but are not limited to, Fab and $F(ab')_2$ fragments. Antibody fragments and derivatives produced by genetic engineering techniques also are contemplated.

Additional embodiments include chimeric antibodies, e.g., humanized versions of non-human (e.g., murine) monoclonal antibodies. Such humanized antibodies may be prepared by known techniques, and offer the advantage of reduced immunogenicity when the antibodies are administered to humans. In one embodiment, a humanized monoclonal antibody comprises the variable domain of a murine antibody (or all or part of the antigen binding site thereof) and a constant domain derived from a human antibody. Alternatively, a humanized antibody fragment may comprise the antigen binding site of a murine monoclonal antibody and a variable domain fragment (lacking the antigen-binding site) derived from a human antibody. Procedures for the production of chimeric and further engineered monoclonal antibodies include those described in Riechmann et al., 1988, Nature 332:323, Liu et al., 1987, Proc. Nat. Acad. Sci. USA 84:3439, Larrick et al., 1989, Bio/Technology 7:934, and Winter et al., 1993, TIPS 14:139.

In one embodiment, the chimeric antibody is a CDR grafted antibody. Techniques for humanizing antibodies are discussed in, e.g., U.S. patent application Ser. No. 10/194,975 (published Feb. 27, 2003), U.S. Pat. Nos. 5,869,619, 5,225, 539, 5,821,337, 5,859,205, Padlan et al., 1995, FASEB J. 9:133-39, and Tamura et al., 2000, J. Immunol. 164:1432-41.

Procedures have been developed for generating human or partially human antibodies in non-human animals. For example, mice in which one or more endogenous immunoglobulin genes have been inactivated by various means have been prepared. Human immunoglobulin genes have been introduced into the mice to replace the inactivated mouse genes. Antibodies produced in the animal incorporate human immunoglobulin polypeptide chains encoded by the human genetic material introduced into the animal. In one embodiment, a non-human animal, such as a transgenic mouse, is immunized with an alpha4beta7 polypeptide, such that antibodies directed against the alpha4beta7 polypeptide are generated in the animal. One example of a suitable immunogen is a soluble human alpha4beta7, such as a polypeptide comprising a portion of alpha4beta7, or other immunogenic fragment alpha4beta7. Another example of a suitable immunogen is cells expressing high levels of alpha4beta7, or cell membrane preparations therefrom.

Examples of techniques for production and use of transgenic animals for the production of human or partially human antibodies are described in U.S. Pat. Nos. 5,814,318, 5,569, 825, and 5,545,806, Davis et al., 2003, *Production of human antibodies from transgenic mice* in Lo, ed. Antibody Engineering Methods and Protocols, Humana Press, N.J.: 191-200, Kellermann et al., 2002, Curr Opin Biotechnol. 13:593-97, Russel et al., 2000, Infect Immun. 68:1820-26, Gallo et al., 2000, Eur J. Immun. 30:534-40, Davis et al., 1999, Cancer Metastasis Rev. 18:421-25, Green, 1999, J Immunol Methods. 231:11-23, Jakobovits, 1998, Adv Drug Deliv Rev 31:33-42, Green et al., 1998, J Exp Med. 188:483-95, Jakobovits A, 1998, Exp. Opin. Invest. Drugs. 7:607-14, Tsuda et al., 1997, Genomics 42:413-21, Mendez et al., 1997, Nat. Genet. 15:146-56, Jakobovits, 1994, Curr Biol. 4:761-63, Arbones et al., 1994, Immunity. 1:247-60, Green et al., 1994, Nat. Genet. 7:13-21, Jakobovits et al., 1993, Nature 362:255-58, Jakobovits et al., 1993, Proc Natl Acad Sci USA. 90:2551-55. Chen, J. et al., 1993, Int Immunol 5: 647-656, Choi et al., 1993, Nature Genetics 4: 117-23, Fishwild et al., 1996, Nat Biotechnol 14: 845-51, Harding et al., 1995, Ann NY Acad Sci, Lonberg et al., 1994, Nature 368: 856-59, Lonberg, 1994, *Transgenic Approaches to Human Monoclonal Antibodies* in Handbook of Experimental Pharmacology 113: 49-101, Lonberg et al., 1995, Int Rev Immunol 13: 65-93, Neuberger, 1996, Nat Biotechnol 14: 826, Taylor et al., 1992, Nucleic Acids Research 20: 6287-95, Taylor et al., 1994, Int Immunol 6: 579-91, Tomizuka et al., 1997, Nat Gen 16: 133-43, Tomizuka et al., 2000, Proc Natl Acad Sci USA. 97: 722-27, Tuaillon et al., 1993, Proc Natl Acad Sci USA. 90: 3720-24, and Tuaillon et al., 1994, J Immunol 152: 2912-20. These and other examples are also discussed in U.S. Patent application publication 2007-0098715, published May 3, 2007.

In another aspect, the present invention provides monoclonal antibodies that bind to alpha4beta7. Monoclonal antibodies may be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XX0 Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

In one embodiment, a hybridoma cell line is produced by immunizing an animal (e.g., a transgenic animal having human immunoglobulin sequences) with an alpha4beta7 immunogen; harvesting spleen cells from the immunized animal; fusing the harvested spleen cells to a myeloma cell line, thereby generating hybridoma cells; establishing hybridoma cell lines from the hybridoma cells, and identifying a hybridoma cell line that produces an antibody that binds an alpha4beta7 polypeptide. Such hybridoma cell lines, and anti-alpha4beta7 monoclonal antibodies produced by them, are encompassed by the present invention.

Monoclonal antibodies secreted by a hybridoma cell line can be purified using any technique known in the art. Hybridomas or mAbs may be further screened to identify mAbs with particular properties, such as the ability to block an alpha4beta7 induced activity. Examples of such screens are provided in the examples below.

Monoclonal antibodies can also be produced using a process referred to as genetic immunization. For example, a nucleic acid encoding the antigen of interest can be incorporated into a viral vector (such as an adenoviral vector). The resulting vector is then used to develop an immune response against the antigen of interest in a suitable host animal (for example, a non-obese diabetic, or NOD, mouse). This techniques is substantially described by Ritter et al., Biodrugs 16(1): 3-10 (2002), the disclosure of which is incorporated by reference herein.

Molecular evolution of the complementarity determining regions (CDRs) in the center of the antibody binding site also has been used to isolate antibodies with increased affinity, for example, antibodies having increased affinity for c-erbB-2, as described by Schier et al., 1996, J. Mol. Biol. 263:551. Accordingly, such techniques are useful in preparing antibodies to alpha4beta7.

Antigen binding proteins directed against an alpha4beta7 can be used, for example, in assays to detect the presence of alpha4beta7 polypeptides or cells expressing alpha4beta7, either in vitro or in vivo. The antigen binding proteins also may be employed in purifying alpha4beta7 proteins by immunoaffinity chromatography. Those antigen binding proteins that additionally can block the interaction of MAdCAM-1 and alpha4beta7 may be used to inhibit a biological activity that results from such interaction. Blocking antigen binding proteins can be used in the methods of the present invention. Such antigen binding proteins that function as alpha4beta7 antagonists may be employed in treating any alpha4beta7-induced condition, including but not limited to inflammatory conditions. In one embodiment, a human anti-alpha4beta7 monoclonal antibody generated by procedures involving immunization of transgenic mice is employed in treating such conditions.

Antigen binding proteins may be employed in an in vitro procedure, or administered in vivo to inhibit an alpha4beta7-induced biological activity. Disorders caused or exacerbated (directly or indirectly) by alpha4beta7 and its interaction with MAdCAM-1, examples of which are provided herein, thus may be treated. In one embodiment, the present invention provides a therapeutic method comprising in vivo administration of an alpha4beta7 blocking antigen binding protein to a mammal in need thereof in an amount effective for reducing an alpha4beta7-induced biological activity.

Antigen binding proteins of the invention include partially human and fully human monoclonal antibodies that inhibit a biological activity of alpha4beta7. One embodiment is directed to a human monoclonal antibody that at least partially blocks the interaction of human alpha4beta7 with MAdCAM-1. In one embodiment, the antibodies are generated by immunizing a transgenic mouse with an alpha4beta7 immunogen. In another embodiment, the immunogen is a human alpha4beta7 polypeptide (e.g., a cell transformed or transfected to express alpha4beta7, or a cell that naturally expresses alpha4beta7). Hybridoma cell lines derived from such immunized mice, wherein the hybridoma secretes a monoclonal antibody that binds alpha4beta7, also are provided herein.

Although human, partially human, or humanized antibodies will be suitable for many applications, particularly those involving administration of the antibody to a human subject, other types of antigen binding proteins will be suitable for certain applications. The non-human antibodies of the invention can be, for example, derived from any antibody-producing animal, such as mouse, rat, rabbit, goat, donkey, or non-human primate (such as monkey (e.g., cynomologous or rhesus monkey) or ape (e.g., chimpanzee)). Non-human antibodies of the invention can be used, for example, in in vitro and cell-culture based applications, or any other application where an immune response to the antibody of the invention does not occur, is insignificant, can be prevented, is not a concern, or is desired. In one embodiment, a non-human antibody of the invention is administered to a non-human subject. In another embodiment, the non-human antibody does not elicit an immune response in the non-human subject. In another embodiment, the non-human antibody is from the same species as the non-human subject, e.g., a mouse antibody of the invention is administered to a mouse. An antibody from a particular species can be made by, for example, immunizing an animal of that species with the desired immunogen (e.g., cells expressing alph4beta7, or a soluble alpha4beta7 polypeptide) or using an artificial system for generating antibodies of that species (e.g., a bacterial or phage display-based system for generating antibodies of a particular species), or by converting an antibody from one species into an antibody from another species by replacing, e.g., the constant region of the antibody with a constant region from the other species, or by replacing one or more amino acid residues of the antibody so that it more closely resembles the sequence of an antibody from the other species. In one embodiment, the antibody is a chimeric antibody comprising amino acid sequences derived from antibodies from two or more different species.

Antigen binding proteins may be prepared by any of a number of conventional techniques. For example, they may be purified from cells that naturally express them (e.g., an antibody can be purified from a hybridoma that produces it), or produced in recombinant expression systems, using any technique known in the art. See, for example, *Monoclonal Antibodies, Hybridomas: A New Dimension in Biological Analyses*, Kennet et al. (eds.), Plenum Press, New York (1980); and *Antibodies: A Laboratory Manual*, Harlow and Land (eds.), Cold Spring Harbor Laboratory Press, Cold Spring Harbor, N.Y., (1988).

Any expression system known in the art can be used to make the recombinant polypeptides of the invention. In general, host cells are transformed with a recombinant expression vector that comprises DNA encoding a desired polypeptide. Among the host cells that may be employed are prokaryotes, yeast or higher eukaryotic cells. Prokaryotes include gram negative or gram positive organisms, for example *E. coli* or bacilli. Higher eukaryotic cells include insect cells and established cell lines of mammalian origin. Examples of suitable mammalian host cell lines include the COS-7 line of monkey kidney cells (ATCC CRL 1651) (Gluzman et al., 1981, Cell 23:175), L cells, 293 cells, C127 cells, 3T3 cells (ATCC CCL 163), Chinese hamster ovary (CHO) cells, HeLa cells, BHK (ATCC CRL 10) cell lines, and the CVI/EBNA cell line derived from the African green monkey kidney cell line CVI (ATCC CCL 70) as described by McMahan et al., 1991, EMBO J. 10: 2821. Appropriate cloning and expression vectors for use with bacterial, fungal, yeast, and mammalian cellular hosts are described by Pouwels et al. (*Cloning Vectors: A Laboratory Manual*, Elsevier, N.Y., 1985).

The transformed cells can be cultured under conditions that promote expression of the polypeptide, and the polypeptide recovered by conventional protein purification procedures. One such purification procedure includes the use of affinity chromatography, e.g., over a matrix having all or a portion (e.g., the extracellular domain) of alpha4beta7 bound thereto. Polypeptides contemplated for use herein include substantially homogeneous recombinant mammalian anti-alpha4beta7 antibody polypeptides substantially free of contaminating endogenous materials.

The amino acid sequence of the polypeptides may be verified by any means known in the art, and may be identical to the sequences disclosed herein in the Sequence Listing, or may differ from those sequences at one or more amino acid residues as result of processing. For example, on all or a portion of the substantially homogenous polypeptides, a C-terminal amino acid from either the light chain or the heavy chain (or relevant single-chain molecule) may be removed, by proteolytic processing or other processing that occurs during culture, for example, processing of C-terminal Lys residues. Alternatively, more than one C-terminal amino acid residue is removed, for example two C-terminal amino acids, or three, four or five C-terminal amino acids. For example, a C-terminal might be truncated to amidated proline of the heavy chain of an antibody as disclosed. Similarly, N-terminal amino acids may be absent, for example, one, two, three, four or five N-terminal amino acids may be absent.

Alternatively, or additionally, amino acid residues may undergo post-translational modifications, for example but not limited to, glutamine (in particular, glutamine at the N-terminus) may be cyclized or converted to pyroglutamic acid; additionally or alternatively, amino acids may undergo deamidation, isomerization, glycation and/or oxidation. The polypeptides of the invention may undergo additional post-translational modification, including glycosylation, for example N-linked or O-linked glycosylation, at sites that are well-known in the art. As described previously, changes may be made in the amino acid sequence of a polypeptide to preclude or minimize such alterations, or to facilitate them in circumstances where such processing is beneficial.

Preparations of substantially homogenous polypeptides may comprise about 1%, 5%, 10%, 20%, 30%, 40%, 50%, 60%, 70%, 75%, 80%, 85%, 90%, 95%, 97%, 98%, or 99% polypeptide having undergone a particular form (or forms) of processing. Preparations of substantially homogenous polypeptides may comprise some (less than or equal to 50%), most (more than 50% but less than 90%) or substantially all (more than 90%) of a particular form(s) of processed polypeptide. Moreover, such preparations may comprise polypeptides that have varying levels of more than one type of processing-related modification, for example, a polypeptide may have some, most or substantially all of a C-terminal lysine removed (for example, the C-terminal lysine in SEQ ID NO: 72) and some, most or substantially all of an N-terminal amino acid converted to pyroglutamic acid (for example, any polypeptide shown in Table 1 and/or 2 or in the consensus sequences).

Antigen binding proteins may be prepared, and screened for desired properties, by any of a number of known techniques. Certain of the techniques involve isolating a nucleic acid encoding a polypeptide chain (or portion thereof) of an antigen binding protein of interest (e.g., an anti-alpha4beta7 antibody), and manipulating the nucleic acid through recombinant DNA technology. The nucleic acid may be fused to another nucleic acid of interest, or altered (e.g., by mutagenesis or other conventional techniques) to add, delete, or substitute one or more amino acid residues, for example.

In one aspect, the present invention provides antigen-binding fragments of an anti-alpha4beta7 antibody of the invention. Such fragments can consist entirely of antibody-derived sequences or can comprise additional sequences. Examples of antigen-binding fragments include Fab, F(ab')$_2$, single chain antibodies, diabodies, triabodies, tetrabodies, and domain antibodies. Other examples are provided in Lunde et al., 2002, Biochem. Soc. Trans. 30:500-06.

Single chain antibodies may be formed by linking heavy and light chain variable domain (Fv region) fragments via an amino acid bridge (short peptide linker), resulting in a single polypeptide chain. Such single-chain Fvs (scFvs) have been prepared by fusing DNA encoding a peptide linker between DNAs encoding the two variable domain polypeptides ($V_L$ and $V_H$). The resulting polypeptides can fold back on themselves to form antigen-binding monomers, or they can form multimers (e.g., dimers, trimers, or tetramers), depending on the length of a flexible linker between the two variable domains (Kortt et al., 1997, Prot. Eng. 10:423; Kortt et al., 2001, Biomol. Eng. 18:95-108). By combining different $V_L$ and $V_H$-comprising polypeptides, one can form multimeric scFvs that bind to different epitopes (Kriangkum et al., 2001, Biomol. Eng. 18:31-40). Techniques developed for the production of single chain antibodies include those described in U.S. Pat. No. 4,946,778; Bird, 1988, Science 242:423; Huston et al., 1988, Proc. Natl. Acad. Sci. USA 85:5879; Ward et al., 1989, Nature 334:544, de Graaf et al., 2002, Methods Mol. Biol. 178:379-87.

Antigen binding proteins (e.g., antibodies, antibody fragments, and antibody derivatives) of the invention can comprise any constant region known in the art. The light chain constant region can be, for example, a kappa- or lambda-type light chain constant region, e.g., a human kappa- or lambda-type light chain constant region. The heavy chain constant region can be, for example, an alpha-, delta-, epsilon-, gamma-, or mu-type heavy chain constant regions, e.g., a human alpha-, delta-, epsilon-, gamma-, or mu-type heavy chain constant region. In one embodiment, the light or heavy chain constant region is a fragment, derivative, variant, or mutein of a naturally occurring constant region.

Techniques are known for deriving an antibody of a different subclass or isotype from an antibody of interest, i.e., subclass switching. Thus, IgG antibodies may be derived from an IgM antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g., DNA encoding the constant domain of an antibody of the desired isotype. See also Lantto et al., 2002, Methods Mol. Biol. 178:303-16. Moreover, if an IgG4 is desired, it may also be desired to introduce a point mutation (CPSCP->CPPCP) in the hinge region as described in Bloom et al., 1997, Protein Science 6:407, incorporated by reference herein) to alleviate a tendency to form intra-H chain disulfide bonds that can lead to heterogeneity in the IgG4 antibodies.

Moreover, techniques for deriving antigen binding proteins having different properties (i.e., varying affinities for the antigen to which they bind) are also known. One such technique, referred to as chain shuffling, involves displaying immunoglobulin variable domain gene repertoires on the surface of filamentous bacteriophage, often referred to as phage display. Chain shuffling has been used to prepare high affinity antibodies to the hapten 2-phenyloxazol-5-one, as described by Marks et al., 1992, BioTechnology, 10:779.

In another embodiment, the present invention provides an antigen binding protein that has a low dissociation constant from alpha4beta7. In one embodiment, the antigen binding protein has a $K_d$ of 100 pM or lower. In another embodiment, the $K_d$ is 10 pM or lower; in another embodiment, it is 5 pM or lower, or it is 1 pM or lower. In another embodiment, the $K_d$ is substantially the same as an antibody described herein in the Examples. In another embodiment, the antigen binding protein binds to alpha4beta7 with substantially the same $K_d$ as an antibody described herein in the Examples.

In another aspect, the present invention provides an antigen binding protein that inhibits an activity of alpha4beta7, for example binding (or adhesion) to MAdCAM-1, binding to cells expressing MAdCAM-1, or adhesion between cells expressing alpha4beta7 and cells expressing MAdCAM-1. In one embodiment, the antigen binding protein has an $IC_{50}$ of 1000 pM or lower. In another embodiment, the $IC_{50}$ is 500 pM or lower; in another embodiment, the $IC_{50}$ is 100 pM or lower. In another embodiment, the $IC_{50}$ is substantially the same as that of an antibody described herein in the Examples. In another embodiment, the antigen binding protein inhibits an activity of alpha4beta7 with substantially the same $IC_{50}$ as an antibody described herein in the Examples.

In one embodiment, antigen binding proteins of the present invention have an apparent affinity for alpha4beta7 (or cells expressing alpha4beta7) of 1000 pM or lower. In other embodiments, the antigen binding proteins exhibit an apparent affinity of 500 pM or lower, 200 pM or lower, 100 pM or lower, 80 pM or lower, 40 pM or lower, or 15 pM or lower. In another embodiment, the antigen binding protein exhibits an apparent affinity substantially the same as that of an antibody described herein in the Examples. In another embodiment, the antigen binding protein has an apparent affinity substantially the same that of an antibody described herein in the Examples.

In another aspect, the present invention provides an antigen binding protein that binds both active and inactive forms of alpha4beta7. In another embodiment, an antigen binding protein binds only one form, or preferentially binds one form, of alpha4beta7. For example, an antigen binding protein may bind alpha4beta7 in the presence or absence of $Mn^{2+}$ (i.e., it binds both active and inactive forms). Alternatively, an antigen binding protein may bind alpha4beta7 only in the presence of $Mn^{2+}$ or only in the absence of $Mn^{2+}$, or it may bind with higher affinity under one such condition than another, indicating preferential binding to a particular form of alpha4beta7.

In another embodiment, the present invention provides an antigen binding protein that competes for binding to alpha4beta7 with an antibody disclosed herein. Such competitive ability can be determined by methods that are well-known in the art, for example by competition in binding to alpha4beta7-expressing cells as observed using fluorescence activate cells sorting (FACS) techniques or other, similar assays, by competition in an assay such as an adhesion assay (i.e., between cells expressing alpha4beta7 and cells expressing MAdCAM-1), or by competition in another assay described herein. In one aspect, an antigen binding protein that competes for binding to alpha4beta7 with an antibody disclosed herein binds the same epitope or an overlapping (or adjacent) epitope as the antibody. In another aspect, the antigen binding protein that competes for binding to alpha4beta7 with an antibody disclosed herein inhibits an activity of alpha4beta7.

In another aspect, the present invention provides an antigen binding protein that binds to human alpha4beta7 expressed on the surface of a cell and, when so bound, inhibits alpha4beta7 interaction with MAdCAM-1 without causing a significant reduction in the amount of alpha4beta7 on the surface of the cell. Any method for determining or estimating the amount of alpha4beta7 on the surface and/or in the interior of the cell can be used. In one embodiment, the present invention provides an antigen binding protein that binds to alpha4beta7 expressed on the surface of a cell and, when so bound, inhibits alpha4beta7 interaction with MAdCAM-1 without significantly increasing the rate of internalization of the alpha4beta7 from the surface of the cell. In other embodiments, binding of the antigen binding protein to the alpha4beta7-expressing cell causes less than about 75%, 50%, 40%, 30%, 20%, 15%, 10%, 5%, 1%, or 0.1% of the cell-surface alpha4beta7 to be internalized.

In another aspect, the present invention provides an antigen binding protein having a half-life of at least one day in vitro or in vivo (e.g., when administered to a human subject). In one embodiment, the antigen binding protein has a half-life of at least three days. In another embodiment, the antigen binding protein has a half-life of four days or longer. In another embodiment, the antigen binding protein has a half-life of eight days or longer. In another embodiment, the antigen binding protein is derivatized or modified such that it has a longer half-life as compared to the underivatized or unmodified antigen binding protein. In another embodiment, the antigen binding protein contains one or more point mutations to increase serum half life, such as described in WO 00/09560, published Feb. 24, 2000, incorporated by reference.

The present invention further provides multi-specific antigen binding proteins, for example, bispecific antigen binding protein, e.g., antigen binding protein that bind to two different epitopes of alpha4beta7, or to an epitope of alpha4beta7 and an epitope of another molecule, via two different antigen binding sites or regions. Moreover, bispecific antigen binding protein as disclosed herein can comprise an alpha4beta7 binding site from one of the herein-described antibodies and a second alpha4beta7 binding region from another of the herein-described antibodies, including those described herein by reference to other publications. Alternatively, a bispecific antigen binding protein may comprise an antigen binding site from one of the herein described antibodies and a second antigen binding site from another alpha4beta7 antibody that is known in the art, or from an antibody that is prepared by known methods or the methods described herein.

Numerous methods of preparing bispecific antibodies are known in the art, and discussed in U.S. patent application Ser. No. 09/839,632, filed Apr. 20, 2001 (incorporated by reference herein). Such methods include the use of hybrid-hybridomas as described by Milstein et al., 1983, Nature 305:537, and others (U.S. Pat. No. 4,474,893, U.S. Pat. No. 6,106,833), and chemical coupling of antibody fragments (Brennan et al., 1985, Science 229:81; Glennie et al., 1987, J. Immunol. 139: 2367; U.S. Pat. No. 6,010,902). Moreover, bispecific antibodies can be produced via recombinant means, for example by using leucine zipper moieties (i.e., from the Fos and Jun proteins, which preferentially form heterodimers; Kostelny et al., 1992, J. Immunol. 148:1547) or other lock and key interactive domain structures as described in U.S. Pat. No. 5,582, 996. Additional useful techniques include those described in Kortt et al., 1997, supra; U.S. Pat. No. 5,959,083; and U.S. Pat. No. 5,807,706.

In another aspect, the antigen binding protein of the present invention comprises a derivative of an antibody. The derivatized antibody can comprise any molecule or substance that imparts a desired property to the antibody, such as increased half-life in a particular use. The derivatized antibody can comprise, for example, a detectable (or labeling) moiety (e.g., a radioactive, colorimetric, antigenic or enzymatic molecule, a detectable bead (such as a magnetic or electrodense (e.g., gold) bead), or a molecule that binds to another molecule (e.g., biotin or streptavidin)), a therapeutic or diagnostic moiety (e.g., a radioactive, cytotoxic, or pharmaceutically active moiety), or a molecule that increases the suitability of the antibody for a particular use (e.g., administration to a subject, such as a human subject, or other in vivo or in vitro uses). Examples of molecules that can be used to derivatize an antibody include albumin (e.g., human serum albumin) and polyethylene glycol (PEG). Albumin-linked and PEGylated derivatives of antibodies can be prepared using techniques well known in the art. In one embodiment, the antibody is conjugated or otherwise linked to transthyretin (TTR) or a TTR variant. The TTR or TTR variant can be chemically modified with, for example, a chemical selected from the group consisting of dextran, poly(n-vinyl pyurrolidone), polyethylene glycols, propropylene glycol homopolymers, polypropylene oxide/ethylene oxide co-polymers, polyoxyethylated polyols and polyvinyl alcohols. US Pat. App. No. 20030195154.

In another aspect, the present invention provides methods of screening for a molecule that binds to alpha4beta7 using the antigen binding proteins of the present invention. Any suitable screening technique can be used. In one embodiment, an alpha4beta7 molecule, or a fragment thereof to which an antigen binding protein of the present invention binds, is contacted with the antigen binding protein of the invention and with another molecule, wherein the other molecule binds to alpha4beta7 if it reduces the binding of the antigen binding protein to alpha4beta7. Binding of the antigen binding protein can be detected using any suitable method, e.g., an ELISA. Detection of binding of the antigen binding protein to alpha4beta7 can be simplified by detectably labeling the antigen binding protein, as discussed above. In another embodiment, the alpha4beta7-binding molecule is further analyzed to determine whether it inhibits alpha4beta7 activation and/or signaling.

Nucleic Acids

In one aspect, the present invention provides isolated nucleic acid molecules. The nucleic acids comprise, for example, polynucleotides that encode all or part of an antigen binding protein, for example, one or both chains of an antibody of the invention, or a fragment, derivative, mutein, or variant thereof, polynucleotides sufficient for use as hybridization probes, PCR primers or sequencing primers for identifying, analyzing, mutating or amplifying a polynucleotide encoding a polypeptide, anti-sense nucleic acids for inhibiting expression of a polynucleotide, and complementary sequences of the foregoing. The nucleic acids can be any length. They can be, for example, 5, 10, 15, 20, 25, 30, 35, 40, 45, 50, 75, 100, 125, 150, 175, 200, 250, 300, 350, 400, 450, 500, 750, 1,000, 1,500, 3,000, 5,000 or more nucleotides in length, and/or can comprise one or more additional sequences, for example, regulatory sequences, and/or be part of a larger nucleic acid, for example, a vector. The nucleic acids can be single-stranded or double-stranded and can comprise RNA and/or DNA nucleotides, and artificial variants thereof (e.g., peptide nucleic acids).

Nucleic acids encoding antibody polypeptides (e.g., heavy or light chain, variable domain only, or full length) may be isolated from B-cells of mice that have been immunized with alpha4beta7. The nucleic acid may be isolated by conventional procedures such as polymerase chain reaction (PCR).

The invention further provides nucleic acids that hybridize to other nucleic acids under particular hybridization conditions. Methods for hybridizing nucleic acids are well-known in the art. See, e.g., Current Protocols in Molecular Biology, John Wiley & Sons, N.Y. (1989), 6.3.1-6.3.6. As defined herein, a moderately stringent hybridization condition uses a prewashing solution containing 5× sodium chloride/sodium citrate (SSC), 0.5% SDS, 1.0 mM EDTA (pH 8.0), hybridization buffer of about 50% formamide, 6×SSC, and a hybridization temperature of 55° C. (or other similar hybridization solutions, such as one containing about 50% formamide, with a hybridization temperature of 42° C.), and washing conditions of 60° C., in 0.5×SSC, 0.1% SDS. A stringent hybridization condition hybridizes in 6×SSC at 45° C., followed by one or more washes in 0.1×SSC, 0.2% SDS at 68° C. Furthermore, one of skill in the art can manipulate the hybridization and/or washing conditions to increase or decrease the stringency of hybridization such that nucleic acids comprising nucleotide sequences that are at least 65, 70, 75, 80, 85, 90, 95, 98 or 99% identical to each other typically remain hybridized to each other. The basic parameters affecting the choice of hybridization conditions and guidance for devising suitable conditions are set forth by, for example, Sambrook, Fritsch, and Maniatis (1989, Molecular Cloning: A Laboratory Manual, Cold Spring Harbor Laboratory Press, Cold Spring Harbor, N.Y., chapters 9 and 11; and Current Protocols in Molecular Biology, 1995, Ausubel et al., eds., John Wiley & Sons, Inc., sections 2.10 and 6.3-6.4), and can be readily determined by those having ordinary skill in the art based on, for example, the length and/or base composition of the DNA.

Changes can be introduced by mutation into a nucleic acid, thereby leading to changes in the amino acid sequence of a polypeptide (e.g., an antigen binding protein) that it encodes. Mutations can be introduced using any technique known in the art. In one embodiment, one or more particular amino acid residues are changed using, for example, a site-directed mutagenesis protocol. In another embodiment, one or more randomly selected residues is changed using, for example, a random mutagenesis protocol. However it is made, a mutant polypeptide can be expressed and screened for a desired property (e.g., binding to alpha4beta7 or blocking the binding of alpha4beta7 to an addressin such as MAdCAM).

Mutations can be introduced into a nucleic acid without significantly altering the biological activity of a polypeptide that it encodes. For example, one can make nucleotide substitutions leading to amino acid substitutions at non-essential amino acid residues. In one embodiment, a nucleotide sequence, or a desired fragment, variant, or derivative thereof, is mutated such that it encodes an amino acid sequence comprising one or more deletions or substitutions of amino acid residues. In another embodiment, the mutagenesis inserts an amino acid adjacent to one or more amino acid residues. Alternatively, one or more mutations can be introduced into a nucleic acid that selectively change the biological activity (e.g., binding of alpha4beta7, inhibiting binding of alpha4beta7 to an addressin such as MAdCAM, etc.) of a polypeptide that it encodes. For example, the mutation can quantitatively or qualitatively change the biological activity. Examples of quantitative changes include increasing, reducing or eliminating the activity. Examples of qualitative changes include changing the antigen specificity of an antigen binding protein.

In another aspect, the present invention provides nucleic acid molecules that are suitable for use as primers or hybridization probes for the detection of nucleic acid sequences of the invention. A nucleic acid molecule of the invention can comprise only a portion of a nucleic acid sequence encoding a full-length polypeptide of the invention, for example, a fragment that can be used as a probe or primer or a fragment encoding an active portion (e.g., an alpha4beta7 binding portion) of a polypeptide of the invention.

Probes based on the sequence of a nucleic acid of the invention can be used to detect the nucleic acid or similar nucleic acids, for example, transcripts encoding a polypeptide of the invention. The probe can comprise a label group, e.g., a radioisotope, a fluorescent compound, an enzyme, or an enzyme co-factor. Such probes can be used to identify a cell that expresses the polypeptide.

In another aspect, the present invention provides vectors comprising a nucleic acid encoding a polypeptide of the invention or a portion thereof. Examples of vectors include, but are not limited to, plasmids, viral vectors, non-episomal mammalian vectors and expression vectors, for example, recombinant expression vectors.

The recombinant expression vectors of the invention can comprise a nucleic acid of the invention in a form suitable for expression of the nucleic acid in a host cell. The recombinant expression vectors include one or more regulatory sequences, selected on the basis of the host cells to be used for expression, which is operably linked to the nucleic acid sequence to be expressed. Regulatory sequences include those that direct constitutive expression of a nucleotide sequence in many types of host cells (e.g., SV40 early gene enhancer, Rous sarcoma virus promoter and cytomegalovirus promoter), those that direct expression of the nucleotide sequence only in certain host cells (e.g., tissue-specific regulatory sequences, see Voss et al., 1986, Trends Biochem. Sci. 11:287, Maniatis et al., 1987, Science 236:1237, incorporated by reference herein in their entireties), and those that direct inducible expression of a nucleotide sequence in response to particular treatment or condition (e.g., the metallothionin promoter in mammalian cells and the tet-responsive and/or streptomycin responsive promoter in both prokaryotic and eukaryotic systems (see id.). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein.

In another aspect, the present invention provides host cells into which a recombinant expression vector of the invention has been introduced. A host cell can be any prokaryotic cell (for example, E. coli) or eukaryotic cell (for example, yeast, insect, or mammalian cells (e.g., CHO cells)). Vector DNA can be introduced into prokaryotic or eukaryotic cells via conventional transformation or transfection techniques. For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., for resistance to antibiotics) is generally introduced into the host cells along with the gene of interest. Preferred selectable markers include those that confer resistance to drugs, such as G418, hygromycin and methotrexate. Cells stably transfected with the introduced nucleic acid can be identified by drug selection (e.g., cells that have incorporated the selectable marker gene will survive, while the other cells die), among other methods.

Indications

In one aspect, the present invention provides methods of treating a subject. The method can, for example, have a generally salubrious effect on the subject, e.g., it can increase the subject's expected longevity. Alternatively, the method can, for example, treat, prevent, cure, relieve, or ameliorate ("treat") a disease, disorder, condition, or illness ("a condition"). Among the conditions to be treated in accordance with the present invention are conditions characterized by inappropriate expression or activity of alpha4beta7. Such conditions include those that are associated with inappropriate trafficking of cells, for example, the trafficking of leukocytes (such as lymphocytes or monocytes) to the gastrointestinal tract or other tissues comprising cells that express MAdCAM-1 (as a result of binding of the leukocytes to the cells that express MAdCAM-1). Diseases which can be treated accordingly include inflammatory bowel disease, such as ulcerative colitis, Crohn's disease, Celiac disease (nontropical Sprue), enteropathy associated with seronegative arthropathies, microscopic or collagenous colitis, eosinophilic gastroenteritis, or pouchitis resulting after proctocolectomy and ileoanal anastomosis. Additional conditions that may be treated in accordance with the present invention include pancreatitis, insulin-dependent diabetes mellitus, mastitis, cholecystitis, cholangitis, pericholangitis, chronic bronchitis, chronic sinusitis, asthma and graft versus host disease.

Therapeutic Methods and Administration of Antigen Binding Proteins

Certain methods provided herein comprise administering an alpha4beta7 heterodimer specific antigen binding protein to a subject, thereby reducing an alpha4beta7-induced biological response that plays a role in a particular condition. In particular embodiments, methods of the invention involve contacting endogenous alpha4beta7 with an alpha4beta7 antigen binding protein, e.g., via administration to a subject or in an ex vivo procedure.

The term "treatment" encompasses alleviation or prevention of at least one symptom or other aspect of a disorder, or reduction of disease severity, and the like. An antigen binding protein need not effect a complete cure, or eradicate every symptom or manifestation of a disease, to constitute a viable therapeutic agent. As is recognized in the pertinent field, drugs employed as therapeutic agents may reduce the severity of a given disease state, but need not abolish every manifestation of the disease to be regarded as useful therapeutic agents. Similarly, a prophylactically administered treatment need not be completely effective in preventing the onset of a condition in order to constitute a viable prophylactic agent. Simply reducing the impact of a disease (for example, by reducing the number or severity of its symptoms, or by increasing the effectiveness of another treatment, or by producing another beneficial effect), or reducing the likelihood that the disease will occur or worsen in a subject, is sufficient. One embodiment of the invention is directed to a method comprising administering to a patient an alpha4beta7 antagonist in an amount and for a time sufficient to induce a sustained improvement over baseline of an indicator that reflects the severity of the particular disorder.

As is understood in the pertinent field, pharmaceutical compositions comprising the molecules of the invention are administered to a subject in a manner appropriate to the indication. Pharmaceutical compositions may be administered by any suitable technique, including but not limited to parenterally, topically, or by inhalation. If injected, the pharmaceutical composition can be administered, for example, via intra-articular, intravenous, intramuscular, intralesional, intraperitoneal or subcutaneous routes, by bolus injection, or continuous infusion. Localized administration, e.g. at a site of disease or injury is contemplated, as are transdermal delivery and sustained release from implants. Delivery by inhalation includes, for example, nasal or oral inhalation, use of a nebulizer, inhalation of the antagonist in aerosol form, and the like. Other alternatives include eyedrops; oral preparations including pills, syrups, lozenges or chewing gum; and topical preparations such as lotions, gels, sprays, and ointments.

Use of antigen binding proteins in ex vivo procedures also is contemplated. For example, a patient's blood or other bodily fluid may be contacted with an antigen binding protein that binds alpha4beta7 ex vivo. The antigen binding protein may be bound to a suitable insoluble matrix or solid support material.

Advantageously, antigen binding proteins are administered in the form of a composition comprising one or more additional components such as a physiologically acceptable carrier, excipient or diluent. Optionally, the composition additionally comprises one or more physiologically active agents, for example, a second inflammation- or immune-inhibiting substance, an anti-angiogenic substance, an analgesic substance, etc., non-exclusive examples of which are provided herein. In various particular embodiments, the composition comprises one, two, three, four, five, or six physiologically active agents in addition to an alpha4beta7 binding antigen binding protein In one embodiment, the pharmaceutical composition comprise an antigen binding protein of the invention together with one or more substances selected from the group consisting of a buffer, an antioxidant such as ascorbic acid, a low molecular weight polypeptide (such as those having fewer than 10 amino acids), a protein, an amino acid, a carbohydrate such as glucose, sucrose or dextrins, a chelating agent such as EDTA, glutathione, a stabilizer, and an excipient. Neutral buffered saline or saline mixed with conspecific serum albumin are examples of appropriate diluents. In accordance with appropriate industry standards, preservatives such as benzyl alcohol may also be added. The composition may be formulated as a lyophilizate using appropriate excipient solutions (e.g., sucrose) as diluents. Suitable components are nontoxic to recipients at the dosages and concentrations employed. Further examples of components that may be employed in pharmaceutical formulations are presented in Remington's Pharmaceutical Sciences, $16^{th}$ Ed. (1980) and $20^{th}$ Ed. (2000), Mack Publishing Company, Easton, Pa.

Kits for use by medical practitioners include an alpha4beta7-inhibiting substance of the invention and a label or other instructions for use in treating any of the conditions discussed herein. In one embodiment, the kit includes a sterile preparation of one or more alpha4beta7 binding antigen binding proteins, which may be in the form of a composition as disclosed above, and may be in one or more vials.

Dosages and the frequency of administration may vary according to such factors as the route of administration, the particular antigen binding proteins employed, the nature and severity of the disease to be treated, whether the condition is acute or chronic, and the size and general condition of the subject. Appropriate dosages can be determined by procedures known in the pertinent art, e.g. in clinical trials that may involve dose escalation studies.

An alpha4beta7 inhibiting substance of the invention may be administered, for example, once or more than once, e.g., at regular intervals over a period of time. In particular embodiments, an antigen binding protein is administered over a period of at least a month or more, e.g., for one, two, or three months or even indefinitely. For treating chronic conditions, long-term treatment is generally most effective. However, for treating acute conditions, administration for shorter periods, e.g. from one to six weeks, may be sufficient. In general, the antigen binding protein is administered until the patient manifests a medically relevant degree of improvement over baseline for the chosen indicator or indicators.

Particular embodiments of the present invention involve administering an antigen binding protein at a dosage of from about 1 ng of antigen binding protein per kg of subject's weight per day ("1 ng/kg/day") to about 10 mg/kg/day, more preferably from about 500 ng/kg/day to about 5 mg/kg/day, and most preferably from about 5 µg/kg/day to about 2 mg/kg/day, to a subject. In additional embodiments, an antigen binding protein is administered to adults one time per week, two times per week, or three or more times per week, to treat an alpha4beta7 mediated disease, condition or disorder, e.g., a medical disorder disclosed herein. If injected, the effective amount of antigen binding protein per adult dose may range from 1-20 mg/m$^2$, and preferably is about 5-12 mg/m$^2$. Alternatively, a flat dose may be administered; the amount may range from 5-100 mg/dose. One range for a flat dose is about 20-30 mg per dose. In one embodiment of the invention, a flat dose of 25 mg/dose is repeatedly administered by injection. If a route of administration other than injection is used, the dose is appropriately adjusted in accordance with standard medical practices. One example of a therapeutic regimen involves injecting a dose of about 20-30 mg of antigen binding protein to one to three times per week over a period of at least three weeks, though treatment for longer periods may be necessary to induce the desired degree of improvement. For pediatric subjects (age 4-17), one exemplary suitable regimen involves the subcutaneous injection of 0.4 mg/kg, up to a maximum dose of 25 mg of antigen binding protein administered two or three times per week.

Particular embodiments of the methods provided herein involve subcutaneous injection of from 0.5 mg to 10 mg, preferably from 3 to 5 mg, of an antigen binding protein, once or twice per week. Another embodiment is directed to pulmonary administration (e.g., by nebulizer) of 3 or more mg of antigen binding protein once a week.

Examples of therapeutic regimens provided herein comprise subcutaneous injection of an antigen binding protein once a week, at a dose of 1.5 to 3 mg, to treat a condition in which alpha4beta7 plays a role. Examples of such conditions are provided herein and include, for example, rheumatic conditions as previously described, and other conditions in which excessive or inappropriate trafficking of alpha4beta7-expressing cells plays a role (described herein; for example, inflammatory bowel disease, pancreatitis, etc). Weekly administration of antigen binding protein is continued until a desired result is achieved, e.g., the subject's symptoms subside. Treatment may resume as needed, or, alternatively, maintenance doses may be administered.

Other examples of therapeutic regimens provided herein comprise subcutaneous or intravenous administration of a dose of 1, 3, 5, 6, 7, 8, 9, 10, 11, 12, 15, or 20 milligrams of an alpha4beta7 inhibitor of the present invention per kilogram body mass of the subject (mg/kg). The dose can be administered once to the subject, or more than once at a certain interval, for example, once a day, three times a week, twice a week, once a week, three times a month, twice a month, once a month, once every two months, once every three months, once every six months, or once a year. The duration of the treatment, and any changes to the dose and/or frequency of treatment, can be altered or varied during the course of treatment in order to meet the particular needs of the subject.

In another embodiment, an antigen binding protein is administered to the subject in an amount and for a time sufficient to induce an improvement, preferably a sustained improvement, in at least one indicator that reflects the severity of the disorder that is being treated. Various indicators that reflect the extent of the subject's illness, disease or condition may be assessed for determining whether the amount and time of the treatment is sufficient. Such indicators include, for example, clinically recognized indicators of disease severity, symptoms, or manifestations of the disorder in question. In one embodiment, an improvement is considered to be sustained if the subject exhibits the improvement on at least two occasions separated by two to four weeks. The degree of improvement generally is determined by a physician, who may make this determination based on signs, symptoms, biopsies, or other test results, and who may also employ questionnaires that are administered to the subject, such as quality-of-life questionnaires developed for a given disease.

Alteration of alpha4beta7 expression and/or activation of alpha4beta7, and or its binding partner MAdCAM-1, are associated with a number of disorders, including, for example, inflammatory conditions of the gastrointestinal system. Subjects with a given disorder may be screened, to identify those individuals who have altered alpha4beta7 or MAdCAM-1 expression and/or activation, thereby identifying the subjects who may benefit most from treatment with an alpha4beta7 binding antigen binding protein. Thus, treatment methods provided herein optionally comprise a first step of measuring a subject's alpha4beta7 or MAdCAM-1 activation or expression levels. An antigen binding protein may be administered to a subject in whom alpha4beta7 and/or MAdCAM-1 expression and/or activation is elevated above normal.

A subject's levels of alpha4beta7 or MAdCAM-1 activity may be monitored before, during and/or after treatment with an antigen binding protein, to detect changes, if any, in alpha4beta7 or MAdCAM-1 activity. For some disorders, the incidence of elevated alpha4beta7 and/or MAdCAM-1 activity may vary according to such factors as the stage of the disease or the particular form of the disease. Known techniques may be employed for measuring such activity, e.g., in a subject's blood or tissue samples. Alpha4beta7 or MAdCAM1 activity may be measured using any suitable technique.

Particular embodiments of methods and compositions of the invention involve the use of an antigen binding protein and one or more additional alpha4beta7 antagonists, for example, two or more antigen binding proteins of the invention, or an antigen binding protein of the invention and one or more other alpha4beta7 antagonists. In further embodiments, antigen binding protein are administered alone or in combination with other agents useful for treating the condition with which the patient is afflicted. Examples of such agents include both proteinaceous and non-proteinaceous drugs. When multiple therapeutics are co-administered, dosages may be adjusted accordingly, as is recognized in the pertinent art. "Co-administration" and combination therapy are not limited to simultaneous administration, but also include treatment regimens in which an antigen binding protein is administered at least once during a course of treatment that involves administering at least one other therapeutic agent to the patient.

Examples of other agents that may be co-administered with an antigen binding protein are other antigen binding proteins or therapeutic polypeptides that are chosen according to the particular condition to be treated. Alternatively, non-proteinaceous drugs that are useful in treating one of the particular conditions discussed above may be co-administered with an alpha4beta7 antagonist.

Combination Therapy

In another aspect, the present invention provides a method of treating a subject with an alpha4beta7 inhibiting antigen binding protein and one or more other treatments. In one embodiment, such a combination therapy achieves synergy or an additive effect by, for example, attacking multiple sites or molecular targets in a tumor. Types of combination therapies that can be used in connection with the present invention include inhibiting or activating (as appropriate) multiple nodes in a single disease-related pathway, multiple pathways in a target cell, and multiple cell types within a target tissue.

In another embodiment, a combination therapy method comprises administering to the subject two, three, four, five, six, or more of the alpha4beta7 agonists or antagonists described herein. In another embodiment, the method comprises administering to the subject two or more treatments that together inhibit or activate (directly or indirectly) alpha4beta7-mediated signal transduction. Examples of such methods include using combinations of two or more alpha4beta7 inhibiting antigen binding proteins, of an alpha4beta7 inhibiting antigen binding protein and one or more other therapeutic moiety having anti-inflammatory properties (for example, non-steroidal anti-inflammatory agents, steroids, and/or immunomodulators), or of an alpha4beta7 inhibiting antigen binding protein and one or more other treatments (e.g., surgery, ultrasound, or treatment effective to reduce inflammation). Useful agents that may be combined with alpha4beta7 inhibitors include those used to treat, for example, Crohn's disease or ulcerative colitis, such as aminosalicylate (for example, mesalamine), corticosteroids (including predisone), antibiotics such as metronidazole or ciprofloxacin (or other antibiotics useful for treating, for example, patients afflicted with fistulas), and immunosuppressives such as azathioprine, 6-mercaptopurine, methotrexate, tacrolimus and cyclosporine. Combinations of such agents are also contemplated for use with the inventive alpha4beta7 inhibitors. Such agent(s) may be administered orally or by another route, for example via suppository or enema.

Furthermore, one or more anti-alpha4beta7 antibodies or antibody derivatives can be used in combination with one or more molecules or other treatments, wherein the other molecule(s) and/or treatment(s) do not directly bind to or affect alpha4beta7, but which combination is effective for treating or preventing the condition being treated. For example, an alpha4eta7 inhibitor can be used in combination with probiotic therapy, or other therapy used to restore or maintain normal gut flora. In one embodiment, one or more of the molecule(s) and/or treatment(s) treats or prevents a condition that is caused by one or more of the other molecule(s) or treatment(s) in the course of therapy, e.g., nausea, fatigue, alopecia, cachexia, insomnia, etc. In every case where a combination of molecules and/or other treatments is used, the individual molecule(s) and/or treatment(s) can be administered in any order and/or any length of time, which is effective, e.g., simultaneously, consecutively, or alternately. In one embodiment, the method of treatment comprises completing a first course of treatment with one molecule or other treatment before beginning a second course of treatment. The length of time between the end of the first course of treatment and beginning of the second course of treatment can be any length of time that allows the total course of therapy to be effective, e.g., seconds, minutes, hours, days, weeks, months, or even years.

In another embodiment, the method comprises administering one or more of the alpha4beta7 antagonists described herein and one or more other treatments (e.g., a therapeutic or palliative treatment). Where a method comprises administering more than one treatment to a subject, it is to be understood that the order, timing, number, concentration, and volume of the administrations is limited only by the medical requirements and limitations of the treatment, i.e., two treatments can be administered to the subject, e.g., simultaneously, consecutively, alternately, or according to any other regimen.

The following examples, both actual and prophetic, are provided for the purpose of illustrating specific embodiments or features of the instant invention and do not limit its scope.

EXAMPLE 1

Preparation of Antibodies

Monoclonal antibodies against human alpha4beta7 were developed by immunizing XenoMouse™ XG2kappalambda (kl) and XG4kl mice (transgenic mice that express human IgG2 or IgG4, and human kappa and lambda light chains, respectively; Abgenix Inc., Fremont Calif.) with cells expressing human alpha4beta7, either transiently transfected human embryonic kidney (HEK) 293 cells (293-a4b7) or stably transfected Chinese hamster ovary (CHO) cells (CHO-a4b7). Serum titer was monitored by fluorescence activated cell sorter (FACS) analysis comparing alpha4beta7 transfected cells to the respective parental control cells. Hyperimmune animals from either immunization campaign were sacrificed and spleen and lymph node tissues were subjected to hybridoma fusion.

Alpha4beta7 heterodimer specific antibodies were identified using a series of assays. Hybridoma supernatants were first screened by Fluorometric Microvolume Assay Technology (FMAT™ Applera Corporation, Foster City Calif.; a high-throughput screening cellular detection system) for binding to alpha4beta7 transfected cells as compared to mock-transfected cells. Supernatants identified as positive for binding to alpha4beta7 (1001 positive binding supernatants from CHO-a4b7 cell immunization campaign and 1143 positive binding supernatants from 293-a4b7 cell immunization campaign) were evaluated for the ability to inhibit HUT78 cell adhesion to MAdCAM-1-Fc in a similar fashion as described (Erle, J. Immunol, (1994) 153:517). In this assay, 60 supernatants from CHO-a4b7 campaign and 174 supernatants from 293-a4b7 campaign showed greater than 90% inhibition (n=2) and were subject to further specificity and potency analysis.

Alpha4beta7-transfected, alpha4beta1-transfected, and alphaEbeta7-transfected 293 cells were prepared and used in FACS analysis with the hybridoma supernatants that were identified in the inhibition assay. Supernatants that demonstrated binding to only the alpha4beta7 transfected cells were classified as heterodimers-specific, since antibodies to the alpha4 subunit of this integrin would also bind the alpha4beta1-transfected cells, and antibodies that bound the beta7 chain would bind alphaEbeta7-transfected cells. The hybridoma supernatants were also analyzed for binding activity to cynomologous monkey alpha4beta7-transfected 293 cells by FACS analysis. Seven lines from the CHO-a4b7 campaign and 25 lines from the 293-a4b7 campaign were selected for sub-cloning and further analysis.

EXAMPLE 2

Analysis of Antibodies

The antibody-secreting cells obtained were cloned, and the antibody-encoding nucleic acids were isolated and sequenced. Site directed mutagenesis was used to prepared variants that differed from the isolated sequences at one or more amino acid residues. The amino acid sequence of the light and heavy chains of the antibodies and variants are shown in Tables 1 and 2 below. It is recognized that the boundaries of the CDR and FR regions can vary from that shown below, as discussed previously herein.

TABLE 1

| Light chain | FR1 | CDR1 | FR2 | CDR2 |
|---|---|---|---|---|
| 1A10K | DIQMTQSPSSVSASVGDRVTITC | RASQGVSSWLA | WYQQKPGMAPKLLIY | AASILQS |
| 11E7K1 | EIVMTQSPATLSVSPGETATLSC | RASQTVSSNLA | WYQQKPGQAPRLLIY | GASTRAT |
| 11E7K2 | DIQMTQSPSSLSASIGDRVTITC | RASQGIRNYLA | WYQRKPGKVPKLLIY | AASTLQS |
| 2F12K | DIQMTQSPSSVFASVGDRVTITC | RASQGISSWLA | WYQQKPGKAPNLLIY | GASSLQN |
| 14E4L | QSVLTQPPSVSAAPGQKVTISC | SGSSSNIGNNYVS | WYQQLPGTAPKLLIY | DNNKRPS |
| 3A5K | DIQMTQSPSSVSASVGDRVTITC | RASQGVISWLA | WYQQKPGMAPKLLIY | AASILQS |
| 10D7K | DIQMTQSPSSVSASVGDRVTITC | RASQGVNNWLA | WYQQKPGKAPKLLIF | ATSSLQS |
| 27D8K | EIVMMQSPATLSVSPGERATLSC | RASQSVSTNLA | WYQQKPGQAPRLLIY | GASTRAT |
| 18A11K | DIQMTQSPSSVSASVGDRVTITC | RASQGISSWLA | WYQQKPGKAPKLLIY | GASNLES |
| 20D7K | EIVLTQSPGTLSLSPGERATLSC | RASQSVSSSYLA | WYQQKPGQAPRLLIY | GASSRAT |
| 23H6K | EIVMTQSPATLSVSPGERATLSC | RASQSVNSNLA | WYQQKPGQAPRLLIY | GASTRAT |
| 27G8L | QSVLTQPPSVSEAPRQRVTISC | SGSNSNIGNNPVN | WYQLFPGRAPKLLIY | HDDLLPS |
| 26C7K | EIVMTQSPATLSVSPGERATLSC | RASQSVSDNLA | WYQQKPGQPPRLLIY | GASTRAT |
| 26H3K | DIQMTQSPSSLSASVGDRVTITC | QASQDISNYLN | WYQQKPGKAPKLLIY | DASNLET |
| 19G6K | DIQMTQSPSSLSASVGDRVTISC | QASQDINTYLN | WYQQKPGKVPKLLIY | DASNLET |
| 22B2K | DVQMTQSPSSLSASVGDRVTITC | QASQDITDYLN | WYQQKPGKAPKLLIY | DTSNLEA |
| 24A2K | EVMMTQSPATLSVSPGERATLSC | RASQSVSSNLA | WYQQKPGQAPRLLIF | GASTRAT |
| 26E9K | ELVMTQSPATLSVSPGERATVSC | RASQSVSSDLA | WYQQKPGQAPRLLIY | GASSRAT |
| 22F5K | EIVMTQSPATLSVFPGEGATLSC | RASQSVSSDLA | WYQQKPGQAPRLLIY | GASARAT |
| 26C10K | EIVLTQSPGTLSLSPGEGATLSC | RASQTVTSSYLA | WYQQSPSQSPRLLIY | GASTRAT |
| 17C8K | EIVMTQSPATLSVSPGERATLSC | RASQSVSSNLV | WYQQKPGQAPRLLIY | GASTRAT |
| 25C9k | DIQMTQSPSSVSASVGDRVTITC | RASQDISSWLA | WYQRKPGKAPKVLIY | SASSLQS |
| 19E6L | SYELTQPPSVSVSPGQTASITC | SGDKLGDKYAC | WYQQKPGQSPVLVIY | QDSKRPS |
| 26G2k | DIQMTQSPSSVSASVGDRVTITC | RASQDISSWLA | WYQQKPGTAPKVLIY | SASSLQN |
| 27G8L (a) | QSVLTQPPSVSGAPRQRVTISC | SGSNSNIGNNPVN | WYQLFPGRAPKLLIY | HDDLLPS |
| 27G8L (b) | QSVLTQPRSVSGAPRQRVTISC | SGSNSNIGNNPVN | WYQLFPGRAPKLLIY | HDDLLPS |
| 26H3K (c) | DIQMTQSPSSLSASVGDRVTITC | QASQDISNYLN | WYQQKPGKAPKLLIY | DASNLET |
| 1A10K (d) | DIQMTQSPSSVSASVGDRVTITC | RASQGVSSWLA | WYQQKPGKAPKLLIY | AASTLQS |

| Light chain | FR3 | CDR3 | FR4 |
|---|---|---|---|
| 1A10K | GVPSRFSGSGSGTDFTLTISSLQPEDFATYYC | QQANSFPWT | FGQGTKVEIK |
| 11E7K1 | GIPARFSGSGSGTEFTLTISSLQSEDFAVYYC | QQYDYWPPLT | FGGGTRVEIK |
| 11E7K2 | GVPSRFSGSGSGTDFTLTISSLQPEDVATYCC | QKYDSAPFT | FGPGTKVDIK |
| 2F12K | GVPLRFSGSGSGTDFTLTISSLQPEDFATYYC | QQANSFPWT | FGQGTKVEIK |

TABLE 1-continued

Sequence analysis of light chains

| | | | |
|---|---|---|---|
| 14E4L | GIPDRFSGSKSGTSAILDITGLQTGDEADYYC | GTWDSSLSAGRV | FGGGTKLTVL |
| 3A5K | GVPSRFSGSGSGTDFTLTISSLQPEDFATYYC | QQANSFPWT | FGQGTNVEIK |
| 10D7K | GVPSRFSGSGSGTDFTLTINSLQPEDFATYYC | QQVNSFPGT | FGQGTKVEIK |
| 27D8K | GIPARFSGSGSGTEFTLTISSLQSEDFAVYFC | QQYNDWPT | FGGGTKVEIK |
| 18A11K | GVPSRFSGSGSGTDFTLTISSLQPEDFANYYC | QQANSFPWT | FGQGTKVEIK |
| 20D7K | GIPDRFSGSGSGTDFTLTISRLEPEDFAVYYC | QQYDSSPPT | FGGGTKVAIK |
| 23H6K | GIPARFSGSGSGTEFTLTISSLQSEDFAVYYC | QQYDDWPPVT | FGQGTRLEIK |
| 27G8L | GVSDRFSGSRSGTSASLAISGLQSEDETDYYC | TAWDDSLNGWV | FGGGTKLTVL |
| 26C7K | GIPARFSGSGSGTEFTLTISSLQSEDFAVYYC | QQYDDWPT | FGGGTRVEIK |
| 26H3K | GVPSRFSGSGSGTDFTFTINSLQPEDIATYFC | QQYDNLPCS | FGQGTKLEIK |
| 19G6K | GVPSRFSGSGSGTDFTFTISGLQPEDIATYYC | QQFDNLPIT | FGQGTRLEIK |
| 22B2K | GVPSRFSGSGSGTDFTFTISSLQPEDIATYYC | QQYDILPYS | FGQGTDLEIK |
| 24A2K | GIPARFSGSGSGTEFTLTISSLQSEDFAVYCC | QQYDDWPT | FGGGTKVEIK |
| 26E9K | GIPARFSGSGSGTEFTLTISSLQSEDFAVYYC | QQYNNWPPLT | FGGGTKVEIK |
| 22F5K | GIPARFSGSGSGTEFTLTISSLQSEDFAVYYC | QQYHDWPPLS | FGGGTKVEIK |
| 26C10K | GIPDRFSGSGSGTDFTLTISRLEPEDFAVYYC | QQYDSSPPT | FGGGTKVEIK |
| 17C8K | GIPARFSGSGSGTDFTLTISSLQSEDFAVYYC | QQYDDWPPLT | FGGGTTVEIK |
| 25C9k | GVPSRFSGSGSGTDFTLTISSLQPEDFATYYC | QQADSFPWT | FGQGTKVEIK |
| 19E6L | GIPERFSGSNSGNTATLTISGTQAMDEADYYC | QAWDSSTVV | FGGGTKLTVL |
| 26G2k | GVPSRFSGRGSGTDFALTISSLQPEDFATYYC | QQADSFPWT | FGRGTKVEIK |
| 27G8L (a) | GVSDRFSGSRSGTSASLAISGLQSADETDYYC | TAWDDSLNGWV | FGGGTKLTVL |
| 27G8L (b) | GVSDRFSGSRSGTSASLAISGLRSADETDYYC | TAWDDSLNGWV | FGGGTKLTVL |
| 26H3K (c) | GVPSRFSGSGSGTDFTFTINSLQPEDIATYFC | QQYDNLPSS | FGQGTKLEIK |
| 1A10K (d) | GVPSRFSGSGSGTDFTLTISSLQPEDFATYYC | QQANSFPWT | FGQGTKVEIK |

TABLE 2

Sequence analysis of heavy chains

| Heavy chain | FR1 | CDR1 | FR2 | CDR2 |
|---|---|---|---|---|
| 1A10H | QVQLVQSGAEVKKPGASVKVSCKVSGYTLN | DLSMH | WVRQAPGKGLEWMG | GFDPAEGKIISAQKFQD |
| 11E7H1 | QVQLVESGGGLVKPGGSLRLSCVASGFTFS | DYYMS | WIRQAPGKGLEWVS | YISSSGSAIYYADSVKG |
| 11E7H2 | QVQLVESGGGVVQPGRSLRLSCAASGFTFS | SYGMH | WVRQAPGKGLEWVA | VIWYDGSNKYYADSVKG |
| 2F12H | QVQLVQSGAEVKKPGASVKVSCKVSGYTVT | DLSMH | WVRQAPGKGLEWMG | GFDPQDGETIYAQKFQG |
| 14E4H | QVQLVESGGGLVKPGGSLRLSCAASGFTFS | DYYMS | WIRQAPGKGLEWVS | YISNSGSVVYYADSVKG |
| 3A5H | QVQLVQSGAEVKKPGASVKVSCKVSGYTLN | DLSMH | WVRQAPGKGLEWMG | GFDPAEGKIISAQKFQD |
| 10D7H | QVQLVESGGGLVKPGGSLRLSCAASGFTFS | DYYMS | WIRQAPGKGLEWVS | YISSTGSAMYDADSVKG |
| 27D8H | QVQLVESGGGLVKPGGSLRLSCAASGFTFS | DNYMS | WIRQAPGKGLEWVS | YISSSGSATYYADSVKG |
| 18A11H | QVQLVQSGAEVKKPGASVKVSCKVSGYTLS | DLSIH | WVRQAPGKGLEWMG | GFDPQDGETIYAQKFQG |
| 20D7H | QVQLVESGGGLVKPGGSLRLSCTASGFTFS | DYYMS | WIRQAPGKGLEWVS | YISSSGSAIYYADSVKG |

TABLE 2-continued

Sequence analysis of heavy chains

| | | | |
|---|---|---|---|
| 23H6H | QVQLVESGGGLVKPGGSLRLSCAASGFTFS | DYYMS | WIRQAPGKGLEWVS YISSSGSAMYSADSVKG |
| 26G2H | QVQLVESGGGLVKPGGSLRLSCAASGFTFS | DYYMS | WIRQAPGKGLEWVS YISSIGSAIHYADSVKG |
| 27G8H | EVQLVESGGGLVQPGGSLRLSCAASGFTFS | SYWMS | WVRQASGKGLEWVA NIKQDGSEKYYVDSVKG |
| 26C7H | QVQLVESGGGLVKPGGSLRLSCAASGFTFS | DYYMS | WIRQAPGKGLEWVS YISRVGSTTYYADSVKG |
| 26H3H | EVQLVQSGAEVKKPGESLKISCKGSGYSFT | GYWIG | WVRQMPGKGLEWMG IIYPYDSDTRYSPSFQG |
| 19G6H | QVQLVESGGDLVKPGGSLRLSCAASGFTFS | DYYMS | WIRQAPGKGLEWIS YISSSGSTMYYADSVKG |
| 22B2H | EVQLVQSGAEVKEPGESLKISCKGSGYIFT | SYWIA | WVRQLPGKGLEWMG IIDPNDSDTRYSPSFQG |
| 24A2H | QVQLVESGGDLVEPGGSLRLSCAASGFTFR | DYYMS | WIRQAPGKGLEWVS YISSSGSAIYYADSVKG |
| 26E9H | QVQLVESGGGLVKPGGSLRLSCAASGFTFR | DYYMS | WIRQAPGKGLEWVS YISSSGSTSYCADSVKG |
| 19E6H | EVQLLESGGGLVQPGGSLRLSCAASGFTFS | SYAMS | WVRQAPGKGLEWVS AISGSGGSTYYADSVKG |
| 22F5H | QVQLVESGGGLVKPGGSLRLSCAASGFTFS | DYYMS | WIRQAPGKGLEWVS YISSTGSTLYYADSVKG |
| 25C9H | QVQLVESGGGLVKPGGSLRLSCAASGFTFN | DYYMS | WIRQAPGKGLEWVS YISSSGSAIHYADSVKG |
| 26C10H | QVQLVESGGGLVKPGGSLRLSCVASGFTFS | DYYMS | WIRQTPGKGLEWVS YISSSGSAIHYADSVKG |
| 17C8H | QVQLVESGGGLVKPGGSLRLSCAASGFTFS | DYYMS | WIRQAPGKGLEWLS YISNSGSAMYYADSVKG |
| 1A10H(a) | QVQLVQSGAEVKKPGASVKVSCKVSGYTLN | DLSMH | WVRQAPGKGLEWMG GFDPAEGKIISAQKFQD |
| 27G8H(b) | EVQLVESGGGLVKPGRSLRLSCAASGFTFS | SYWMS | WVRQASGKGLEWVA NIKQDGSEKYYVDSVKG |

| Heavy chain | FR3 | CDR3 | FR4 |
|---|---|---|---|
| 1A10H | RVTMTDDTSTDTAYMELSSLRSEDSAVYYCAT | LDFSSWFDP | WGQGTLVTVSS |
| 11E7H1 | RFTISRDNAKNSLYLQLNSLRAEDTAVYYCAR | DYSSGWFYFDY | WGRGTLVTVSS |
| 11E7H2 | RFTISRDNSKNTLHLQMNSLRAEDTAVYYCAR | EHWNYAFDI | WGQGTMVTVSS |
| 2F12H | RVTMTEDTSTDTAYMELRSLRSEDTAVYYCTT | ESSSAWFDP | WGQGTLVTVSS |
| 14E4H | RFTISRHNAKNSLYLQMNSLRADDTAVYYCAR | DRSSAWDEAFDI | WGQGTMVTVSS |
| 3A5H | RVTMTDDTSTDTAYMELSSLRSEDSAVYYCAT | LDFSSWFDP | WGQGTLVTVSS |
| 10D7H | RFTISRDNAKNSLYLQMNSLRAEDTAVYYCAR | EFSSGWSYFDY | WGQGTLVTVSS |
| 27D8H | RFTISRDNAKNSLYLQMSSLRAEDTAVYYCAR | DYSSGWYYFDY | WGQGTLVTVSS |
| 18A11H | RVTMTEDTSTDTAYMELSSLKSEDTAVYYCAT | GSSSSWFDP | WGQGTLVTVSS |
| 20D7H | RFTISRDNAKNSLYLQMDSLRAEDTAVFYCAR | EHSSGYWYFDL | WGRGALVTVSS |
| 23H6H | RFTISRDNAKNSLYLQMNSLRAEDTAVYYCAR | EYSSGWYYFDY | WGRGTLVTVSS |
| 26G2H | RFTISRDNAKNSLYLQMNSLRAEDTAVYYCAR | EYSSGWAYFDY | WGQGTLVTVSS |
| 27G8H | RFTISRDNAKNSLYLQMNSLRAEDTAVYYCAR | EGGYDWNYADYYGMDV | WGQGTTVTVSS |
| 26C7H | RFTISRDNAKNSLYLQMNSLRAEDTAVYYCAR | DYSSGWYYFDY | WGQGTLVTVSS |
| 26H3H | QVTISADKSINTAYLQWSSLKASDTAMFYCAS | HRLWLGEFPGPLNI | WGQGTMVTVSS |
| 19G6H | RFTISRVNAKNSLYLQMNSLRAEDTAVYYCAR | DRSSGLVSFDY | WGQGTLVTVSS |
| 22B2H | QVTISADKSIHTAYLQWSSLKASDTAMYYCAT | HRLWLGTLPGGFYI | WGQGTMVTVSS |
| 24A2H | RFTISRDNPKNSLYLQMNSLRAEDTAVYYCAR | DFSSGYYYFDY | WGHGTLVTVSS |
| 26E9H | RFTISRDNAKNSLYLQMNSLRAEDTAVYYCAR | DYSSGWFYFDY | WGQGTLVTVSS |
| 19E6H | RFTISRDNSKNTLYLQMNSLRAEDTAVYYCAK | APYSSSWALGLGMDV | WGQGTTVTVSS |
| 22F5H | RFTISRDNAKNSLYLQMDSLRADDAAVYYCTR | EYSSGWFFFDY | WGQGTLVTVSS |

TABLE 2-continued

Sequence analysis of heavy chains

| | | | |
|---|---|---|---|
| 25C9H | RFTISRDNAKNSLYLQMNSLRAEDTAVYYCAR | EYSSGWAYFDY | WGQGTLVTVSS |
| 26C10H | RFTISRDNAKNSLYLQMDSLRAEDTAVFYCAR | DHSSGYWYFDL | WGRGTLVTVSS |
| 17C8H | RFTISRDNARNSLYLQMNSLRAEDTAVYYCAR | EYSSGWFFFES | WGQGTLVTVSS |
| 1A10H(a) | RVTMTRDTSTSTVYMELSSLRSEDTAVYYCAR | LDFSSWFDP | WGQGTLVTVSS |
| 27G8H(b) | RFTISRDNAKNSLYLQMNSLRAGDTAVYYCAR | EGGYDWNYADYYGMDV | WGQGTTVTVSS |

The amino acid sequences of the antibodies were further analyzed for similarities. The kappa light chains were grouped into three groups, and a consensus sequence was developed for each group. There were three antibodies with lambda light chains, none of which bore enough similarity to each other to form a group of related sequences from which a consensus sequence could be developed. Two of the variants developed varied in the lambda light chain. The heavy chains were grouped into four groups with a single heavy chain categorized into a fifth group, and a consensus sequence was developed for groups 1 through 4. These results are shown in Table 3(a) and 3(b) below; consensus sequences are shown in the Sequence Listing. The numbers in parentheses indicate the SEQ ID NO in the Sequence Listing.

TABLE 3(a)

Grouping of antibodies by kappa light chain, with corresponding heavy chain

| Kappa Group 1 (10 members) | Heavy chain group (H1-H5) | Kappa Group 2 (9 members) | Heavy chain group (H1-H5) | Kappa Group 3 (4 members) | Heavy chain group (H1-H5) |
|---|---|---|---|---|---|
| 20D7K (10) | H1 (38) | 11E7K2 (3) | H1 (31) | 22B2K (16) | H4 (45) |
| 11E7K1 (2) | H1 (30) | 10D7K (7) | H1 (35) | 19G6K (15) | H1 (44) |
| 26C10K (20) | H1 (51) | 3A5K (6) | H2 (34) | 26H3K (14) | H4 (43) |
| 23H6K (11) | H1 (39) | 1A10K (1) | H2 (29) | 26H3K(c) (27) | H4 (43) |
| 26C7K (13) | H1 (42) | 25C9K (22) | H1 (50) | | |
| 24A2K (17) | H1 (46) | 26G2K (24) | H1 (40) | | |
| 27D8K (8) | H1 (36) | 18A11K (9) | H2 (37) | | |
| 22F5 (19) | H1 (49) | 2F12K (4) | H2 (32) | | |
| 26E9K (18) | H1 (47) | 1A10K(d) (28) | H2 (53) | | |
| 17C8K (21) | H1 (52) | | | | |

TABLE 3(b)

Grouping of antibodies by lambda light chain, with corresponding heavy chain

| Lambda chains (3 antibodies, no consensus) | Heavy chain group (H1-H5) |
|---|---|
| 14E4 (5) | H1 (33) |
| 27G8 (12) | H3 (41) |
| 27G8(a) (25) | H3 (54) |
| 27G8(b) (26) | H3 (54) |
| 19E6 (23) | H5 (48) |

CDR boundaries within the consensus sequences (which may vary, as discussed previously) were as follows: Kappa Group 1 CDR124-35, CDR251-57, CDR390-99; Kappa Group 2 CDR124-34, CDR251-56, CDR389-97; Kappa Group 3 CDR124-34, CDR250-56, CDR389-97; Heavy Chain Group 1 CDR131-35, CDR250-66, CDR399-110; Heavy Chain Group 2 CDR131-35, CDR2 50-66, CDR399-107; Heavy Chain Group 3 CDR131-35, CDR250-66, CDR399-114; and Heavy Chain Group 4 CDR131-35, CDR250-66, CDR399-114.

EXAMPLE 3

Functional Assays

This example describes various assays that were used to characterize the antibodies.

HUT78 Adhesion Assay.

Coated plates (for example, Costar® 3368 96-well plates; Corning Incorporated Life Sciences, Lowell Mass.) are prepared by coating 96-well plates overnight at 4° C. with 20 microG/mL MAdCAM-1 (or a similar concentration of human IgG1 as a coating control) diluted in phosphate buffer pH9.0. The coating is removed and the plates are blocked with 100 microL of 3% BSA/PBS, incubated for 1 hr or more at room temp. The plates are washed three times with Hank's balanced salt solution (HBSS).

HUT78 cells (a human T cell lymphoma cell line that exhibits the features of a mature T cell line with inducer/helper phenotype; ATCC TIB 161), grown to confluency, are pelleted and washed 3× in HBSS, then resuspended in HBSS at appropriate concentration to yield ~30,000 cells in 50 microL.

Antibodies to be tested are diluted to twice the final concentration, and then titrated 1:4 in calcium-free, magnesium free HBSS containing 1% BSA with 1 mM $Mn^{2+}$. Fifty microL of antibody titration or control is added to each well of a VEE bottom plate, followed by 50 microL of HUT78 cells. The cells and antibodies are incubated at 4° C. for 30 minutes, then added to the coated plates and incubated at 37° C. for 40 minutes. Cells on coated plates are washed three times in room temperature HBSS, by flicking HBSS off between washes. The adherent cells are freeze-thawed at −20 C followed by the addition of 100 microL of CyQuant® dye/lysis buffer (a buffer used in a fluorescence-based cell quantification assays useful in high-throughput screening Molecular Probes®, Life Technologies Corporation, Carlsbad, Calif. The fluorescent signal from each well is quantitated at 485 nm excitation and 530 nm emission, for example using a Tecan GENiosPro, a multi-label microplate reader (Tecan Group Ltd. Männedorf, Switzerland).

Human CD4+ Cell Adhesion Assay

Plates are coated with human MAdCAM-1-Fc or human IgG (3 microG/ml in 20 mM phosphate buffer, pH 9.0, 130 mM NaCl), 100 microL/well, at 4° C. overnight then blocked with 200 microL/well blocking reagent (3% bovine serum albumen in PBS) at room temperature for at least two hours. Plates are then washed three times with adhesion buffer (30 mM HEPES, pH 7.4, 120 mM NaCl, 1 mM $MnCl_2$, 10 g/ml Human IgG).

Serial dilutions of antibodies to be tested are prepared, and added to the plate (35 microL/well); isolated $CD4^+$ T cells (250,000 cells/35 microL/well) are added and the plates are incubated at 4° C. for 2 hrs. After washing three times with adhesion buffer, plates are frozen at −20° C. overnight. Detection reagent (100 microL well CyQUANT® reagent; Life Technologies Corporation, Carlsbad, Calif.) is added and plates are incubated at 37° C. for 45 minutes. Results are determined by reading fluorescence at 485 nm excitation and 530 nm emission.

EC50 in Binding Human CD4+CD45RA-Memory T Cells

Human peripheral blood mononuclear cells (PBMC; fresh or frozen and thawed, for example in phosphate buffered saline with 2% FBS) are washed and resuspended in HEPES buffer (30 mM HEPES+140 nM NaCl) with 1% BSA, with or without 1 mM $MnCl_2$ (depending on the experiment; $Mn^{2+}$ is necessary for MAdCAM-1 binding) and plated into 96 well plates ($10^6$ cells/well). Cells are incubated with 10 microG/ml human IgG for 30 minutes on ice to block nonspecific binding. Cells are then incubated with serial dilutions of biotinylated anti-alpha4beta7 antibodies in 96 well plates for one hour on ice, followed by addition of 1:100 dilution of streptavidin-phycoerythrin (PE; Jackson ImmunoResearch Laboratories Inc., West Grove, Pa.), 4 microL CD3-Pacific Blue, CD4-PerCP-Cy5.5 and CD45RA-fluorescein isothiocyanate (FITC) (BD Biosciences, San Jose Calif.) for a final volume of 100 microL, and incubated for another hour on ice. Cells were washed twice with HEPES buffer (with or without $MnCl_2$, correspondingly) and then fixed in 200 microL HEPES buffer plus 0.5% paraformaldehyde (again, with or without $MnCl_2$, correspondingly). The percentage of positive alpha4beta7 antibody binding CD4+CD45RA-memory T cells is determined using a fluorescence activated cell sorter (FACS), for example, a BD™ LSR II benchtop flow cytometer (BD Biosciences, San Jose Calif.). EC50 is defined as the concentration of alpha4beta7 antibody at which 50% of the alpha4beta7 sites on CD4CD45RA-memory cells are bound by the alpha4beta7 antibody.

IC50 in Blocking MAdCAM-1-Fc Binding to Human CD4+ CD45RA-Memory T Cells.

PBMC (fresh or frozen as described previously) are washed and resuspended in HEPES buffer (30 mM HEPES+ 140 nM NaCl) with 1% BSA and 1 mM MnCl. to a final concentration of $10^7$ cells/ml. Cells are blocked as described previously; after blocking, cells are incubated with a serial dilution of anti-alpha4beta7 antibody (or appropriate control) in 96 well plates for 30 minutes on ice, and then with 0.3 microG/ml biotinylated MAdCAM-1-Fc protein for another one hour.

After two washes in HEPES buffer with 1 mM MnCl, cells are treated with 1:100 dilution of streptavidin-PE, 4 microL CD3-Pacific Blue, CD4-PerCP-Cy5.5 and CD45RA-FITC as described previously, in a final volume of 100 microL. After one hour incubation on ice, cells are washed twice with HEPES buffer with 1 mM MnCl and then fixed in 200 microL buffer plus 0.5% paraformaldehyde. The percentage of positive MAdCAM-1-Fc binding CD4+CD45RA-memory T cells is determined by fluorescence activated cell sorter (FACS) analysis, as described previously. IC50 is defined as the concentration of alpha4beta7 antibody at which MAdCAM-1-Fc binding to alpha4beta7 on CD4CD45RA-memory cells is inhibited by 50%.

Alpha4beta7 Induction by Retinoic Acid on Activated T Cells

Isolated human PBMC are activated by anti CD3 (plate bound, 5 microG/ml), human IL-2 (20 ng/ml) in the presence or absence of retinoic acid (1000 nM) for 7 days. The activated cells are washed twice with staining buffer (PBS plus 0.5% BSA and 1 mM MnCl) and incubated with 100 microG/ml human Ig for 30 minutes to block non-specific binding. The cells are first incubated in a serial dilution of anti-alpha4beta7 antibodies for 30 minutes on ice, and then stained with 1 microG/ml biotinylated MAdCAM-1-Fc for another 30 minutes. After twice washing with staining buffer, cells are stained with Streptavidin-PE (1:1000) for 30 minutes. The cells are analyzed by fluorescence activated cell sorting, for example, with a FACSCalibur™ (BD Biosciences, San Jose Calif.). Cells prepared in this manner may be used for additional experiments such as competition assays.

Competition Assays

Alpha4beta7 antibodies were also examined for their ability to compete with other anti-alpha4beta7 and/or beta7 antibodies in binding to alpha4 beta7 expressing cells by fluorometric microvolume assay technology or FMAT, substantially as described by Fiscella, et al., *Nature Biotechnology* 21:302-307; 2003. Briefly, cells expressing high levels of alpha4beta7 are prepared, for example by transient co-transfection of cells with nucleic acids encoding alpha4 and nucleic acids expressing beta7. Stable cell lines are prepared in a similar manner, using cells and protocols appropriate for stable transfection. Transfected cells are screened, for example, by FACS, using antibodies to alpha4, antibodies to beta7, and/or ligand (i.e., MAdCAM-1, for example, a MAdCAM-1-Fc fusion protein). Cells may undergo several cycles of sorting and selection to yield clonal cell lines with reproducible, elevated levels of alpha4beta7 expression.

Binding to S250N Mutant

Antibodies were also evaluated for their ability to recognize the S250N point mutant in the beta7 chain, which is known to be critical for ACT-1 binding (J. Immunol. 159: 1497, 1997). 293 cells transiently co-expressing alpha4beta7 having the S250N mutation in the beta chain (ref) are prepared in a similar manner as that previously described for preparation of cells expressing high levels of alpha4beta7. Briefly a total $1 \times 10^6$ transfected cells for profile are collected using cell-dissociation solution and spun down at 1000 rpm for 5 min. The cells are then blocked with 0.5 ml blocking buffer (1% goat serum/PBS) for 30 min to 1 hr at 4° C. with shaking. For MAdCAM-1-Fc staining, cells are incubated for 1 hr at 4° C. with shaking in $Mn^{2+}$ Buffer (1 mM $MnCl_2$ in 30 mM HEPES+1% goat serum). Cells are then spun down at 1000 rpm/5 min, and 0.5 ml of fresh blocking buffer with along with 10 microG/ml of primary antibody is added, followed by incubation for 30 min to 1 hr at 4° C. with shaking. After two washes with 4 ml of cold PBS (each wash), secondary antibody (i.e., goat-anti IgG-Phycoerythrin-conjugated antibody; Southern Biotech, 1:250 diluted or 0.1 microG/10⁶ cells) in 0.5 ml blocking buffer is added and cells are incubated for 20-30 min at 4° C. Cells are washed one final time with 4 mls of cold PBS, then resuspended in 0.5 ml of FACS buffer for profile.

Binding to Single Nucleotide Polymorphisms (SNPs)

For SNP analysis of the α4 subunit, α4 gene exons 1-28 from 90 individuals (180 haploid genomes) representing different ethnic groups were amplified by polymerase chain reaction (PCR) and subsequently sequenced. Three candidate SNPs in the coding region of the α4 gene were identified, and one of the three resulted in an amino acid change (Arg878Gln). Similarly for the β7 subunit SNP analysis, the coding region of β7 gene exons 2-15 from 90 individuals (180 haploid genomes) representing different ethnic groups were PCR amplified and subsequently sequenced. Three SNPs were identified, and two of them resulted in amino acid changes. The in-house SNP analysis data were compared with information in the NCBI database (NCBI: National Center for Biotechnology Information a division of the National Library of Medicine (NLM) at the National Institutes of Health (NIH)). Only the A/G mutation resulting in Gln878Arg in the α4 subunit occurs at high frequency—20% or 30% in both in-house SNP and the public database respectively. The other SNPs occur at low frequency. This information is summarized in Table 4 below.

TABLE 4

Frequency of SNPs in human beta7 and alpha4

|  | SNP | Alternative allele frequency - NCBI database | Alternative allele frequency - in-house analysis | Location |
|---|---|---|---|---|
| beta7 | E97V | NA | A(0.989)/T(0.019) | extracellular |
|  | R213S | C(0.975)/A(0.25) | No observation | extracellular |
|  | G611E | NA | No observation | extracellular |
|  | G629S | NA | A(0.989)/T(0.019) | extracellular |
|  | H672Y | NA | No observation | extracellular |
| alpha4 | V824A | T(0.972)/C(0.028) | No observation | extracellular |
|  | Q878R | A(0.648)/G(0.352) | A(0.783)/G(0.217) | extracellular |
|  | R1007S | NA | No observation | intracellular |

Point mutant constructs representing amino acid altering SNPs (a4b7(E97V); a4b7(R213S); a4b7(G629S); a4(V824A)b7; a4(Q878R)b7) in the extracellular domains of both alpha4 and beta7 were generated. Each point mutant construct was transfected to 293 cells along with the wild-type partner expression construct. Transfected 293 cells were first stained with 1 microG/ml of human IgG or anti-alpha4beta7 antibody, washed with PBS, and the stained with phycoerytherin conjugated secondary antibody goat-anti human IgG. After washing with PBS, cells were analyzed by fluorescence activated cell sorting, for example, with a FACSCalibur™ (BD Biosciences, San Jose Calif.). Fluorescence staining intensity (geometric mean) for each antibody staining is indicated in Table 5 below.

TABLE 5

Binding to SNPs

|  | wt | E97V | R213S | G629S | V824A | Q878R |
|---|---|---|---|---|---|---|
| IgG | 8 | 7 | 7 | 7 | 7 | 7 |
| 1A10 | 122 | 135 | 31 | 80 | 102 | 70 |
| 3A5 | 124 | 135 | 31 | 80 | 110 | 71 |

TABLE 5-continued

Binding to SNPs

|  | wt | E97V | R213S | G629S | V824A | Q878R |
|---|---|---|---|---|---|---|
| 2F12 | 129 | 134 | 37 | 80 | 112 | 73 |
| 18A11 | 92 | 105 | 30 | 63 | 82 | 56 |
| 22B2 | 97 | 108 | 58 | 65 | 85 | 58 |
| 26H3 | 93 | 106 | 49 | 62 | 82 | 55 |
| 27G8 | 102 | 116 | 59 | 68 | 88 | 58 |
| 26G2 | 99 | 113 | 38 | 64 | 86 | 58 |
| 17C8 | 93 | 96 | 49 | 58 | 74 | 51 |
| 19G6 | 94 | 108 | 46 | 59 | 67 | 46 |
| 25C9 | 96 | 106 | 33 | 59 | 77 | 51 |

These results indicated that all of the antibodies tested bound to the known SNPs of alpha4beta7.

The activities of various alpha4beta7heterodimer specific antibodies in several different assays are compared in Table 6 below.

TABLE 6

Characterization of antibodies to alpha4beta7

| Antibody | HUT78 Adhesion IC50 (ng/ml) | MAdCAM-1 Competition IC50 (ng/mL) | CD4+CD45RA- Cell Binding EC50 (ng/mL) | a4b7 (S250N) Binding |
|---|---|---|---|---|
| 1A10 | 6.1 | 6.2 | 4.9 | − |
| 3A5 | 7.5 | 6.2 | 5.6 | − |
| 2F12 | 11.4 | 4.6 | 3.3 | − |
| 18A11 | 7.4 | 7.3 | 4.7 | − |
| 22B2 | 3.7 | 23.2 | 5.1 | − |
| 26H3 | 8.9 | 14.1 | 9.3 | − |
| 27G8 | 14.9 | 8.7 | 6.3 | − |
| 26G2 | 6.9 | 99.6 | 32.6 | + |
| 17C8 | 6.8 | 31.1 | 22.9 | + |
| 19G6 | 12.2 | 103.3 | 32.9 | + |
| 25C9 | 13.7 | 77.6 | NA | + |

Soler et al. reported the binding specificity of a humanized anti-alpha4beta7 antibody known as vedolizumab (J Pharmacol Exp Ther 330:864; 2009). This antibody was reported to have an EC50 on memory CD4+ T lymphocytes of 0.042 microgr/ml (42 ng/ml). Vedolizumab also inhibited the binding of soluble MAdCAM-1 to alpha4beta7hi memory T cells with an 1050 of 0.034 microgr/ml (34 ng/ml). In contrast, many of the antibodies shown in Table 6 have an EC50 on memory T cells (i.e., CD4+CD45RA-cells) of less than 10 ng/ml, and all of them have an EC50 of less than 35 ng/ml (all also have an EC50 of greater than 0.1 ng/ml in this assay). Additionally, several of the antibodies shown in Table 6 demonstrated an IC50 in a MAdCAM competition assay of less than 10 ng/ml, and many demonstrated an 1050 of less than 30 ng/ml (all also exhibited an IC50 of greater than 0.1 ng/ml in this assay). Although Soler et al. made no mention of the ability of vedolizumab to bind an S250N mutant of alpha4beta7, the murine antibody ACT-1 from which vedolizumab is derived is known to be unable to bind an S250N mutant (Tidswell et al., J Immunol 159:1497; 1997), and according to Soler et al., vedolizumab and ACT-1 exhibit the same antigen specificity. Thus, vedolizumab also does not bind the S250N mutant, in contrast to several of the antibodies shown in Table 6.

EXAMPLE 4

Additional Analysis

Several representative antibodies with different properties in the afore-mentioned functional assays were chosen for additional analysis as described below.

Binding Affinity to Human a4b7

To measure cell binding affinity of human anti-alpha4beta7antibodies, a Kinetic Exclusion Assay which measures binding events in solution phase can be used to calculate the equilibrium dissociation constant, $K_d$. KinExA® Technology (Sapidyne Instruments, Boise, Id.) was used, substantially as described previously by Xie et. al. *J. Imm, Methods* 304:1 (2005) and Rathanaswami et. al. *Anal. Biochem.* 373:52 (2008). Briefly, HUT78 cells expressing human alpha4beta7 were titrated 1 in 3 from ~$50^6$ cells/mL to ~400 cells/mL and then equilibrated with a final concentration of either 2 or 30 pM of mAb 2F12 or 18A11 and 30 or 500 pM for 17C8 for 18 hours at 4° C. The free antibody remaining in the supernatant at equilibrium was measured by KinExA® technology by passing the supernatant over PMMA beads pre-coated with goat anti-human Fc and detected with goat anti-human (H+L) Cy5 (substantially as described by Rathanaswami et al. *Biochem Biophys Research Commun:* 1004 (2005). The equilibrium dissociation constant ($K_d$) is obtained using KinExA® software by "n-curve analysis" which fits all of the given curves to a single $K_d$ value simultaneously (Rathanswami et al. 2005 and Xie et al., supra).; results are shown below in Table 7.

TABLE 7

Binding affinity of antibodies

| Antibody | Kd (pM) | Ratio (low Ab) | % error | Kd low | Kd high |
|---|---|---|---|---|---|
| 2F12 | 4.56 | 0.44 | 3.80 | 1.94 | 11.12 |
| 18A11 | 0.90 | 2.22 | 4.40 | 0.23 | 2.29 |
| 17C8 | 29.36 | 1.02 | 3.58 | 12.09 | 74.53 |

These antibodies demonstrated a Kd in a KinExA® assay greater than 0.05 pM, but less than 80 pM, less than 15 pM, or less than 5 pM.

PK/PD Characteristics

A single-dose pharmacokinetic (PK) and pharmacodynamic (PD) study of three fully human anti-alpha4beta7 antibodies in male cynomologous monkeys was conducted following intravenous (IV; 5 mg/kg) or subcutaneous (SC; 0.5 or 5 mg/kg) administration. Similar initial PK exposure ($C_o$; concentration at time zero) and distribution within the central circulation after 5 mg/kg IV was observed. After SC administration, both $C_{max}$ (maximum concentration in serum) and AUC (area under the concentration-time curve) exhibited dose-proportionality within the 0.5-5 mg/kg SC dose range for all three antibodies. The absolute bioavailability after SC for the three tested antibodies ranged from 44 to 68%.

Free alpha4beta7 on T cells before and after antibody treatment were quantified by PE-conjugated anti-alpha4beta7 antibody 27G8. The background level was controlled by staining with PE-conjugated anti-alpha4beta7 antibody 27G8 in the presence of 10 mg/ml antibody being tested before and after antibody treatment. Fractional saturation was determined by percentage of free alpha4beta7 sites in comparison to the pre-treatment for each antibody. CD4-PerCP, CD99-APC and CD28-FITC were used to distinguish naive, central memory and effector memory cells. Fractional saturation of alpha4beta7 on naive T cells was shown because of the variability and limited assay sensitivity in the cynomologous memory cell population. For 18A11 treatment, all three dosage groups remained saturated from day 1 to day 14. At day 29, all three groups lost coverage. In both 2F12 and 17C8 treatment, loss of target coverage was observed on day 14 at the low dosage (0.5 mg/Kg) group.

In addition to free alpha4beta7 detection, target saturation was also determined by staining with PE-conjugated anti-human antibody A35 in the absence or presence of 10 mg/ml antibody. Total alpha4beta7 sites were estimated with pre-incubation of samples with 10 mg/ml anti-alpha4beta7 antibody followed by staining with anti-human antibody. Target saturation was determined by the percentage of total alpha4beta7 sites occupied by the anti-alpha4beta7 antibodies for each sample. The three fully human anti-alpha4beta7 antibodies demonstrated saturation of alpha4beta7 that was maintained at mean of 81 to 100% within 14 days after 5 mg/kg IV.

PK/PD modeling was conducted on serum anti-alpha4beta7 antibody concentrations and corresponding alpha4beta7 receptor saturation data using a direct $E_{max}$ model. The model estimated PD parameters are $E_{max}$(maximum alpha4beta7 receptor saturation) of 92%, $EC_{50}$ (anti-alpha4beta7 antibody concentration at which 50% of the $E_{max}$ was reached) of 52 ng/mL, and $E_0$ (initial alpha4beta7 receptor saturation) of 18%. All three antibodies exhibited potent in vivo PD effects on saturating alpha4beta7 receptors with average $t_{1/2}$ of ~3-5 days in cynomolgus monkeys.

What is claimed is:

1. An isolated, alpha4beta7 heterodimer specific antigen binding protein having a heavy chain variable region comprising CDR1, CDR2 and CDR3 from SEQ ID NO:37, and a light chain variable region comprising CDR1, CDR2 and CDR3 from SEQ ID NO:9.

2. The heterodimer specific antigen binding protein of claim 1, wherein the light chain variable region is at least 90% identical to SEQ ID NO:9, and the heavy chain variable region is at least 90% identical to SEQ ID NO:37.

3. The heterodimer specific antigen binding protein of claim 2, wherein the light chain variable region comprises SEQ ID NO:9, and the heavy chain variable region is selected from the group consisting of a polypeptide that comprises SEQ ID NO:37 and a polypeptide that comprises SEQ ID NO:37 wherein the N-terminal amino acid is converted to pyroglutamic acid.

4. A composition comprising the protein of claim 3 and a physiologically acceptable diluent, excipient or carrier.

5. The isolated, alpha4beta7 heterodimer specific antigen binding protein of claim 3, which further comprises a light chain constant region and a heavy chain constant region.

6. The isolated, alpha4beta7 heterodimer specific antigen binding protein of claim 5 wherein the light chain constant region is a kappa-type light chain constant region; and the heavy chain constant region is selected from the group consisting of:
- a') a constant region from an IgD antibody;
- b') a constant region from an IgE antibody;
- c') a constant region from an IgM antibody;
- d') a constant region from an IgG1 antibody;
- e') a constant region from an IgG2 antibody;
- f') a constant region from an IgG3 antibody;
- g') a constant region from an IgG4 antibody; and
- h') a constant region from an IgG4 antibody having at least one mutation in a hinge region that alleviates a tendency to form intra-H chain disulfide bond.

7. A composition comprising the protein of claim 6 and a physiologically acceptable diluent, excipient or carrier.

8. The isolated, alpha4beta7 heterodimer specific antigen binding protein of claim 5 wherein the light chain constant region is selected from the group consisting of:
- a) a polypeptide comprising SEQ ID NO:70;
- b) a polypeptide at least 90% identical to SEQ ID NO:70;
- c) a polypeptide of a) which incorporates one or more post-translational modifications; and
- d) a polypeptide having an amino acid sequence as set forth in SEQ ID NO:70 from which one, two, three, four or five N-terminal and/or C-terminal amino acids have been removed, and the heavy chain constant region is selected from the group consisting of:
- a') a polypeptide comprising SEQ ID NO:72;
- b') a polypeptide at least 90% identical to SEQ ID NO:72;
- c') a polypeptide of a') which incorporates one or more post-translational modifications; and
- d') a polypeptide having an amino acid sequence as set forth in SEQ NO:72 from which one, two, three, four or five N-terminal and/or C-terminal amino acids have been removed.

9. A composition comprising the protein of claim 8 and a physiologically acceptable diluent, excipient or carrier.

10. A composition comprising the protein of claim 5 and a physiologically acceptable diluent, excipient or carrier.

11. The isolated, alpha4beta7 heterodimer specific antigen binding protein of claim 1, which further comprises a light chain constant region and a heavy chain constant region.

12. The isolated, alpha4beta7 heterodimer specific antigen binding protein of claim 11 wherein the light chain constant region is a kappa-type light chain constant region; and the heavy chain constant region is selected from the group consisting of:
- a') a constant region from an IgD antibody;
- b') a constant region from an IgE antibody;
- c') a constant region from an IgM antibody;
- d') a constant region from an IgG1 antibody;
- e') a constant region from an IgG2 antibody;
- f') a constant region from an IgG3 antibody;
- g') a constant region from an IgG4 antibody; and
- h') a constant region from an IgG4 antibody having at least one mutation in a hinge region that alleviates a tendency to form intra-H chain disulfide bond.

13. A composition comprising protein of claim 12 and a physiologically acceptable diluent, excipient or carrier.

14. The isolated, alpha4beta7 heterodimer specific antigen binding protein of claim 11 wherein the light chain constant region is selected from the group consisting of:
- a) a polypeptide comprising SEQ ID NO:70;
- b) a polypeptide at least 90% identical to SEQ ID NO:70;
- c) a polypeptide of a) which incorporates one or more post-translational modifications; and
- d) a polypeptide having an amino acid sequence as set forth in SEQ ID NO:70 from which one, two, three, four or five N-terminal and/or C-terminal amino acids have been removed, and the heavy chain constant region is selected from the group consisting of:
- a') a polypeptide comprising SEQ ID NO:72;
- b') a polypeptide at least 90% identical to SEQ ID NO:72;
- c') a polypeptide of a') which incorporates one or more post-translational modifications; and
- d') a polypeptide having an amino acid sequence as set forth in SEQ ID NO:72 from which one, two, three, four or five N-terminal and/or C-terminal amino acids have been removed.

15. A composition comprising the protein of claim 14 and a physiologically acceptable diluent, excipient or carrier.

16. A composition comprising the protein of claim 11 and a physiologically acceptable diluent, excipient or carrier.

17. A composition comprising the protein of claim 2 and a physiologically acceptable diluent, excipient or carrier.

18. The isolated, alpha4beta7 heterodimer specific antigen binding protein of claim 2 which further comprises a light chain constant region and a heavy chain constant region.

19. The isolated, alpha4beta7 heterodimer specific antigen binding protein of claim 18 wherein the light chain constant region is a kappa-type light chain constant region; and the heavy chain constant region is selected from the group consisting of:
- a') a constant region from an IgD antibody;
- b') a constant region from an IgE antibody;
- c') a constant region from an IgM antibody;
- d') a constant region from an IgG1 antibody;
- e') a constant region from an IgG2 antibody;
- f') a constant region from an IgG3 antibody;
- g') a constant region from an IgG4 antibody; and
- h') a constant region from an IgG4 antibody having at least one mutation in a hinge region that alleviates a tendency to form intra-H chain disulfide bond.

20. A composition comprising the protein of claim 19 and a physiologically acceptable diluent, excipient or carrier.

21. The isolated, alpha4beta7 heterodimer specific antigen binding protein of claim 18 wherein the light chain constant region is selected from the group consisting of:
- a) a polypeptide comprising SEQ ID NO:70;
- b) a polypeptide at least 90% identical to SEQ ID NO:70;
- c) a polypeptide of a) which incorporates one or more post-translational modifications; and
- d) a polypeptide having an amino acid sequence as set forth in SEQ ID NO:70 from which one, two, three, four or five N-terminal and/or C-terminal amino acids have been removed, and the heavy chain constant region is selected from the group consisting of:
- a') a polypeptide comprising SEQ ID NO:72;
- b') a polypeptide at least 90% identical to SEQ ID NO:72;
- c') a polypeptide of a') which incorporates one or more post-translational modifications; and
- d') a polypeptide having an amino acid sequence as set forth in SEQ ID NO:72 from which one, two, three, four or five N-terminal and/or C-terminal amino acids have been removed.

22. A composition comprising the protein of claim 21 and a physiologically acceptable diluent, excipient or carrier.

23. A composition comprising the protein of claim 18 and a physiologically acceptable diluent, excipient or carrier.

24. A composition comprising the protein of claim 1 and a physiologically acceptable diluent, excipient or carrier.

25. An isolated, alpha4beta7 heterodimer specific antigen binding protein having a heavy chain variable region and a light chain variable region, wherein the heavy chain variable region is encoded by a nucleic acid that encodes SEQ ID NO:37, and the light chain variable region is encoded by a nucleic acid that encodes SEQ ID NO:9.

26. A composition comprising the protein of claim 25 and a physiologically acceptable diluent, excipient or carrier.

27. The isolated, alpha4beta7 heterodimer specific antigen binding protein of claim 25 wherein the nucleic acid that encodes the heavy chain variable region comprises SEQ ID NO:64, and the nucleic acid that encodes the light chain variable region comprises SEQ ID NO:63.

28. A composition comprising the protein of claim 27 and a physiologically acceptable diluent, excipient or carrier.

29. The isolated, alpha4beta7 heterodimer specific antigen binding protein of claim 27, which further comprises a light chain constant region and a heavy china constant region, wherein the light chain constant region is encoded by a nucleic acid that encodes SEQ ID NO:70 and the heavy chain constant region is encoded by a nucleic acid that encodes SEQ ID NO:72.

30. The isolated, alpha4beta7 heterodimer specific antigen binding protein of claim 29 wherein the heavy chain constant region is encoded by a nucleic acid that comprises SEQ NO:69, and the light chain constant region is encoded by a nucleic acid that comprises SEQ ID NO:71.

31. A composition comprising the protein of claim 30 and a physiologically acceptable diluent, excipient or carrier.

32. A composition comprising the protein of claim 29 and a physiologically acceptable diluent, excipient or carrier.

33. The isolated, alpha4beta7 heterodimer specific antigen binding protein of claim 25, which further comprises a light chain constant region and a heavy china constant region, wherein the light chain constant region is encoded by a nucleic acid that encodes SEQ ID NO:70 and the heavy chain constant region is encoded by a nucleic acid that encodes SEQ ID NO:72.

34. The isolated, alpha4beta7 heterodimer specific antigen binding protein of claim 33 wherein the heavy chain constant region is encoded by a nucleic acid that comprises SEQ ID NO:69, and the light chain constant region is encoded by a nucleic acid that comprises SEQ ID NO:71.

35. A composition comprising the protein of claim 34 and a physiologically acceptable diluent, excipient or carrier.

36. A composition comprising the protein of claim 33 and a physiologically acceptable diluent, excipient or carrier.

\* \* \* \* \*